US012305184B2

United States Patent
Ascencio-Ibanez et al.

(10) Patent No.: US 12,305,184 B2
(45) Date of Patent: May 20, 2025

(54) COMPOSITIONS AND METHODS FOR CONFERRING RESISTANCE TO GEMINIVIRUS

(71) Applicant: North Carolina State University, Raleigh, NC (US)

(72) Inventors: Jose Trinidad Ascencio-Ibanez, Raleigh, NC (US); Linda K. Hanley-Bowdoin, Raleigh, NC (US); Wei Shen, Morrisville, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/688,976

(22) PCT Filed: Sep. 6, 2022

(86) PCT No.: PCT/US2022/075981
§ 371 (c)(1),
(2) Date: Mar. 4, 2024

(87) PCT Pub. No.: WO2023/035011
PCT Pub. Date: Mar. 9, 2023

(65) Prior Publication Data
US 2024/0271156 A1    Aug. 15, 2024

Related U.S. Application Data

(60) Provisional application No. 63/240,724, filed on Sep. 3, 2021.

(51) Int. Cl.
*C12N 15/82* (2006.01)
(52) U.S. Cl.
CPC .............................. *C12N 15/8283* (2013.01)
(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 4,945,050 A | 7/1990 | Sanford et al. | |
| 5,591,616 A | 1/1997 | Hiei et al. | |
| 5,932,782 A | 8/1999 | Bidney | |
| 5,981,184 A | 11/1999 | Melchers | |
| 6,140,075 A * | 10/2000 | Russell | C07K 16/30 536/23.6 |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,689,558 B2 | 2/2004 | Case | |
| 7,067,317 B2 | 6/2006 | Rebar et al. | |
| 7,262,054 B2 | 8/2007 | Jamieson et al. | |
| 7,732,667 B2 | 6/2010 | Nguyen et al. | |
| 7,888,121 B2 | 2/2011 | Urnov et al. | |
| 7,914,796 B2 | 3/2011 | Miller et al. | |
| 7,951,925 B2 | 5/2011 | Ando et al. | |
| 7,972,854 B2 | 7/2011 | Miller et al. | |
| 8,110,379 B2 | 2/2012 | Dekelver et al. | |
| 8,409,861 B2 | 4/2013 | Guschin et al. | |
| 8,586,526 B2 | 11/2013 | Gregory et al. | |
| 8,766,035 B2 | 7/2014 | Kerns et al. | |
| 8,945,868 B2 | 2/2015 | Collingwood et al. | |
| 8,956,828 B2 | 2/2015 | Bonini et al. | |
| 9,005,973 B2 | 4/2015 | Cost et al. | |
| 9,045,763 B2 | 6/2015 | Dekelver et al. | |
| 9,745,600 B2 | 8/2017 | Donohoue et al. | |
| 10,557,146 B2 | 2/2020 | Gao et al. | |
| 10,662,437 B2 | 5/2020 | Mahfouz et al. | |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2006/0063231 A1 | 3/2006 | Li et al. | |
| 2008/0159996 A1 | 7/2008 | Ando et al. | |
| 2010/0218264 A1 | 8/2010 | Cui et al. | |
| 2011/0265198 A1 | 10/2011 | Gregory et al. | |
| 2012/0017290 A1 | 1/2012 | Cui et al. | |
| 2013/0122591 A1 | 5/2013 | Cost et al. | |
| 2013/0137104 A1 | 5/2013 | Cost et al. | |
| 2013/0177960 A1 | 7/2013 | Rebar | |

(Continued)

FOREIGN PATENT DOCUMENTS

| | | | |
|---|---|---|---|
| WO | WO2008/034648 A1 | 3/2008 | |
| WO | WO2023/035011 A1 | 3/2023 | |

OTHER PUBLICATIONS

Reyes et al The Plant Journal 92:796-807 (Year: 2017).*
Blair, M.W., et al., "Geminivirus resistance breeding in common bean", CAB Reviews: Perspectives in Agriculture, Veterinary Science, Nutrition and Natural Resources , vol. 03, No. 089, 2008, pp. 1-15.
Zaidi, S,S., et al., "Molecular insight into cotton leaf curl geminivirus disease resistance in cultivated cotton (*Gossypium hirsutum*)", in Plant Biotechnology Journal, vol. 18, (2020) pp. 691-706.
"UNIPRT ADP-ribosyl-cyclase/cyclic ADP-ribose hydrolase", Uniprot Accession F4I9F1, Last updated on Jun. 28, 2011, Retrieved from the Internet URL: https://www.uniprot.org/uniprotkb/F4I9F1/entry, accessed on Nov. 6, 2022 pp. 7.
International Search Report and Written Opinion received in PCT Application No. PCT/US2022/075981 mailed on Dec. 8, 2022, pp. 10.

(Continued)

*Primary Examiner* — Brent T Page
(74) *Attorney, Agent, or Firm* — Jenkins, Taylor & Hunt, P.A.

(57) ABSTRACT

Provided are expression cassettes that can be used to express proteins in plants. In some embodiments, the expression cassettes include polynucleotides that encode polypeptides that are at least 96% identical to SEQ ID NO: 2 operably linked to a promoter and a transcription terminator and optionally a tag sequence. Also provided are recombinant vectors, cells, and transgenic plants, progeny, and seeds that include the presently disclosed expression cassettes, and methods for using the disclosed expression cassettes to alter geminivirus resistance and suppress virus-induced leaf chlorosis, leaf curling, or both in plants.

20 Claims, 12 Drawing Sheets
Specification includes a Sequence Listing.

(56) References Cited

U.S. PATENT DOCUMENTS

| | | |
|---|---|---|
| 2013/0177983 A1 | 7/2013 | Rebar |
| 2015/0056705 A1 | 2/2015 | Conway et al. |
| 2015/0067922 A1 | 3/2015 | Yang et al. |
| 2017/0114351 A1 | 4/2017 | Mahfouz et al. |
| 2017/0166912 A1 | 6/2017 | Brower-Toland et al. |
| 2018/0073035 A1 | 3/2018 | Gao et al. |
| 2018/0127765 A1 | 5/2018 | Li |
| 2021/0017529 A1 | 1/2021 | Engelen et al. |

OTHER PUBLICATIONS

Altschul S.F., et al., "Basic Local Alignment Search Tool", Journal of Molecular Biology, 1990, vol. 215, pp. 403-410.

Aragao F.J.L., et al., "Inheritance of foreign genes in transgenic bean (Phaseolus vulgaris L.) cotransformed via particle bombardment" Theoretical and Applied Genetics, vol. 93, 1996, pp. 142-150.

Aragao F.J.L., et al., "Particle bombardment-mediated transient expression of a Brazil nut methionine-rich albumin in bean (Phaseolus vulgaris .)", Plant Molecular Biology, vol. 20, 1992, pp. 357-359.

Barany G., et al., "Kinetics and mechanism of the thiolytic removal of the dithiasuccinoyl (Dts) amino protecting group", Journal of the American Chemical Society, vol. 102, No. 9, 1980, pp. 3084-3095.

Batzer M.A., et al., "Enhanced evolutionary PCR using oligonucleotides with inosine at the 3'-terminus", Nucleic Acids Research, vol. 19, 1991, p. 5081.

Beam K., et al., (2020) "Geminivirus Resistance: A Minireview", Front Plant Sci vol. 11, Article. 1131, Jul. 23, 2020, pp. 1-9.

Cana-Quijada., et al., "Cutting-edge technology to generate plant immunity against geminiviruses", in Current Opinion in Virology, Vo. 42, 2020, pp. 58-64.

Christou P., et al., "Stable transformation of soybean by electroporation and root formation from transformed callus", Proc Natl Acad Sci U S A, vol. 84, Jun. 1987, pp. 3962-3966.

Deshayes A., et al., "Liposome-mediated transformation of tobacco mesophyll protoplasts by an Escherichia coli plasmid", The EMBO Journal, vol. 4, No. 11, 1985, pp. 2731-2737.

Dinant S., et al., "Coat protein gene-mediated protection in Lactuca sativa against lettuce mosaic potyvirus strains", Molecular Breeding, vol. 3, 1997, pp. 75-86.

Draper J., et al., "Ti Plasmid Homologous Sequences Present in Tissues from Agrobacterium Plasmid-transformed Petunia Protoplasts", Plant and Cell Physiology, vol. 23, No. 3, 1982, pp. 451-458.

D'Halluin K., et al., "Transgenic maize plants by tissue electroporation", Plant Cell, vol. 4, Dec. 1992, pp. 1495-1505.

Fiallo-Olivé., et al., "ICTV Virus Taxonomy Profile: Geminiviridae 2021", in Journal of General Virology, vol. 102, 2021, pp. 1-2.

Goff S.A., et al., (2002) "A Draft Sequence of the Rice Genome (Oryza sativa L ssp japonica)", Science, vol. 296, pp. 92-100.

Gray D.J., et al., Simplified construction and performance of a device for particle bombardment. Plant Cell Tissue and Organ Culture, vol. 37,1994, pp. 179-184.

Hain R., et al., "Uptake, integration, expression and genetic transmission of a selectable chimaeric gene by plant protoplasts", Molecular Genetics and Genomics, vol. 199, 1985, pp. 161-168.

Hanley-Bowdoin L., et al., "Gemini viruses: models for plant DNA replication, transcription, and cell cycle regulation", Critical Reviews in Plant Sciences, vol. 18, No. 1, 1999, pp. 71-106.

Henikoff S., et al., "Amino Acid Substitution Matrices from Protein Blocks", Proc Natl Acad Sci U S A, vol. 89, Nov. 1992, pp. 10915-10919.

Hiei Y., et al., "Efficient transformation of rice (Oryza sativa L.) mediated by Agrobacterium and sequence analysis of the boundaries of the T-DNA", The Plant Journal, vol. 6, No. 2, 1994, pp. 271-282.

Horsch R.B., et al., "A simple and general method for transferring genes into plants", Science, vol. 227, No., No. 4691, Mar. 8, 1985, pp. 1229-1231.

International Preliminary Report on Patentability received in PCT Application No. PCT/US2022/075981, mailed on Mar. 5, 2024, 4 Pages.

Jefferson R.A., et al., "GUS fusions: beta-glucuronidase as a sensitive and versatile gene fusion marker in higher plants", The EMBO Journal, vol. 6, No. 13, 1987, pp. 3901-3907.

Kado C.I., et al., "Molecular mechanisms of crown gall tumorigenesis", Critical Reviews in Plant Sciences, vol. 10, No. 1, 1991, pp. 1-32.

Karlin S., et al., "Applications and statistics for multiple high-scoring segments in molecular sequences", Proc Natl Acad Sci U S A, vol. 90, No. 12, Jun. 1993, pp. 5873-5877.

Kim J.W., et al., "Transformation and regeneration of French bean plants by the particle bombardment process", Plant Science, vol. 117, 1996, pp. 131-138.

Klein T, M., et al., "Transformation of Microbes, Plants and Animals by Particle Bombardment," Bio Technology, vol. 10, pp. 286-291, Mar. 1, 1992.

Klein T.M., et al., "Factors Influencing Gene Delivery into Zea mays Cells by High-Velocity Microprojectiles", Biotechnology, vol. 6, May 1988, pp. 559-563.

Kyte J., et al., "A Simple Method for Displaying the Hydropathic Character of a Protein", Journal of Molecular Biology, vol. 157, 1982, pp. 105-132.

Lazarowitz S.G., et al., "Gemini viruses: Genome structure and gene function", Critical Reviews in Plant Sciences, vol. 11, No. 4, 1992, pp. 327-349.

Merrifield R.B., "Solid Phase Peptide Synthesis. I. The Synthesis of a Tetrapeptide", Journal of the American Chemical Society, vol. 85, 1963, pp. 2149-2154.

Moloney M.M., et al., "High efficiency transformation of Brassica napus using Agrobacterium vectors", Plant Cell Reports, vol. 8, 1989, pp. 238-242.

Needleman S.B., "A general method applicable to the search for similarities in the amino acid sequence of two proteins", Journal of Molecular Biology, vol. 48, 1970, pp. 443-453.

Ohtsuka E., et al., "An alternative approach to deoxyoligonucleotides as hybridization probes by insertion of deoxyinosine at ambiguous codon positions", Journal of Biological Chemistry, vol. 260, No. 5, Mar. 10, 1985, pp. 2605-2608.

Pearson W.R., et al., "Improved tools for biological sequence comparison", Proc Natl Acad Sci USA, vol. 85, No. 8, Apr. 15, 1988, pp. 2444-2448.

Reyes M.I., et al., "A VIGS screen identifies immunity in the Arabidopsis Pla-1 accession to viruses in two different genera of the Geminiviridae", The Plant Journal, vol. 92, 2017, pp. 796-807.

Rossolini G.M., et al., "Use of deoxyinosine-containing primers vs degenerate primers for polymerase chain reaction based on ambiguous sequence information", Molecular and Cellular Probes, vol. 8, 1994, pp. 91-98.

Russell D.R., et all., "Stable transformation of Phaseolus vulgaris via electric-discharge mediated particle acceleration", Plant Cell Report, vol. 12, 1993, pp. 165-169.

Sanford J.C., et al., "Delivery of substances into cells and tissues using a particle bombardment process", Particulate Science and Technology, vol. 5, 1987, pp. 27-37.

Sanford J.C., "Biolistic plant transformation", Physiologia Plantarum, vol. 79, No. 1, 1990, pp. 206-209.

Sanford J.C., "The biolistic process", Trends in Biotechnology, vol. 6, No. 12, pp. 299-302, Dec. 1988.

Schultz et al., "DNA tagging in Arabidopsis thaliana. Cloning by gene disruption", in Plant Molecular Biology Manual, 2nd edition, Gelvin et al. (eds.) Kluwer Academic Publishers, New York, New York, United States of America., 1998.

Smith, T. F., et al., "Identification of common molecular subsequences", Advances in Applied Mathematics, vol. 2, 1981, p. 482.

Southern J.A., et al., "Identification of an epitope on the P and V proteins of simian virus 5 that distinguishes between two isolates with different biological characteristics", Journal of General Virology, vol. 72, 1991, pp. 1551-1557.

Spencer T.M., et al., (1994) "Production of fertile transgenic maize by electroporation of suspension culture cells", Plant Molecular Biology, vol. 24, 1994, pp. 51-61.

(56) References Cited

OTHER PUBLICATIONS

Swarts D.C., et al., "DNA-guided DNA interference by a prokaryotic Argonaute", Nature, vol. 507, No. 7491, Mar. 2014, pp. 258-261.
Timmermans M.C.P., et al., "Geminiviruses and Their Uses as Extrachromosomal Replicons", Annual review of plant physiology, vol. 45, 1994, pp. 79-112.
Valles M.P., et al., "Agrobacterium-mediated transformation of commercial melon (*Cucumis melo* L., cv. *Amarillo oro*)", Plant Cell Reports, vol. 13, 1993, pp. 145-148.
Womble D.D., "GCG: The Wisconsin Package of sequence analysis programs", Methods in Molecular Biology, vol. 132, 2000, pp. 3-22.
Zerbini,I,F.M ., et al., "ICTV Virus Taxonomy Profile: Geminiviridae", in Journal of General Virology, vol. 98, 2017, pp. 131-133.
Zhang L-J., et al., "Efficient transformation of tobacco by ultrasonication", BioTechnology, vol. 9, 1991, pp. 996-997.

\* cited by examiner

33 candidate resistance genes for GRP-1/2

- AT1G31540 (NLR) and AT1G32230 (RCD1)
  - NLR (TIR-NBS-LRR class)
  - RCD1 (Responds to stresses, mRNA is mobile)
  - More highly expressed in CaLCuV –infected Pla-1 than in Col-0
  - Polymorphisms in protein sequences } Strategy: Overexpression in Col-0

- 21 genes upregulated in Pla-1 and by CaLCuV infection
- 26 genes with polymorphisms in protein sequences
- 14 genes common to both groups } VIGS in Pla-1

*FIG. 4*

- T₂ plants, segregating Kan-R transgenic lines
- Resistance is dose responsive

ISOFORMS

MASSSSSHNWLYDVFLSFRGEDVRVTFRSHFLKELDRKLITAFRDNEIERSHSLMPDLEQAIKE
SRIAVVVFS□NYASSSWCLNELLEIVNCNDKIVIPVFYHVDPSQVRHQIGDFGKIFENTCKRQT TIR
DEEVKNQWKKALTLVANMLGFDSAKWNDEAKMIEETANDVLGKLLLTTPKDSEELVGIEDHIAE
MSLLIQLESEEVRMVGISGSSGIGKTTIARALFKRLSRHFQGSTFIDRAFVSYSRNIYSGANPD
DPNMKLQLQGHFLSEILGKKDIKIDDPAALEERLKHQKVLIIDDLDDIMVLDTLVGQTWFGY NBS
GSRIIVTNDKHFLIAHGIDHIYEVSFPTDVHACQMLCQSAFKQNYAPKGFEDLVVDVVRHAGN
PPLGLNLLGKYLRRRDMEYWMDMLPRLENSLRIDGKIEKILRISYDGLESEDQEIFRHIACLFN
HMEVTTIKSLLADSDVSFALENLADKSLIHVRQGYVVMHRSLQEMGRKIVRIQSIDKPGEREFL
VDPNDIHDILNACTGTQKVLGISLDIRNIRELDVHERAFKGMSNLRFLEIKNFGLKEDGLHLPP
SFDYLPRTLKLLCWPKFPMRCMPFGFRPENLVKLEMQ□SKLHKLWEGV□PLA□CLKEMDLR□S□K
LKVIPDLSEATNLEILNL□FCESLVELPSSIRNLNKLLNLDM□Y□CKSLKILPTGFNLKSLDRL□ LRR
I□HCSKLKTFPKFSTNISVL□NLTNIEDFPSNLHLQNLVEFSISK□ESDEKQWEEEKPLTPEL
AMMLSPTLT□HL□DM□PSLVELPSSFQNLNQLKELIIINCINLETLPTGINLQSLYYL□F□GCSS
QLRSFPEISTNISVLYLDETAIEEVPWWIEKFSNLTEL□MD□CSRLKCVFLHISKLKHI□EALF
RNCGTLTRVELSGYP
SGMEVMKADNIDTASSSLPKVVLSFLDCFNLDPETVLHHQESIFNYMLFTGK□EVPSYFTYRT
TGSSSLTTPLLHVHLSQPFFRERIGALVT□MN□EPVELEVKCEEFKDRFGNNFDYDIYFEV□N□
□Y□M□DDY□□TAILDCRIPLNEDNAALAQPNYYDHVDIKIEQLEE□ERYGDIEQWGIRLLEDCSS
AETRLDNSNSTLPHVSEAEEGNIGYTPLQGLVNEIEHSEEPGDINVETERSTKRMRLYHFI

Unusual integrated domain (UID)

AA unique to Pia-1

SEQUENCE LISTING

```
Sequence total quantity: 38
SEQ ID NO: 1            moltype = DNA  length = 3495
FEATURE                 Location/Qualifiers
source                  1..3495
                        mol_type = other DNA
                        organism = Arabidopsis thaliana
SEQUENCE: 1
atggcttctt catcttcttc tcacaattgg ttatatgatg ttttcttgag cttcagaggg   60
gaagacgtcc gcgtaacatt ccgtagccac tttctcaaag agcttgatcg gaaactaatc  120
actgctttca gagacaatga gatcgagaga agccactctc tctggcccga tcttgaacaa  180
gccatcaagg aatccaggat cgctgtggtc gttttctcca taaactacgc ttcatcgagc  240
tggtgtctta acgagttgct ggagattgta aactgcaatg ataaaattgt cataccagtt  300
ttctaccatg tggatccttc acaagtgagg catcaaatcg gcgacttcgg aaagatcttt  360
gaaaatactt gcaagagaca aacagatgag gaagtgaaaa atcaatggaa gaaagcgctg  420
actcttgtag cgaatatgct tggatttgac tctgccaaat ggaacgacga agcaaaaatg  480
attgaagaaa tagccaatga tgttttgggt aaactgcttt taactacacc taaggattct  540
gaggaacttg ttggcatcga agatcacatc gctgaaatga gtttactgct gcaactggaa  600
tctgaagaag tgagaatggt tggtatatcg ggttcctcag ggattggtaa gactaccatt  660
gcaagagctc tgtttaaacg actttctcga catttccaag gtagcacttt catcgacagg  720
gcttttgtat cttatagtcg gaatatttat agtggcgcca atccggacga ccccaatatg  780
aagttgcagc tacaaggaca cttcctatct gaaattctcg gcaaaaagga cataaagata  840
gatgatccag ctgcactgga agagaggcta aagcaccaaa aagttcttat cattattgat  900
gatttggatg atataatggt actagataca ttagtgggtc aaactcaatg gtttggatat  960
gggagcagaa tcattgtggt tacaaatgat aagcacttct tgattgctca tggaattgat 1020
catatttatg aagtaagttt cccaactgat gtgcatgctt gtcagatgtt atgtcaatct 1080
gcattcaagc aaaactatgc tcctaaaggt tttgaggatc ttgtagttga tgtagtaaga 1140
catgcgggca attttccttt gggtcttaat cttttgggta aatatttgcg gaggagggat 1200
```

```
atggaatact ggatggatat gctgccaagg cttgagaata gtctacgtat agacggtaaa   1260
attgaaaaaa tactaagaat cagctatgat gggttagaga gtgaagatca agagatattt   1320
cgtcatatcg catgtctttt caatcatatg gaagtcacaa ccatcaagtc cttgctggca   1380
gatagtgatg ttagttttgc actagaaaac ctagctgata agtcccttat tcatgtcaga   1440
caaggttatg tggtgatgca ccgttcgcta caagaaatgg gtagaaaaat tgttcgcatt   1500
cagtccattg acaaacctgg agaacgagaa tttctggtgg atccaaatga tatacatgat   1560
atactcaatg catgcactgg tactcaaaag gttttaggta tatcactgga tataaggaat   1620
attcgtgagt ggatgtacat ggagagggcc ttcaaaggga tgtctaatct ccgtttctta   1680
gaaattaaga actttggttt gaaagaagac ggtttgcatt tacctccaag tttcgactat   1740
ttgccccgta cactcaaact attgtgctgc cccaaatttc caatgaggtg tatgccttt t  1800
ggttttcgtc ctgaaaacct tgtcaagctc gaaatgcagt gcagcaagct acataagcta   1860
tgggaagtag ttgtgccact tgcatgtcta aggaaatgga tctgcgcgt atcattaaag    1920
ctgaaagtaa ttccagatct ttctgaagct actaatctcg agatacttaa tctttcgttt   1980
tgcgagagtt tggtcgagct cccatcctct atacgaaatc tcaataaact gttgaacttg   2040
gacatgttct actgcaaaag tctgaaaatt cttcctaccg gattcaacct caaatctctt   2100
gaccgcctcc atctcgatca ttgctcaaag ttgaagactt tcccaaatt ctcaaccaac    2160
atctcagttc tcagtctaaa tctaacaaac attgaagatt ccccttctaa tttacatctc   2220
cagaatcttg ttgagtttag catatcaaaa gacgagagtg atgagaaaca atgggaagaa   2280
gagaagccgc ttacgccctt cctggcgatg atgttgtctc ccactttgac gatcttgcat   2340
ctctgtgata tgccaagttt ggtggagctt ccttcctcat tcagaatct caatcaactg    2400
aaggagttga tcataataaa ctgcataaat ctggagactc tgcccaccgg aatcaacctc   2460
caatctctct attaccttag tttcagagga tgctcacagt tgaggagctt tcctgaaatc   2520
tcaaccaaca tctcagtgct ctatctagac gaaacagcga ttgaagaggt tccttggtgg   2580
atcgagaaat tctctaacct cactgagcta agaatggaca ggtgcagcag gctaaaatgt   2640
gtgttcctac acatttctaa actgaaacat cttcaggaag ctttgtttcg aaattgtggt   2700
acattgacca gagttgaatt gagtggatat ccaagtggga tttgaggtgat gaaagcagac    2760
aatattgaca cagcctcctc ttctcttcct aaagtcgtac tcagtttctt ggactgcttc   2820
aacttggatc cagaaactgt ccttcatcac caagaatcaa ttattttcaa ctacatgtta   2880
tttacaggga aggagaagt gccatcatat ttcacttacc gtactactgg aagctcctct    2940
ctgaccattc ctctacttca cgtccatctc tcccaaccat tcttcagatt taggattggg   3000
gcattggtaa ctatagttaa tacggaggag ccagtagagc tcgaggtaaa atgtgagttc   3060
aaagacagat ttgggaacaa ctttgattat gacatttatt tcgaagttta taatcaaaac   3120
tattgtgtgg aggatgacta tattatagct atattggact gtcgtatccc tctaaacgaa   3180
gataatgctg ctctagctca accgaactac tacgatcatg tggatataaa gattgagcaa   3240
ttagaggaag aggaaagata tggtgatatt gaacaatgga gtatacgact cttagaggac   3300
tgttcatcag cggagactcg acttgataat tcaaacagta ctcttccaca tgtttctgaa   3360
gccgaagaag gcaatatagg gtatacacct cttcaaggac ttgttaatga gattgaacac   3420
agtgaagagc ctggagatat caatgtagaa actgagagaa gcacgaagcg catgcggcta   3480
tatcacttca tataa                                                   3495

SEQ ID NO: 2             moltype = AA  length = 1164
FEATURE                  Location/Qualifiers
source                   1..1164
                         mol_type = protein
                         organism = Arabidopsis thaliana
SEQUENCE: 2
MASSSSSHNW LYDVFLSFRG EDVRVTFRSH FLKELDRKLI TAFRDNEIER SHSLWPDLEQ    60
AIKESRIAVV VFSINYASSS WCLNELLEIV NCNDKIVIPV FYHVDPSQVR HQIGDFGKIF   120
ENTCKRQTDE EVKNQWKKAL TLVANMLGFD SAKWNDEAKM IEEIANDVLG KLLLTTPKDS   180
EELVGIEDHI AEMSLLLQLE SEEVRMVGIS GSSGIGKTTI ARALFKRLSR HFQGSTFIDR   240
APFVSYSRNIY SGANPDDPNM KLQLQGHFLS EILGKKDIKI DDPAALEERL KHQKVLIIID   300
DLDDIMVLDT LVGQTQWFGY GSRIIVVTND KHFLIAHGID HIYEVSFPTD VHACQMLCQS   360
APKQNYAPKG FEDLVVDVVR HAGNFPLGLN LLGKYLRRRD MEYWMDMLPR LENSLRIDGK   420
IEKILRISYD GLESEDQEIF RHIACLFNHM EVTTIKSLLA DSDVSFALEN LADKSLIHVR   480
QGYVVMHRSL QEMGRKIVRI QSIDKPGERE FLVDPNDIHD ILNACTGTQK VLGISLDIRN   540
IRELDVHERA FKGMSNLRFL EIKNFGLKED GLHLPPSFDY LPRTLKLLCW PKFPMRCMPF   600
GFRPENLVKL EMQCSKLHKL WEGVVPLACL KEMDLRVSLK LKVIPDLSEA TNLEILNLSF   660
CESLVELPSS IRNLNKLLNL DMFYCKSLKI LPTGFNLKSL DRLHLDHCSK LKTFPKFSTN   720
ISVLSLNLTN IEDFPSNLHL QNLVEFSISK DESDEKQWEE EKPLTPFLAM MLSPTLTILH   780
LCDMPSLVEL PSSFQNLNQL KELIIINCIN LETLPTGINL QSLYYLSFRG CSQLRSFPEI   840
STNISVLYLD ETAIEEVPWW IEKFSNLTEL RMDRCSRLKC VFLHISKLKH LQEALFRNCG   900
TLTRVELSGY PSGMEVMKAD NIDTASSSLP KVVLSFLDCF NLDPETVLHH QESIIFNYML   960
FTGKGEVPSY FTYRTTGSSS LTIPLLHVHL SQPFFRFRIG ALVTIVNTEE PVELEVKCEF  1020
KDRFGNNFDY DIYFEVYNQN YCVEDDYIIA ILDCRIPLNE DNAALAQPNY YDHVDIKIEQ  1080
LEEEERYGDI EQWGIRLLED CSSAETRLDN SNSTLPHVSE AEEGNIGYTP LQGLVNEIEH  1140
SEEPGDINVE TERSTKRMRL YHFI                                        1164

SEQ ID NO: 3             moltype = DNA  length = 2331
FEATURE                  Location/Qualifiers
source                   1..2331
                         mol_type = other DNA
                         organism = Arabidopsis thaliana
SEQUENCE: 3
atggcttctt catcttcttc tcacaattgg ttatatgatg ttttcttgag cttcagaggg    60
gaagacgtcc gcgtaacatt ccgtagccac tttctcaaag agcttgatcg gaaactaatc   120
actgctttca gagacaatga gatcgagaga agccactctc tctggcccga tcttgaacaa   180
gccatcaagg aatccaggat cgctgtggtc gtttttctcca taaactacgc ttcatcgagc   240
tggtgtctta acgagttgct ggagattgta aactgcaatg ataaaattgt cataccagtt   300
ttctaccatg tggatccttc acaagtgagg catcaaatcg gcgacttcgg aaagatcttt   360
```

```
gaaaatactt gcaagagaca aacagatgag gaagtgaaaa atcaatgaaa gaaagcgctg    420
actcttgtag cgaatatgct tggatttgac tctgccaaat ggaacgacga agcaaaaatg    480
attgaagaaa tagccaatga tgttttgggt aaactgcttt taactacacc taaggattct    540
gaggaacttg ttggcatcga agatcacatc gctgaaatga gtttactgct gcaactggaa    600
tctgaagaag tgagaatggt tggtatatcg ggttcctcag ggattggtaa gactaccatt    660
gcaagagctc tgtttaaacg actttctcga catttccaag gtagcacttt catcgacagg    720
gcttttgtat cttatagtcg gaatatttat agtggcgcca atccgacga ccccaatatg    780
aagttgcagc tacaaggaca cttcctatct gaaattctcg gcaaaaagga cataaagata    840
gatgatccag ctgcactgga agagaggcta aagcaccaaa aagttcttat cattattgat    900
gatttggatg atataatggt actagataca ttagtgggtc aaactcaatg gtttggatat    960
gggagcagaa tcattgtggt tacaaatgat aagcacttct tgattgctca tggaattgat   1020
catatttatg aagtaagttt cccaactgat gtgcatgctt gtcagatgtt atgtcaatct   1080
gcattcaagc aaaactatgc tcctaaaggt tttgaggatc ttgtagttga tgtagtaaga   1140
catgcgggca atttccttt gggtcttaat cttttggata aatatttgcg gaggagggat   1200
atggaatact ggatggatat gctgccaagg cttgagaata gtctacgtat agacggtaaa   1260
attgaaaaaa tactaagaat cagctatgat gggttagaga gtgaagatca agagatattt   1320
cgtcatatcg catgtctttt caatcatatg gaagtcacaa ccatcaagtc cttgctggca   1380
gatagtgatg ttagttttgc actagaaaac ctagctgata gtcccttat tcatgtcgaa   1440
caaggttatg tggtgatgca ccgttcgcta caagaaatgg gtagaaaaat tgttcgcatt   1500
cagtccattg acaaacctgg agaacgagaa tttctggtgg atccaaatga tacatgat    1560
atactcaatg catgcactgg tactcaaaag gttttaggta tatcactgga tataaggaat   1620
attcgtgagt tggatgtaca tgagagggcc ttcaaaggga tgtctaatct ccgtttctta   1680
gaaattaaga actttggttt gaagaagac ggtttgcatt tacctccaag tttcgactat   1740
ttgccccgta cactcaaact attgtgctgg cccaaatttc caatgaggtg tatgcctttt   1800
ggttttcgtc ctgaaaacct tgtcaagctc gaaatgcagt gcagcaagct acataagcta   1860
tgggaaggag ttgtgccaat tgcatgtcta aaggaaatgg atctgcgcgt atcattaaag   1920
ctgaaagtaa ttccagatct ttctgaagct actaatctcg agatacttaa tctttcgttt   1980
tgcgagagtt tggtcgagct cccatcctct atacgaaatc tcaataaact gttgaacttg   2040
gacatgttct actgcaaaag tctgaaaatt cttcctaccg gattcaacct caaatctctt   2100
gaccgcctcc atctcgatca ttgctcaaag ttgaagactt ttcccaaatt ctcaaccaac   2160
atctcagttc tcagtctaaa tctaacaaac attgaagatt tcccttctaa tttacatctc   2220
cagaatcttg ttgagtttag catatcaaaa gacgagagtg atgagaaaca atgggaagaa   2280
gagaaggtaa gtagttctaa acttaacatt atctccaaac tctttcccta a             2331

SEQ ID NO: 4           moltype = AA  length = 776
FEATURE                Location/Qualifiers
source                 1..776
                       mol_type = protein
                       organism = Arabidopsis thaliana
SEQUENCE: 4
MASSSSSHNW LYDVFLSFRG EDVRVTFRSH FLKELDRKLI TAFRDNEIER SHSLWPDLEQ     60
AIKESRIAVV VFSINYASSS WCLNELLEIV NCNDKIVIPV FYHVDPSQVR HQIGDFGKIF    120
ENTCKRQTDE EVKNQWKKAL TLVANMLGFD SAKWNDEAKM IEEIANDVLG KLLLTTPKDS    180
EELVGIEDHI AEMSLLLQLE SEEVRMVGIS GSSGIGKTTI ARALFKRLSR HFQGSTFIDR    240
AFVSYSRNIY SGANPDDPNM KLQLQGHFLS EILGKKDIKI DDPAALEERL KHQKVLIIID    300
DLDDIMVLDT LVGQTQWFGY GSRIIVVTND KHFLIAHGID HIYEVSFPTD VHACQMLCQS    360
AFKQNYAPKG FEDLVVDVVR HAGNFPLGLN LLGKYLRRRD MEYWMDMLPR LENSLRIDGK    420
IEKILRISYD GLESEDQEIF RHIACLFNHM EVTTIKSLLA DSDVSFALEN LADKSLIHVR    480
QGYVVMHRSL QEMGRKIVRI QSIDKPGERE FLVDPNDIHD ILNACTGTQK VLGISLDIRN    540
IRELDVHERA FKGMSNLRFL EIKNFGLKED GHLPPSFDY LPRTLKLLCW PKFPMRCMPF     600
GFRPENLVKL EMQCSKLHKL WEGVVPLACL KEMDLRVSLK LKVIPDLSEA TNLEILNLSF    660
CESLVELPSS IRNLKLLNL DMFYCKSLKI LPTGFNLKSL DRLHLDHCSK LKTFPKFSTN     720
ISVLSLNLTN IEDFPSNLHL QNLVEFSISK DESDEKQWEE EKVSSSKLNI ISKLFS        776

SEQ ID NO: 5           moltype = DNA  length = 7532
FEATURE                Location/Qualifiers
source                 1..7532
                       mol_type = genomic DNA
                       organism = Arabidopsis thaliana
SEQUENCE: 5
agaattccta agacccagtt ggaggactaa tgacattgcc acacatataa caaaagagac     60
ggtaaaacat gattcaattg attaataaaa taaaagtttt agaaatcttc tcctatttga    120
taaaaatgat ggattcttct tccaaggtg tttacaatga agaaaaaatg ttgagtgtta     180
aaagtagatt tctagagatc tttaatctaa atgtatatat attttggaat atggtccggt    240
tacatggata gtatgttaag attgttagac tattgtaat atgtagattt atttatttaa    300
atactttcat ttgggacaaa actaaaatta caggttgtgg ggtttgggaa attacgagtt    360
atggtacagc gttcattgaa ttcaacgatc ttgcagagaa tacttcagta tccttccagc    420
tggacacacg ttttcaggta accccaaaat ctcatacacc agtggcttat tttagtttta    480
caccaattgc gataatgtaa tgacttagtc tcttcatagt caaatctctt gttgtttagc    540
atatgattcg aacttctttt gtagaaaata tatagactgc aataacgcag cttttactct    600
attttcagtc tattatattg ttcagcaagt ggttgatagt atcaacgtga tacttattac    660
ttaatagagt tccaacatga atacagattc agaaccaaga ctaagcaatg catgattat    720
tttatttttg attaaataaa tcttaaaaaa atagcatcaa aattagatta tctttgttca    780
tgttgacaat actttactaa aagtcctgt taacacaat aagtccttgt ttaaaatgtt     840
tgtcttatta gttctaatag gtaaaatgtg taaagaaacc atcaccttt ccaaaaacat     900
gtaaaacacc gtcaactatt tttgtgggtt ttaagctctc cacctttttt aaaatggtaa    960
aataacacct atgattatta aattaattta aaataagaca aaataaatat aaataataaa   1020
agtaatttgg tttaagattt attttcctaa aatttcaaaa gttagaacaa atttgaacaa   1080
aaataaaatt aaatatgcta agctataaac tagttttagt ttacataacg atttgtaatg   1140
```

```
gcaatgaaac ttacttttta tatcgcaaaa aaccaacaac taaatactgg aaaagaaatc  1200
gaactcgaat ttgaaataga taaatacaaa ataaattgtt ttatttatgt ttcaaaataa  1260
tagtttattt gatatttatt tggtttgata atattagatg ttatattacc attttttaaa  1320
aggtgagggt ttaaatacca aaagaaaagt tgacggtttt ttacatgtta ttggataaag  1380
gagaggtttt ttttacccat tttccgttct aatataatga ttattttttgc tatttctcac  1440
agtaaactca tgttgcccat aatgtgagag tacttctcca caaatcctct cctttgcata  1500
aaatgagaag cacatctact ggatttggag tatgatgagc tatacatatt tattaagaat  1560
atgtaaatga atgagatagt aatgtaaaga caagaggcta tgaaagatgg ttgtgaccac  1620
tgagtcaaca aagaggaaac ttccgccaag ttgcatcaga aaagtctaag aaatgattgc  1680
gaaaacttgt gtggccgtga ttaagtcaag ttacctctca gctgttatgt taaatgtttt  1740
atatccacca agacagactc actacttctc ctctatttct cttcttaaaa gtcttcgttc  1800
cttgtttcct ccttctaact ctctctctct ctatggcttc ttcatcttct tctcacaatt  1860
ggttatatga tgttttcttg agcttcagag gggaagacgt ccgcgtaaca ttccgtagcc  1920
actttctcaa agagcttgat cggaaactaa tcactgcttc aagacaat gagatcgaga  1980
gaagccactc tctctggccc gatcttgaac aagccatcaa ggaatccagg atcgctgtgg  2040
tcgtttctc cataaactac gcttcatcga gctggtgtct taacgagttg ctggagattg  2100
taaactgcaa tgataaaatt gtcataccag ttttctacca tgtggatcct tcacaagtga  2160
ggcatcaaat cggcgacttc ggaaagatct ttgaaaatac ttgcaagaga caaacagatg  2220
aggaagtgaa aaatcaatgg aagaaagcgc tgactcttgt agcgaatatg cttggatttg  2280
actctgccaa atggtatgtt tttttttaat tattagatac atcttgaaat aaattgttgt  2340
ttcatatttg ttaaattatc tttcatctta ttaggaacga cgaagcaaaa atgattgaag  2400
aaatagccaa tgatgttttg ggtaaactgc ttttaactac acctaaggat tctgaggaac  2460
ttgttggcat cgaagatcac atcgctgaaa tgagtttact gctgcaactg gaatctgaag  2520
aagtgagaat ggttggtata tcgggttcct cagggattgg taagactacc attgcaagag  2580
ctctgtttaa acgactttct cgacatttcc aaggtagcac tttcatcgac agggcttttg  2640
tatcttatag tcggaatatt tatagtggcg ccaatccgga cgaccccaat atgaagttgc  2700
agctacaagg acacttccta tctgaaattc tcggcaaaaa ggacataaag atagatgatc  2760
cagctgcact ggaagagagg ctaaagcacc aaaaagttct tatcattatt gatgatttgg  2820
atgatataat ggtactagat acattagtgg gtcaaactca atggtttgga tatgggagca  2880
gaatcattgt ggttacaaat gataagcact tcttgattgc tcatgaatt gatcatattt  2940
atgaagtaag tttcccaact gatgtgcatg cttgtcagat gttatgtcaa tctgcattca  3000
agcaaaacta tgctcctaaa ggttttgagg atcttgtagt tgatgtagta agacatgcgg  3060
gcaatttttcc tttgggtctt aatcttttgg gtaaatattt gcggaggagg gatatggaat  3120
actggatgga tatgctgcca aggcttgaga atagtctacg tatagacgat aaaattgaaa  3180
aaatactaag aatcagctat gatgggttag agagtgaaga tcaagagata tttcgtcata  3240
tcgcatgtct tttcaatcat atggaagtca caaccatcaa gtccttgctg cagatagtg  3300
atgttagttt tgcactagaa aacctagctg ataagtccct tattcatgtc agacaaggtt  3360
atgtggtgat gcaccgttcg ctacaagaaa tgggtagaaa aattgttcgc attcagtcca  3420
ttgacaaacc tggagaacga gaatttctgg tggatccaaa tgatatacat gatatactca  3480
atgcatgcac tgtaagtttt aaaaaaatat ttttgatcct ttcataactc aatatacgta  3540
taaggtttaa gagatgccat ctgataaaca atgaattgta tggggttgtc tatttctcat  3600
atatatcata ttttttcaggg tactcaaaag gttttaggta tatcactgga tataaggaat  3660
attcgtgagt tggatgtaca tgagagggcc ttcaaaggga tgtctaatct ccgtttctta  3720
gaaattaaga actttggttt gaagaagac ggtttgcatt tacctccaag tttcgactat  3780
ttgccccgta cactcaaact attgtgctgg cccaaatttc caatgaggtg tatgcctttt  3840
ggttttcgtc ctgaaaacct tgtcaagctc gaaatgcagt gcagcaagct acataagcta  3900
tgggaaggag ttgtggtaag ttttgagaat aatttcttat gttgttattt tttttttttt  3960
tatgataata gtgccacgtg atgtgtaatt tctgttgagc tctatgtttg attttttgttg  4020
gatacagcca cttgcatgtc taaaggaaat ggatctgcgc gtatcattaa agctgaaagt  4080
aattccagat ctttctgaag ctactaatct cgagatactt aatctttcgt tttgcgagag  4140
tttggtcgag ctcccatcct ctatacgaaa tctcaataaa ctgttgaact tggacatgtt  4200
ctactgcaaa agtctgaaaa ttcttcctac cggattcaac ctcaaatctc ttgaccgcct  4260
ccatctcgat cattgctcaa agttgaagac ttttcccaaa ttctcaacca acatctcagt  4320
tctcagtcta aatctaacaa acattgaaga tttcccttct aatttacatc tccagaatct  4380
tgttgagttt agcatatcaa aagacgaatg tgatgagaaa caatgggaag aagagaaggt  4440
aagtagttct aaacttaaca ttatctccaa actctttttcc taacacttttt ataaagaaa  4500
agaaaaatca ttgtcgttga ctcaaacttt gtacacttgt atgtgaaaac ttaaaaaaca  4560
ctaattttta tttatttatg aatatttttaa tttgattgga agtaaatttt tggttacaaa  4620
gaatgaagaa gaaaaatatct gattttaaaa ataaataaat aaaaaagtaaa aacagataa  4680
aaatggaaag aaaataagaa attaaagatg atatcaattg ggttttttcc tttgtcgtga  4740
tatcattaaa acgtaaaaga aaattataca tgggatttttc ttaattttatt attttttagct  4800
attttctaat gacatatatt atgtaattaa aaaataacgg ttttaataaa gagtagatgt  4860
gagcgtgaat ggaaagttcc aaacaattat attaatgctg atgagattta cccataatac  4920
attagtactg ttattctttt cgtttttaaa gatttatttt ctaaaattta acttttaaaag  4980
taatttgcca ctgaaaaccc gtaaaacttg ttatttggtt cagccgctta cgcccttcct  5040
ggcgatgatg ttgtctccca ctttgacgat cttgcatctc tgtgatatgc caagtttggt  5100
ggagcttcct tcctcatttc agaatctcaa tcaactgaag gagttgatca taataaactg  5160
cataaatctg ggagactgc ccaccggaat caacctccaa tctctctatt accttagttt  5220
cagaggatgc tcacagttga ggagcttttcc tgaaatctca accaacatct cagtgctcta  5280
tctagacgaa acagcgattg aagaggttcc ttggtggatc gagaaattct ctaacctcac  5340
tgagctaaga atggacaggt gcagcaggct aaaatgtgtg ttcctacaca tttcaaaact  5400
gaaacatctt caggaagctt tgtttcgaaa ttgtggtaca ttgaccagag ttgaattgag  5460
tggatatcca agtgggatgg aggtgatgaa agcagacaat attgacacag cctcctcttc  5520
tcttcctaaa gtcgtactca gtttcttgga ttggatccga aaactgtcct  5580
tcatcaccaa gaatcaatta ttttcaacta catgttattt acaggaaag gagaagtgcc  5640
atcatatttc acttaccgta ctactggaag ctccctctg accattcctc tacttcacgt  5700
ccatctctcc caaccattct tcagatttag gattggcgca ttggtaacta tagttaatac  5760
ggaggagcca gtagagctcg aggtaaaatg tgagttcaaa gacagatttg gaacaacttt  5820
tgattatgac atttatttcg aagtttataa tcaaaactat tgtgtggagg atgactatat  5880
```

```
tatagctata ttggactgtc gtatccctct aaacgaagat aatgctgctc tagctcaacc  5940
gaactactac gatcatgtgg atataaagat tgagcaatta gaggaagagg aaagatatgg  6000
tgatattgaa caatggggta tacgactctt agaggactgt tcatcagcgg agactcgact  6060
tgataattca aacagtactc ttccacatgt ttctgaagcc gaagaaggca atataggta   6120
tacacctctt caaggacttg ttaatgagat tgaacacagt gaagagcctg gagatatcaa  6180
tgtagaaact gagagaagca cgaagcgcat gcgggtaagc attaagcaat aattgaacat  6240
aatgactatt catctctcaa ttcttttgc attattgaca actagattct tttgcagcta   6300
tatcacttca tataagtaat attagggtgt ctacgtccaa actaaacgga tggggtatac  6360
gacacttaga ggactgtcat cagcgaagaa ccgacatggt aatccaaaca ctatgcagca  6420
tgtttgtgaa gctgatgaag gcaatgatgg atgccattag actgatcaga acgaagagcg  6480
aggagacagt gatgaatagt gatataggta gggagagtga tcactttgaa gagtgcgaat  6540
atagtgatat aagcaatgag agtgattaga gtgaagagca tggggatagt gacgatgatg  6600
gtataagcaa tgagactaat ctgttggaag agtgtggaaa cagtgattag gcaatgagct  6660
tgatcagaat gaagacagtt gagatagaga gaaccaatac acaatacaag gtaagtatta  6720
atcaagaact gaacagaata tcagatatct cacagtcagg atctttaata gtatagatca  6780
ctgagttgtt ttcttttact tgcagattac gtgaaaaaga aatgaatctt tgagatactt  6840
ttatggtgat ggaatgagta gttttgctgt cggttctatg gaacaacaag gagagcccaa  6900
gattcttcat tgtcttcagg gcagatgaag atgttgctgt tcatgtgaat gttttaaaat  6960
gttttgtttc ttttcttagg ttgcacgttt gtgataagct tatttcatta ctataacgat  7020
tcctttaatt tgctgtctag cacaaagttt tacagtgaac ccgaattgag tttgtgattt  7080
ataatagttc tcttttttta tgaatagttg aaaagtgtta tgtatagcat acacctatta  7140
tggagagaaa tcgaacgact gacttacttt gtagccaact ctgcaaagtt tttaggcatc  7200
tttcaaagtc cataaaccaa cttagtctat ttccgaatta actatataac acaaattgtt  7260
tcaaatgcaa gtcgtgttgt ggatacaaaa aaactgatgg aattcacgga aactggtata  7320
agattaaaag gatttggtat aagattctct gaagatggta atgtagagag ataattagtt  7380
ggtccaaaaa atattttgc ttgcggccac caaatcccta gggacggctc tggctatatg   7440
gctttgtagc tactccagct acgtaagaaa tgagatcgga taacttcatt aacagaggtt  7500
ttgtagaaga aaatatatct atataacaaa at                                7532

SEQ ID NO: 6           moltype = AA   length = 14
FEATURE                Location/Qualifiers
REGION                 1..14
                       note = Artificially synthesized peptide tag
source                 1..14
                       mol_type = protein
                       organism = synthetic construct
SEQUENCE: 6
GKPIPNPLLG LDST                                                      14

SEQ ID NO: 7           moltype = AA   length = 5
FEATURE                Location/Qualifiers
REGION                 1..5
                       note = Artificially synthesized peptide tag
source                 1..5
                       mol_type = protein
                       organism = synthetic construct
SEQUENCE: 7
FHHTT                                                                 5

SEQ ID NO: 8           moltype = DNA   length = 5422
FEATURE                Location/Qualifiers
source                 1..5422
                       mol_type = genomic DNA
                       organism = Arabidopsis thaliana
SEQUENCE: 8
gttaaatgtt ttatatccac caagacagac tcactactc tcctctattt ctcttcttaa     60
aagtcttcgt tccttgtttc ctccttctaa ctctctctct ctatggcttc gtcatcttct   120
tctcacaatt ggttatatga tgtttcttg agcttcagag gggaagacgt ccgcgtaaca    180
ttccgtagcc actttctcaa agagctttgat cggaaactaa tcactgcttt cagagacaat  240
gagatcgaga gaagccactc tctctggcc gatcttgaac aagccatcaa ggaatccagg    300
atcgctgtgg tcgttttctc aaaaaactac gcttcatcga gctggtgtct taacgagttg   360
ctggagattg taaactgcaa tgataaaatt gtcataccag ttttctacca tgtggatcct   420
tcccaagtga ggcatcaaat cggcgacttc ggaaagatct ttgaaaatac ttgcaagaga   480
caaacagatg aggaagtgaa aaatcaatgg aagaaagcgt tgactcttgt agcgaatatg   540
cttggatttg actctgccaa atggtatgtt tttttatta ttagatacat cttgaaataa    600
attgttgttt catatttgtt aaattatctt tcatcttatt aggaacgacg aagcaaaaat   660
gattgaagaa atagccaatg atgttttggg taaactgctt ttaactacac ccaaggattc   720
tgaggaactt gttggcatcg aagatcacat cgctgaaatg agttacttgc tgcaactgga   780
atctaaagaa gtgagaatgg ttggtatatc gggttcctca gggattggta agactaccat   840
tgcaagagct ctgtttaaac gacttcctct acatttccaa ggtagcactt tcatcgcacg   900
ggcttttgta tcttatagtc ggaatattta gtggcgcc aatccggacg acccaatat     960
gaagttgcag ctacaaggac acttcctatc tgaaattctc gggaaaaaag acataaagat  1020
agatgatcca gctgcattgg aagagggct aaagcaccaa aagttcttta tcattattga   1080
tgatttggat gatataatgg tactagatac attagtgagt caaactccat ggtttggata  1140
tgggagcaga atcattgtgg ttacaaatga taagcacttc ttgattgctc atggaattga  1200
tcatatttat gaagtaagtt tcccaactga tgtgcatgct tgtcagatgt tatgtcaatc  1260
tgcattcaag caaaactatg ctcctaaagg ttttgaggat cttgtagttg atgtagtaag  1320
acatgcgggc aattttcctt tgggtcttaa tctttttggt aaatatttgc ggaggaggga  1380
tatggaatac tggatggata tgctgccaag gcttgagaat agtctacgta tagacggtaa  1440
```

```
aattgaaaaa atactaagaa tcagctatga tgggttagag agtgaagatc aagagatatt    1500
tcgtcatatc gcatgtcttt tcaatcatat ggaagtcaca accatcaagt ccttgctggc    1560
agatagtgat gttagttttg cactagaaaa cctagctgat aagtccctca ttcatgtcag    1620
acaaggttat gtggtgatgc accgttcgct acaagaaatg ggtagaaaaa ttgttcgcat    1680
tcagtccatt gacaaacctg gagaacgaga atttctgtg gatccaaatg atatacatga    1740
tatactcaat gcatgcactg taagtttaaa aaaaatattt ttgatccttt cataactcaa    1800
tatacgtata aggtttaaga gatgccatct gataaacgat gaattgtatg gggttgtcta    1860
tttctcatat atatcatatt tttcagggta ctcaaaaggt tttaggtata tcactggata    1920
taaggaatat tcgtgagttg gatgtacatg agagggcctt caaagggatg tctaatctcc    1980
gtttcttaga aattaagaac tttggtttga aagaagacgg tttgcattta cctccaagtt    2040
tcgactattt gccccgtaca ctcaaactat tgtgctggtc caaatttcca atgaggtgta    2100
tgcctttttgg ttttcgtcct gaaaaccttg tcaagctcga aatgcagtac agcaagctac    2160
ataagctatg ggaaggagtt gcggtaagtt ttgagaataa tttcttatgt tgttattttg    2220
tttttttatg acaatagtgc cacatgatgt gtaattttct ttgagctcta tgtttgattt    2280
ttgttggata cagccactta catgtctaaa ggaaatggat ctgcacggat catcaaacct    2340
gaaagtaatt ccagatcttt ctgaagctac taatctcgag atacttaatc ttaagttttg    2400
cgagagtttg gtcgagctcc cgtcctctat acgaaatctc aataaactgt tgaacttgga    2460
catgctaaac tgcaaaagtc tgaaaattct tcctaccgga ttcaacctca aatctcttga    2520
ccgcctcaat ctctatcatt gctcaaagtt gaagacttt cccaaattct caaccaacat    2580
ctcagttctc aatctaaatc taacaaacat tgaagatttc ccttctaatt tacatctcga    2640
gaatcttgtt gagtttagaa tatcaaaaga agagagtgat gagaaacaat gggaagaaga    2700
gaaggtaagt agttctacac ttaacattat ctccaaactc tttccctaac acttttataa    2760
aagtaaaaaa aaatcattgt cgttgactcg tgtgaaaact taaaaaacac taattttttat    2820
atatttatga ataattaat ttgattggaa agtaaatttt ggttacaaag aatgaagaag    2880
aaaatatctg attttaaaaa aaaataaata aaaagtaaaa aacagataaa aatggaaaga    2940
aaataagaaa ttaaagatga tatcaattgg gtttttttcct ttgtcgtgat atcattaaaa    3000
cgtaaaagaa aattatacat gggattttct taatttatta ttttttagcta ttttctaatg    3060
acatatatta tgtaattaaa aaataatcgg ttttaattaaa gagtagatgt gatcgtgaat    3120
ggaaagttcc aaacaatcta ttaataccga tgagatttac ccataataca ttagtactgt    3180
tattcttttc gttttttaaag atttatttc taaaattaa ctttaaaagt aatttgccac    3240
tgaaaacccg taaaacttgt tatttggttc agccgcttac gcccttcctg gcgatgatgt    3300
tgtctcccac tttgacgagc ttgcatctcg agaatctccc aagtttggtg gagcttactt    3360
cctcatttca gaatctcaat caactgaagg acttgatcat aataaactgc ataaatctgg    3420
agactctgcc caccggaatc aacctccaat ctcttgatta cctttgtttc agtggatgct    3480
cacagttgag gagctttcct gaaatctcaa ccaacatctc agtgctctat ctagacgaaa    3540
cagcgattga agaggttcct tggtggatcg agaaattctc taacctcact gagctaagca    3600
tgaacagttg cagcaggcta aaatgtgtgt tcctacacat gtctaaactg aaacatctta    3660
aggaagcttt gtttcgaaat tgtggtacat tgaccagagt tgaattgagt ggatatccaa    3720
gtgggatgga ggtgatgaaa gcagacaata ttgcacacag ctcctcttct cttcctaaag    3780
tcgtactcag tttcttggac tgcttcaact tggatccaga aactgtcctt catcaccaag    3840
aatcaattat tttcaactac atgttattta cagggaaaga agaagtgcca tcatatttca    3900
cttaccgtac tactggaagc tcctctctga ccattcctat acttcacgtc catctctccc    3960
aaccattctt cagatttagg attggcgcat tggtaactaa taaggaggag ccagtagagc    4020
tcgaggtaaa atgtgagttc aaagacagat ttgggaacaa ctttgattat gacatttatt    4080
tcgaagttaa taaagataga tattatgggg aggattgcta taatatagct atattggact    4140
gtcgtatccc tctaaacgaa gataatgctg ctctagctca acggaactac tacgatcatg    4200
tggatataaa gattgagcaa ttagacaaaa gatatagtta tattgaacaa tggggtatac    4260
gactcttaga ggactgttca tcagcggaga ctcgacttga taattattca aacagtactc    4320
ttccacatgt ttctgaagcc gaagaaggta ataaagggta tacacctctt caaggacttg    4380
ttaatgagat tgaacacagt gaagagcctg gagatatcaa tgtagaaact gagagaagca    4440
cgaagcgcat gcgggtaagc attaagcaat aattgtaaca ttgactat tcatctctca    4500
attcttttg cattattgac aactagattc ttttgcagct atatcacttc atataagtaa    4560
tattagggtg tctacgtcca aactaaacgg atggggtaaa tacgcacttt agaggactgt    4620
catcagcgaa gaaccgacat ggtaatccaa acactatgca gcatgtttgt gaagctgatg    4680
aaggcagtga tggatgccat taaactgatc agagcgaagac gcgaggagac agtgatgaat    4740
agtgatatag gtagggagag tgatcacttt gaagagtgcg aatatagtga tataagcaat    4800
gagagtgatt agagtgaaga gcatgggat agtgacgatg atggtataag caatgagacc    4860
aatctgttgg aagagtgtgg aaacagtgat taggcaatga gcttgatcag aatgaagaca    4920
gttgagatag agagaaccaa tacacaatac aaggtaagta ttaatcaaga actgaacaga    4980
atatcagata tctcacagtc aggatcttta atagtataga tcaatgagtt gttttctttt    5040
acttgcagat tacgtgaaaa agaaatgaat ctttgagata cttttatggt gatgaaatga    5100
gtagttttgc tgtcggttct atggaacaac aaggagagcc caagattctt cattgtcttc    5160
agggcagatg aagatgttgc tgttcatgtg aatgttttaa aatgttttgt ttcttgttctt    5220
aggttgcacg tttttgataa gcttatttca ttactataac atttgctttct    5280
tagcacaaag ttttcagtga aacccgaatt gagtttgtga tttataatag ttctctttttt    5340
ttatgaatag ttgaaaagtg ttatgtatag catcaaccta ttatggagag aaatcgaacg    5400
actgacttac tttgtagcca ca                                              5422

SEQ ID NO: 9        moltype = DNA   length = 4359
FEATURE             Location/Qualifiers
source              1..4359
                    mol_type = other DNA
                    organism = Arabidopsis thaliana
SEQUENCE: 9
gttaaatgtt ttatatccac caagacagac tcactacttc tcctctattt ctcttcttaa     60
aagtcttcgt tccttgtttc ctccttctaa ctctctctct ctatggcttc gtcatcttct    120
tctcacaatt ggtatatga tgttttcttg agcttcagag gggaagacgt ccgcgtaaca    180
ttccgtagca acttcctcaa agagcttgat cggaaactaa tcactgcttt cagagacaat    240
gagatcgaga gaagccactc tctctggccc gatcttgaac aagccatcaa ggaatccagg    300
```

```
atcgctgtgg tcgtttttctc aaaaaactac gcttcatcga gctggtgtct taacgagttg   360
ctggagattg taaactgcaa tgataaaatt gtcataccag ttttctacca tgtggatcct   420
tcccaagtga ggcatcaaat cggcgacttc ggaaagatct ttgaaaatac ttgcaagaga   480
caaacgatg aggaagtgaa aaatcaatgg aagaaagcgt tgactcttgt agcgaatatg   540
cttggatttg actctgccaa atggaacgac gaagcaaaaa tgattgaaga aatagccaat   600
gatgttttgg gtaaactgct tttaactaca cccaaggatt ctgaggaact tgttggcatc   660
gaagatcaca tcgctgaaat gagtttactg ctgcaactgg aatctaaaga agtgagaatg   720
gttggtatat cgggttcctc agggattggt aagactacca ttgcaagagc tctgtttaaa   780
cgactttctc gacatttcca aggtagcact ttcatcgaca gggcttttgt atcttatagt   840
cggaatattt atagtggcgc caatccggac gaccccaata tgaagttgca gctacaagga   900
cacttcctat ctgaaattct cgggaaaaaa gacataaaga tagatgatcc agctgcattg   960
gaagagaggc taaagcacca aaaagttctt atcattattg atgatttgga tgatataatg  1020
gtactagata cattagtggg tcaaactcaa tggtttggat atgggagcag aatcattgtg  1080
gttacaaatg ataagcactt cttgattgct catggaattg atcatattta gaagtaagt  1140
ttcccaactg atgtgcatgc ttgtcagatg ttatgtcaat ctgcattcaa gcaaaactat  1200
gctcctaaag gttttgagga tcttgtagtt gatgtagtaa gacatgcggg caattttcct  1260
ttgggtctta atcttttggg taaatatttg cggaggaggg atatggaata ctggatggat  1320
atgctgccaa ggcttgagaa tagtctacgt atagacggta aaattgaaaa aatactaaga  1380
atcagctatg atgggttaga gagtgaagat caagagatat tcgtcatat cgcatgtctt  1440
ttcaatcata tggaagtcac aaccatcaag tccttgctgg cagatagtga tgttagtttt  1500
gcactagaaa acctagctga taagtccctc attcatgtca gacaaggtta tgtggtgatg  1560
caccgttcgc tacaagaaat gggtagaaaa attgttcgca ttcagtccat tgacaaacct  1620
ggagaacgag aatttctggt ggatccaaat gatatacatg atatactcaa tgcatgcact  1680
ggtactcaaa aggttttagg tatatcactg gatataagga atattcgtga gttggatgta  1740
catgagaggg ccttcaaagg gatgtctaat ctccgtttct tagaaattaa gaactttggt  1800
ttgaaagaag acgtttgca tttacctcca agtttcgact atttgccccg tacactcaaa  1860
ctattgtgct ggtccaaatt tccaatgagg tgtatgcctt ttggttttcg tcctgaaaac  1920
cttgtcaagc tcgaaatgca gtacagcaag ctacataagc tatgggaagg agttgcgcca  1980
cttacatgtc taaggaaat ggatctgcac ggatcatcaa acctgaaagt aattccagat  2040
cttttcgaag ctactaatct cgagatactt aatcttaagt tttgcgagag tttggtcgag  2100
ctcccgtcct ctatacgaaa tctcaataaa ctgttgaact tggacatgct aaactgcaaa  2160
agtctgaaaa ttcttcctac cggattcaac ctcaaatctc ttgaccgcct caatctctat  2220
cattgctcaa agttgaagac ttttcccaaa ttctcaacca catctcagt tctcaatcta  2280
aatctaacaa acattgaaga tttcccttct aatttacatc tcgagaatct tgttgagttt  2340
agaatatcaa aagaagagag tgatgagaaa caatgggaag aagaagcc gcttacgccc  2400
ttcctggcga tgatgttgtc tcccactttg acgagcttgc atctcgagaa tctcccaagt  2460
ttggtggagc ttacttcctc atttcagaat ctcaatcaac tgaaggactt gatcataata  2520
aactgcataa atctggagac tctgcccacc ggaatcaacc tccaatctct tgattacctt  2580
tgtttcagtg gatgctcaca gttgaggagc tttcctgaaa tctcaaccaa catctcagtg  2640
ctctatctag acgaaacagc gattgaagag gttcctggt ggatcgagaa attctctaac  2700
ctcactgagc taagcatgaa cagttgcagc aggctaaaat gtgtgttcct acacatgtct  2760
aaaactgaaac atcttaagga agctttgttt cgaaattgtg gtacattgac cagagttgaa  2820
ttgagtggat atccaagtgg gatggaggtg atgaaagcag acaattga cacagcctcc  2880
tcttctcttc ctaaagtcgt actcagtttc ttggactgct tcaacttgga tccagaaact  2940
gtccttcatc accaagaatc aattattttc aactacatgt tattacagg gaagaagaa  3000
gtgccatcat atttcactta ccgtactact ggaagctcct ctctgaccat tcctatactt  3060
cacgtccatc tctcccaacc attcttcaga tttaggattg gcgcattggt aactaataag  3120
gaggagccag tagagctcga ggtaaaatgt gagttcaaag acagatttgg gaacaacttt  3180
gattatgaca tttatttcga agtaataaaa gatagatatt atgggggagga ttgctataat  3240
atagctatat tggactgtcg tatccctcta acgaagata atgctgctct agctcaacgg  3300
aactactacg atcatgtgga tataaagatt gagcaattga acaaaagata tagtgatatt  3360
gaacaatggg gtatacgact cttagaggac tgttcatcag cggagactcg acttgataat  3420
tattcaaaca gtactcttcc acatgtttct gaagccgaag aagtaataa agggtataca  3480
cctcttcaag gacttgttaa tgagattgaa cacagtgaag agcctggaga tatcaatgta  3540
gaaactgaga gaagcacgaa gcgcatgcgg ctatatcct tcatataagt aatattaggg  3600
tgtctacgtc caaactaaac ggatggggta aatacgacac ttagaggact gtcatcagcg  3660
aagaaccgac atggtaatcc aaacactatg cagcatgttt gtgaagctga tgaaggcagt  3720
gatggatgcc attaaactga tcagagcgaa gagcgaggag acagtgatga atagtgatat  3780
aggtagggag agtgatcact ttgaagagtg cgaatatagt gatataagca atgagtga   3840
ttagagtgaa gagcatgggg atagtgacga tgatggtata agcaatgacga ccaatctgtt  3900
ggaagagtgt ggaaacagtg attaggcaat gagcttgatc agaatgaaga cagttgagat  3960
agagagaacc aatacacaat acaagattac gtgaaaaga aatgaatctt tgagatactt  4020
ttatggtgat ggaatgagta gttttgctgt cggttcatg gaacaacaag gagagcccaa  4080
gattcttcat tgtcttcagg gcagatgaag atgttgctgt tcatgtgaat gttttaaaat  4140
gttttgtttc tgttcttagg ttgcacgttt ttgataagct tatttcatta ctataacgat  4200
tccttaatt tgctgtctag cacaaagttt tacagtgaac ccgaattgag tttgtgattt  4260
ataatagttc tcttttttta tgaatagttg aaaagtgtta tgtatagcat acacctatta  4320
tggagagaaa tcgaacgact gacttacttt gtagccaca                         4359

SEQ ID NO: 10        moltype = AA   length = 1161
FEATURE              Location/Qualifiers
source               1..1161
                     mol_type = protein
                     organism = Arabidopsis thaliana
SEQUENCE: 10
MASSSSSHNW LYDVFLSFRG EDVRVTFRSH FLKELDRKLI TAFRDNEIER SHSLWPDLEQ    60
AIKESRIAVV VFSKNYASSS WCLNELLEIV NCNDKIVIPV FYHVDPSQVR HQIGDFGKIF   120
ENTCKRQTDE EVKNQWKKAL TLVANMLGFD SAKWNDEAKM IEEIANDVLG KLLLTTPKDS   180
EELVGIEDHI AEMSLLLQLE SKEVRMVGIS GSSGIGKTTI ARALFKRLSR HFQGSTFIDR   240
```

```
AFVSYSRNIY SGANPDDPNM KLQLQGHFLS EILGKKDIKI DDPAALEERL KHQKVLIIID  300
DLDDIMVLDT LVGQTQWFGY GSRIIVVTND KHFLIAHGID HIYEVSFPTD VHACQMLCQS  360
APKQNYAPKG FEDLVVDVVR HAGNFPLGLN LLGKYLRRRD MEYWMDMLPR LENSLRIDGK  420
IEKILRISYD GLESEDQEIF RHIACLFNHM EVTTIKSLLA DSDVSFALEN LADKSLIHVR  480
QGYVVMHRSL QEMGRKIVRI QSIDKPGERE FLVDPNDIHD ILNACTGTQK VLGISLDIRN  540
IRELDVHERA FKGMSNLRFL EIKNFGLKED GLHLPPSFDY LPRTLKLLCW SKFPMRCMPF  600
GFRPENLVKL EMQYSKLHKL WEGVAPLTCL KEMDLHGSSN LKVIPDLSEA TNLEILNLKF  660
CESLVELPSS IRNLNKLLNL DMLNCKSLKI LPTGFNLKSL DRLNLYHCSK LKTFPKFSTN  720
ISVLNLNLTN IEDFPSNLHL ENLVEFRISK EESDEKQWEE EKPLTPFLAM MLSPTLTSLH  780
LENLPSLVEL TSSFQNLNQL KDLIIINCIN LETLPTGINL QSLDYLCFSG CSQLRSFPEI  840
STNISVLYLD ETAIEEVPWW IEKFSNLTEL SMNSCSRLKC VFLHMSKLKH LKEALFRNCG  900
TLTRVELSGY PSGMEVMKAD NIDTASSSLP KVVLSFLDCF NLDPETVLHH QESIIFNYML  960
FTGKEEVPSY FTYRTTGSSS LTIPILHVHL SQPFFRFRIG ALVTNKEEPV ELEVKCEFKD 1020
RFGNNFDYDI YFEVNKDRYY GEDCYNIAIL DCRIPLNEDN AALAQRNYYD HVDIKIEQLD 1080
KRYSDIEQWG IRLLEDCSSA ETRLDNYSNS TLPHVSEAEE GNKGYTPLQG LVNEIEHSEE 1140
PGDINVETER STKRMRLYHF I                                          1161

SEQ ID NO: 11          moltype = DNA  length = 4886
FEATURE                Location/Qualifiers
source                 1..4886
                       mol_type = other DNA
                       organism = Arabidopsis thaliana
SEQUENCE: 11
acagactcac tacttctcct ctatttctct tcttaaaagt cttcgttcct tgtttcctcc   60
ttctaactct ctctctctat ggcttcgtca tcttcttctc acaattggtt atatgatgtt  120
ttcttgagct tcagagggga agacgtccgc gtaacattcc gtagccactt tctcaaagag  180
cttgatcgga aactaatcac tgctttcaga gacaatgaga tcgagagaag ccactctctc  240
tggcccgatc ttgaacaagc catcaaggaa tccaggatcg ctgtggtcgt tttctcaaaa  300
aactacgctt catcgagctg tgtcttaacg agttgctgg agattgtaaa ctgcaatgat  360
aaaattgtca taccagtttt ctaccatgtg gatccttccc aagtgaggca tcaaatcggc  420
gacttcggaa agatctttga aaatacttgc aagagacaaa cagatgagga agtgaaaaat  480
caatggaaga aagcgttgac tcttgtagcg aatatgcttg gatttgactc tgccaaatgg  540
aacgacgaag caaaaatgat tgaagaaata gccaatgatg ttttgggtaa actgctttta  600
actacaccca aggattctga ggaacttgtt ggcatcgaag atcacatcgc tgaaatgagt  660
ttactgctgc aactggaatc taagaagtg agaatggttg gtatatcggg ttcctcaggg  720
attggtaaga ctaccattgc aagagctctg tttaaacgac tttctcgaca tttccaaggt  780
agcactttca tcgacagggc ttttgtatct tatagtcgga atatttatag tggcgccaat  840
ccggacgacc ccaatatgaa gttgcagcta caaggacact tcctatctga aattctcggg  900
aaaaaagaca taaagataga tgatccagct gcattggaga agaggctaaa gcaccaaaaa  960
gttcttatca ttattgatga tttggatgat ataatggtac tagatacatt agtgggtcaa 1020
actcaatggt ttggatatgg gagcagaatc attgtggtta caaatgataa gcacttcttg 1080
attgctcatg gaattgatca tatttatgaa gtaagtttcc caactgatgt gcatgcttgt 1140
cagatgttat gtcaatctgc attcaagcaa aactatgctc ctaaaggttt tgaggatctt 1200
gtagttgatg tagtaagaca tgcgggcaat tttcctttgg gtcttaatct tttgggtaaa 1260
tatttgcgga ggagggatat ggaatactgg atggatatgc tgccaaggct tgagaatagt 1320
ctacgtatag acgtaaaat tgaaaaaata ctaagaatca gctatgatgg gttagagagt 1380
gaagatcaag agatatttcg tcatatcgca tgtcttttca atcatatgga agtcacaacc 1440
atcaagtcct tgctggcaga tagtgatgtt agttttgcac tagaaaaacct agctgataag 1500
tccctcattc atgtcagaca aggttatgtg gtgatgcacc gttcgctaca agaaatgggt 1560
agaaaaattg ttcgcattca gtccattgac aaacctggag aacgagaatt tctggtggat 1620
ccaaatgtgta tacatgatat actcaatgca tgcactgata ctcaaaaggt tttaggtata 1680
tcactggata taaggaatat tcgtgagttg gatgtacatg agagggcctt caaagggatg 1740
tctaatctcc gtttcttaga aattaagaac tttggtttga agaagacgg tttgcattta 1800
cctccaagtt tcgactattt gccccgtaca ctcaaactat tgtgctggtc caaatttcca 1860
atgaggtgta tgccttttgg ttttcgtcct gaaaaacctg tcaagctgca aatgcagtag 1920
agcaagctac ataagctatg gaaggagtg gcgccactta catgtctaaa ggaaatggat 1980
ctgcacggat catcaaacct gaaagtaatt ccagatcttt ctgaagctac taatctcgag 2040
atacttaatc ttaagttttg cgagagtttg gtcgagctcc cgtcctctat acgaaatctc 2100
aataaactgt tgaacttgga catgctaaac tgcaaaagtc tgaaaattct tcctaccgga 2160
ttcaacctca aatctcttga ccgcctcaat ctctatcatt gctcaaagtt gaagactttt 2220
cccaaattct caaccaacat ctcagttctc aatctaaatc taacaaacat tgaagatttc 2280
ccttctaatt tacatctcga gaatcttgtt gagtttagaa tcaaaagaa agagagtgat 2340
gagaaacaat gggaagaaga aaggtaagt agttctacac ttaacattat ctccaaactc 2400
tttccctaac actttttataa aagtaaaaaa aaatcattgt cgttgactcg tgtgaaaact 2460
taaaaaacac taattttttat atatttatga ataattaat ttgattggaa agtaaatttt 2520
ggttacaaag aatgaagaag aaaatatctg attttaaaaa aaaataaata aaaagtaaaa 2580
aacagataaa aatggaaaga aataagaaa ttaaagatga tatcaattgg gttttttcct 2640
ttgtcgtgat atcattaaaa cgtaaaagaa aattatacat gggattttct taatttatta 2700
tttttagcta ttttctaatg acatatatta tgtaattaaa aaataattaa ttttaataaa 2760
gagtagatgt gatcgtgaat ggaaagttcc aaacaatcta ttaataccga tgagatttac 2820
ccataataca ttagtactgt tattcttttc gttttaaag atttattttc taaaatttaa 2880
ctttaaaagt aatttgccac tgaaacccg taaaacttgt tatttggttc agccgcttac 2940
gccccttcctg gcgatgatgt tgtctcccac tttgacgagc ttgcatctcg agaatctccc 3000
aaggttggtg gacttactt cctcatttca gaatctcaat caactgaagg acttgatcat 3060
aataaactgc ataaatctgg agactctgcc caccggaatc aacctccaat ctcttgatta 3120
cctttgtttc agtggatgct cacagttgag gagcttccct gaaatctcaa ccaacatctc 3180
agtgctctat ctagacgaaa cagcgattga agaggttcct tggtggatcg agaaattctc 3240
taacctcact gagctaagca tgaacagttg cagcaggcta aatgtgtgt tcctacacat 3300
gtctaaactg aaacatctta aggaagcttt gtttcgaaat tgtggtacat tgaccagagt 3360
```

```
tgaattgagt ggatatccaa gtgggatgga ggtgatgaaa gcagacaata ttgacacagc   3420
ctcctcttct cttcctaaag tcgtactcag tttcttggac tgcttcaact tggatccaga   3480
aactgtcctt catcaccaag aatcaattat tttcaactac atgttattta cagggaaaga   3540
agaagtgcca tcatatttca cttaccgtac tactggaagc tcctctctga ccattcctat   3600
acttcacgtc catctctccc aaccattctt cagatttagg attggcgcat tggtaactaa   3660
taaggaggag ccagtagagc tcgaggtaaa atgtgagttc aaagacagat ttgggaacaa   3720
ctttgattat gacatttatt tcgaagttaa taaagataga tattatgggg aggattgcta   3780
taatatagct atattggact gtcgtatccc tctaaacgaa gataatgctg ctctagctca   3840
acggaactac tacgatcatg tggatataaa gattgagcaa ttagacaaaa gatatagtga   3900
tattgaacaa tggggtatac gactcttaga ggactgttca tcagcggaga ctcgacttga   3960
taattattca aacagtactc ttccacatgt ttctgaagcc gaagaaggta ataaagggta   4020
tacacctctt caaggacttg ttaatgagat tgaaacagtg gaagagcctg gagatatcaa   4080
tgtagaaact gagagaagca cgaagcgcat gcggctatat cacttcatat aagtaatatt   4140
agggtgtcta cgtccaaact aaacggatgg ggtaaatacg acacttagag gactgtcatc   4200
agcgaagaac cgacactggta atccaaacac tatgcagcat gtttgtgaag ctgatgaagg   4260
cagtgatgga tgccattaaa ctgatcagag cgaagagcga ggagacagtg atgaatagtg   4320
atataggtag ggagagtgat cacttttgaag agtgcgaata tagtgatata agcaatgaga   4380
gtgattagag tgaagagcat ggggatagtg acgatgatgt tataagcaat gaccaatca   4440
tgttggaaga gtgtgaaaac agtgattagg caatgagctt gatcagaatg aagacagtta   4500
agatagagag aaccaataca caatacaaga ttacgtgaaa aagaaatgaa tctttgagat   4560
actttatatg tgatggaatg agtagttttg ctgtcggttc tatggaacaa caaggagagc   4620
ccaagattct tcattgtctt cagggacagat gaagatgtct ctgttcatgt gaatgtttta   4680
aaatgttttg tttctgttct taggttgcac gtttttgata agcttatttc attactataa   4740
cgattccttt aatttgctgt ctagcacaaa gttttacagt gaacccgaat tgagtttgtg   4800
atttataata gttctctttt tttatgaata gttgaaaagt gttatgtata gcatacacct   4860
attatggaga gaaatcgaac gactga                                        4886

SEQ ID NO: 12          moltype = AA   length = 776
FEATURE                Location/Qualifiers
source                 1..776
                       mol_type = protein
                       organism = Arabidopsis thaliana
SEQUENCE: 12
MASSSSSHNW LYDVFLSFRG EDVRVTFRSH FLKELDRKLI TAFRDNEIER SHSLWPDLEQ    60
AIKESRIAVV VFSKNYASSS WCLNELLEIV NCNDKIVIPV FYHVDPSQVR HQIGDFGKIF   120
ENTCKRQTDE EVKNQWKKAL TLVANMLGFD SAKWNDEAKM IEEIANDVLG KLLLTTPKDS   180
EELVGIEDHI AEMSLLLQLE SKEVRMVGIS GSSGIGKTTI ARALFKRLSR HFQGSTFIDR   240
AFVSYSRNIY SGANPDDPNM KLQLQGHFLS EILGKKDIKI DDPAALEERL KHQKVLIIID   300
DLDDIMVLDT LVGQTQWFGY GSRIIVVTND KHFLIAHGID HIYEVSFPTD VHACQMLCQS   360
AFKQNYAPKG FEDLVVDVVR HAGNFPPLGLN LLGKYLRRRD MEYWMDMLPR LENSLRIDGK   420
IEKILRISYD GLESEDQEIF RHIACLFNHM EVTTIKSLLA DSDVSFALEN LADKSLIHVR   480
QGYVVMHRSL QEMGRKIVRI QSIDKPGERE FLVDPNDIHD ILNACTGTQK VLGISLDIRN   540
IRELDVHERA FKGMSNLRFL EIKNFGLKED GLHLPPSFDY LPRTLKLLCW SKFPMRCMPF   600
GFRPENLVKL EMQYSKLHKL WEGVAPLTCL KEMDLHGSSN LKVIPDLSEA TNLEILNLKF   660
CESLVELPSS IRNLNKLLNL DMLNCKSLKI LPTGFNLKSL DRLNLYHCSK LKTFPKFSTN   720
ISVLNLNLTN IEDFPSNLHL ENLVEFRISK EESDEKQWEE EKVSSSTLNI ISKLFP       776

SEQ ID NO: 13          moltype = DNA   length = 2932
FEATURE                Location/Qualifiers
source                 1..2932
                       mol_type = other DNA
                       organism = Arabidopsis thaliana
SEQUENCE: 13
atttctcttc ttaaaagtct tcgttccttg tttcctcctt ctaactctct ctctctatgg     60
cttcgtcatc ttcttctcac aattggttat atgatgtttc cttgagcttc agagggggaag   120
acgtccgcgt aacattccgt agccactttc tcaaagagct tgatcggaaa ctaatcactg    180
ctttcagaga caatgagatc gagagaagcc actctctctg gcccgatctt gaacaagcca    240
tcaaggaatc caggatcgct gtggtcgttt ctcaaaaaa ctacgcttca tcgagctggt     300
gtcttaacga gttgctggag attgtaaact gcaatgataa aattgtcata ccagtttctt    360
accatgtga tccttcccaa gtgaggcatc aaatcggcga cttcggaaag atctttgaaa    420
atacttgcaa gagacaaaca gatgaggaag tgaaaatca atggaagaaa gcgttgactc    480
ttgtagcgaa tatgcttgga tttgactctg ccaaatggaa cgacgaagca aaaatgattg    540
aagaaatagc caatgatgtt ttgggtaaac tgcttttaac tacacccaag gattctgagg    600
aacttgttgg catcgaagat cacatcgctg aaatgagttt actgctgcaa ctggaatcta    660
aagaagtgag aatggttggt atatcggttt cctcaggat tggtaagact accattgcaa    720
gagctctgtt taaacgactt tctcgacatt tccaaggtag cacttttcatc gacagggctt   780
ttgtatctta tagtcggaat attttatagt gcgccaatcc ggacgacccc aatatgaagt    840
tgcagctaca aggacactc ctatctgaaa ttctcgggaa aaaagacata aagatagatg     900
atccagctgc attggaagag aggctaaagc accaaaaagt tcttatcatt attgatgatt    960
tggatgatat aatgggtacta gatacattag tgggtcaaac tcaatggttt ggatatggga   1020
gcagaatcat tgtggttaca aatgataagc acttcttgat tgctcatgga attgatcata   1080
tttatgaagt aagtttccca actgatgtgc atgcttgtca gatgttatgt caatctgcat   1140
tcaagcaaaa ctatgctcct aaaggttttg aggatcttgt agttgatgta gtaagacatg   1200
cgggcaatt tccttttggg tttaatcttt tgggtaaata tttgcggagg agggatggga   1260
aatactggat ggatatgctg ccaaggcttg agaatagtcc acgtatagac ggtaaaattg   1320
aaaaaatact aagaatcagc tatgatgggt tagagagtga agatcaagag atatttcgtc   1380
atatcgcatg tctttcaat catatggaag tcacaaccat caagtcctg ctggcagata     1440
gtgatgttag ttttgcacta gaaaacctag ctgataagtc cctcattcat gtcagacaag   1500
gttatgtggt gatgcaccgt tcgctacaag aaatgggtag aaaaattgtt cgcattcagt   1560
```

```
ccattgacaa acctggagaa cgagaatttc tggtggatcc aaatgatata catgatatac   1620
tcaatgcatg cactggtact caaaaggttt taggtatatc actggatata aggaatattc   1680
gtgagttgga tgtacatgag agggccttca aagggatgtc taatctccgt ttcttagaaa   1740
ttaagaactt tggtttgaaa gaagacggtt tgcatttacc tccaagtttc gactatttgc   1800
cccgtacact caaactattg tgctggtcca aatttccaat gaggtgtatg ccttttggtt   1860
ttcgtcctga aaaccttgtc aagctcgaaa tgcagtacag caagctacat aagctatggg   1920
aaggagttgc gccacttaca tgtctaaagg aaatggatct gcacggatca tcaaacctga   1980
aagtaattcc agatctttct gaagctacta atctcgagat acttaatctt aagttttgcg   2040
agagtttggt cgagctcccg tcctctatac gaaatctcaa taaactgttg aacttggaca   2100
tgctaaactg caaaagtctg aaaattcttc ctaccggatt caacctcaaa tctcttgacc   2160
gcctcaatct ctatcattgc tcaaagttga agacttttcc caaattctca accaacatct   2220
cagttctcaa tctaaatcta acaaacattg aagatttccc ttctaattta catctcgaga   2280
atcttgttga gtttagaata tcaaaagaag agagtgatga gaaacaatgg gaagaagaga   2340
aggtaagtag ttctacactt aacattatct ccaaactctt tccctaacac tttttataaa   2400
gtaaaaaaaa atcattgtcg ttgactcgtg tgaaaactta aaaaacacta attttttatat   2460
atttatgaat aatttaattt gattggaaag taaattttgg ttacaaagaa tgaagaagaa   2520
aatatctgat tttaaaaaaa aataaataaa aagtaaaaaa cagataaaaa tggaagaaa    2580
ataagaaatt aaagatgata tcaattgggt ttttcctttt gtcgtgatat cattaaaacg   2640
taaaagaaaa ttatacatgg gattttctta atttattatt tttagctatt ttctaatgac   2700
atatattatg taattaaaaa ataatcggtt ttaataaaga gtagatgtga tcgtgaatgg   2760
aaagttccaa acaatctatt aataccgatg agatttaccc ataatacatt agtactgtta   2820
ttcttttcgt tttaaagat ttatttttcta aaatttaact ttaaaagtaa tttgccactg     2880
aaaacccgta aaacttgtta tttggttcag ccgcttacgc ccttcctggc ga            2932

SEQ ID NO: 14               moltype = AA   length = 776
FEATURE                     Location/Qualifiers
source                      1..776
                            mol_type = protein
                            organism = Arabidopsis thaliana
SEQUENCE: 14
MASSSSSHNW LYDVFLSFRG EDVRVTFRSH FLKELDRKLI TAFRDNEIER SHSLWPDLEQ    60
AIKESRIAVV VFSKNYASSS WCLNELLEIV NCNDKIVIPV FYHVDPSQVR HQIGDFGKIF   120
ENTCKRQTDE EVKNQWKKAL TLVANMLGFD SAKWNDEAKM IEEIANDVLG KLLLTTPKDS   180
EELVGIEDHI AEMSLLLQLE SKEVRMVGIS GSSGIGKTTI ARALFKRLSR HFQGSTFIDR   240
AFVSYSRNIY SGANPDDPNM KLQLQGHFLS EILGKKDIKI DDPAALEERL KHQKVLIIID   300
DLDDIMVLDT LVGQTQWFGY GSRIIVVTND KHFLIAHGID HIYEVSFPTD VHACQMLCQS   360
AFKQNYAPKG FEDLVVDVVR HAGNFPLGLN LLGKYLRRRD MEYWMDMLPR LENSLRIDGK   420
IEKILRISYD GLESEDQEIF RHIACLFNHM EVTTIKSLLA DSDVSFALEN LADKSLIHVR   480
QGYVVMHRSL QEMGRKIVRI QSIDKPGERE FLVDPNDIHD ILNACTGTQK VLGISLDIRN   540
IRELDVHERA FKGMSNLRFL EIKNFGLKED GLHLPPSFDY LPRTLKLLCW SKFPMRCMPF   600
GFRPENLVKL EMQYSKLHKL WEGVAPLTCL KEMDLHGSSN LKVIPDLSEA TNLEILNLKF   660
CESLVELPSS IRNLNKLLNL DMLNCKSLKI LPTGFNLKSL DRLNLYHCSK LKTFPKFSTN   720
ISVLNLNLTN IEDFPSNLHL ENLVEFRISK EESDEKQWEE EKVSSSTLNI ISKLFP       776

SEQ ID NO: 15               moltype = DNA   length = 38
FEATURE                     Location/Qualifiers
misc_feature                1..38
                            note = Artificially synthesized oligonucleotide primer
source                      1..38
                            mol_type = other DNA
                            organism = synthetic construct
SEQUENCE: 15
ggtacccact agtcaacaat ggcttcttca tcttcttc                            38

SEQ ID NO: 16               moltype = DNA   length = 64
FEATURE                     Location/Qualifiers
misc_feature                1..64
                            note = Artificially synthesized oligonucleotide primer
source                      1..64
                            mol_type = other DNA
                            organism = synthetic construct
SEQUENCE: 16
catgcgtcga ctaagcgtaa tctggaacat cgtatgggta tatgaagtga tatagccgca    60
tgcg                                                                 64

SEQ ID NO: 17               moltype = DNA   length = 3522
FEATURE                     Location/Qualifiers
misc_feature                1..3522
                            note = Artificially synthesized tagged resistance gene
                             coding sequence
source                      1..3522
                            mol_type = other DNA
                            organism = synthetic construct
SEQUENCE: 17
atggcttctt catcttcttc tcacaattgg ttatatgatg ttttcttgag cttcagaggg    60
gaagacgtcc gcgtaacatt ccgtagccac tttctcaaag agcttgatcg gaaactaatc   120
actgctttca gagacaatga gatcgagaga agccactctc tctggcccga tcttgaacaa   180
gccatcaagg aatccaggat cgctgtggtc gttttctcca aaaactacgc ttcatcgagc   240
tggtgtctta acgagttgct ggagattgta aactgcaatg ataaaattgt cataccagtt   300
```

-continued

```
ttctaccatg tggatccttc acaagtgagg catcaaatcg gcgacttcgg aaagatcttt    360
gaaaatactt gcaagagaca aacagatgag gaagtgaaaa atcaatggaa gaaagcgctg    420
actcttgtag cgaatatgct tggatttgac tctgccaaat ggaacgacga agcaaaaatg    480
attgaagaaa tagccaatga tgttttgggt aaactgcttt taactacacc taaggattct    540
gaggaacttg ttggcatcga agatcacatc gctgaaatga gtttactgct gcaactggaa    600
tctgaagaag tgagaatggt tggtatatcg ggttcctcag ggattggtaa gactaccatt    660
gcaagagctc tgtttaaacg actttctcga catttccaag gtagcacttt catcgacagg    720
gcttttgtat cttatagtcg gaatatttat agtggcgcca atccgacgca ccccaatatg    780
aagttgcagc tacaaggaca cttcctatct gaaattctcg gcaaaaagga cataaagata    840
gatgatccag ctgcactgga agagaggcta aagcaccaaa aagttcttat cattattgat    900
gatttggatg atataaatgg tactagataca ttagtgggtc aaactcaatg gtttggatat    960
gggagcagaa tcattgtggt tacaaatgat aagcactcct tgattgctca tggaattgat   1020
catatttatg aagtaagttt cccaactgat gtgcatgctt gtcagatgtt atgtcaatct   1080
gcattcaagc aaaactatgc tcctaaaggt tttgaggatc ttgtagttga tgtagtaaga   1140
catgcgggca attttccttt gggtcttaat cttttgggta atatttgcg gaggagggat   1200
atggaatact ggatggatat gctgccaagg cttgagaata gtctacgtat agacggtaaa   1260
attgaaaaaa tactaagaat cagctatgat gggtagaga gtgaagatca agagatattt   1320
cgtcatatcg catgtctttt caatcatatg gaagtcacaa ccatcaagtc cttgctggca   1380
gatagtgatg ttagttttgc actagaaaac ctagctgata agtcccttat tcatgtcaga   1440
caaggttatg tggtgatgca ccgttcgcta caagaaatgg gtagaaaaat tgttcgcatt   1500
cagtccattg acaaacctgg agaacgaaa tttctggtgg atccaaatga tatacatgat   1560
atactcaatg catgcactgg tactcaaaag gtttaggta tatcactgga tataaggaat   1620
attcgtgagt tggatgtaca tgagagggcc ttcaaaggga tgtctaatct ccgtttctta   1680
gaaattaaga actttggttt gaagaagac ggtttgcatt tacctccaag tttcgactat   1740
ttgccccgta cactcaaaact attgtgctgg cccaaatttc caatgaggtg tatgcctttt   1800
ggttttcgtc ctgaaaacct tgtcaagctc gaaatgcaagt gcacaagct acataagcta   1860
tgggaaggag ttgtgccact tgcatgtcta aaggaaatgg atctgcgcgt atcattaaag   1920
ctgaaagtaa ttccagatct ttctgaagct actaatctcg agatacttaa tctttcgttt   1980
tgcgagagtt tggtcgagct cccatcctct atacgaaatc tcaataaact gttgaacttg   2040
gacatgttct actgcaaaag tctgaaaatt cttcctaccg gattcaacct caaatctctt   2100
gaccgcctcc atctcgatca ttgctcaaag ttgaagactt ttcccaaatt ctcaaccaac   2160
atctcagttc tcagtctaaa tctaacaaac attgaagatt ccccttctaa tttacatctc   2220
cagaatcttg ttgagtttag catatcaaaa gacgagagtg atgagaaaca atgggaagaa   2280
gagaagccgc ttacgccctt cctggcgatg atgttgtctc ccactttgac gatcttgcat   2340
ctctgtgata tgcccaagttt ggtggagctt ccttcctcat ttcagaatct caatcaactg   2400
aaggagttga tcataataaa ctgcataaat ctggagactc tgcccaccgg aatcaacctc   2460
caatctctct attccttag tttcagagga tgctcacagt tgaggagctt tcctgaaatc   2520
tcaaccaaca tctcagtgct ctatctagac gaaacagcga ttgaagaggt tccttggtgg   2580
atcgagaaat tctctaacct cactgagcta agaatggaca ggtgcagcag gctaaaatgt   2640
gtgttcctac acatttctaa actgaaacat cttcaggaag ctttgtttcg aaattgtggt   2700
acattgacca gagttgaatt gagtggatat ccaagtggga tggaggtgat gaaagcagac   2760
aatattgaca cagcctcctc ttctcttcct aaagtcgtac tcagtttctt ggactgcttc   2820
aacttggatc cagaaactgt ccttcatcac caagaatcaa ttattttaca ctacatgtta   2880
tttacaggga aaggagaagt gccatcatat ttcacttacc gtactactgg aagctcctct   2940
ctgaccattc ctctacttca cgtccatctc tcccaaccat tcttcagatt taggattggc   3000
gcattggtaa ctatagttaa tacggaggag ccagtagagc tcgaggtaaa atgtgagttc   3060
aaagacagat ttgggaacaa cttttgattat gacattatt tcgaagttta taatcaaaac   3120
tattgtgtgg aggatgacta tattatagct atattggact gtcgtatccc tctaaacgaa   3180
gataatgctg ctctagctca accgaactac tacgatcatg tggatataaa gattgagcaa   3240
ttagaggaag aggaaagata tggtgatatt gaacaatggg gtatacgact cttagaggac   3300
tgttcatcag cggagactcg acttgataat tcaaacgata ctcttccaca tgtttctgaa   3360
gccgaagaag gcaatatagg gtatacacct cttcaaggac ttgttaatga gattgaacac   3420
agtgaagagc ctgagagatat caatgtgaaa actgagagaa gcacgaagcg catgcggcta   3480
tatcacttca tataccccata cgatgttcca gattacgctt ag                     3522
```

SEQ ID NO: 18          moltype = AA   length = 1173
FEATURE                Location/Qualifiers
REGION                 1..1173
                       note = Artificially synthesized tagged resistance gene
                        amino acidsequence
source                 1..1173
                       mol_type = protein
                       organism = synthetic construct
SEQUENCE: 18

```
MASSSSSHNW LYDVFLSFRG EDVRVTFRSH FLKELDRKLI TAFRDNEIER SHSLWPDLEQ    60
AIKESRIAVV VFSINYASSS WCLNELLEIV NCNDKIVIPV FYHVDPSQVR HQIGDFGKIF   120
ENTCKRQTDE EVKNQWKKAL TLVANMLGFD SAKWNDEAKM IEEIANDVLG KLLLTTPKDS   180
EELVGIEDHI AEMSLLLQLE SEEVRMVGIS GSSGIGKTTI ARALFKRLSR HPQGSTFIDR   240
AFVSYSRNIY SGANPDDPNM KLQLQGHFLS EILGKKDIKI DDPAALEERL KHQKVLIIID   300
DLDDIMVLDT LVGQTQWFGY GSRIIVVTND KHFLIAHGID HIYEVSFPTD VHACQMLCQS   360
AFKQNYAPKG FEDLVVDVVR HAGNFPLGLN LLGKYLRRRD MEYWMDMLPR LENSLRIDGK   420
IEKILRISYD GLESEDQEIF RHIACLFNHM EVTTIKSLLA DSDVSFALEN LADKSLIHVR   480
QGYVVMHRSL QEMGRKIVRI QSIDKPGERE FLVDPNDIHD ILNACTGTQK VLGISLDIRN   540
IRELDVHERA FKGMSNLRFL EIKNFGLKED GLHLPPSFDY LPRTLKLLCW PKFPMRCMPF   600
GFRPENLVKL EMQCSKLHKL WEGVVPLACL KEMDLRVSLK LKVIPDLSEA TNLEILNLSF   660
CESLVELPSS IRNLKLLNL DMFYCKSLKI LPTGFNLKSL DRLHLDHCSK LKTFPKFSTN   720
ISVLSLNLTN IEDFPSNLHL QNLVEFSISK DESDEKQWEE EKPLTPFLAM MLSPTLTILH   780
LCDMPSLVEL PSSFQNLNQL KELIIINCIN LETLPTGINL QSLYYLSFRG CSQLRSFPEI   840
STNISVLYLD ETAIEEVPWW IEKFSNLTEL RMDRCSRLKC VFLHISKLKH LQEALFRNCG   900
```

```
TLTRVELSGY PSGMEVMKAD NIDTASSSLP KVVLSFLDCF NLDPETVLHH QESIIFNYML   960
FTGKGEVPSY FTYRTTGSSS LTIPLLHVHL SQPFFRFRIG ALVTIVNTEE PVELEVKCEF  1020
KDRFGNNFDY DIYFEVYNQN YCVEDDYIIA ILDCRIPLNE DNAALAQPNY YDHVDIKIEQ  1080
LEEEERYGDI EQWGIRLLED CSSAETRLDN SNSTLPHVSE AEEGNIGYTP LQGLVNEIEH  1140
SEEPGDINVE TERSTKRMRL YHFIYPYDVP DYA                              1173

SEQ ID NO: 19            moltype = DNA   length = 30
FEATURE                  Location/Qualifiers
misc_feature             1..30
                         note = Artificially synthesized peptide tag sequence
source                   1..30
                         mol_type = other DNA
                         organism = synthetic construct
CDS                      1..30
SEQUENCE: 19
gaacagaaac ttatctccga agaagatctg                                    30

SEQ ID NO: 20            moltype = AA    length = 10
FEATURE                  Location/Qualifiers
REGION                   1..10
                         note = Synthetic Construct
source                   1..10
                         mol_type = protein
                         organism = synthetic construct
SEQUENCE: 20
EQKLISEEDL                                                          10

SEQ ID NO: 21            moltype = DNA   length = 18
FEATURE                  Location/Qualifiers
misc_feature             1..18
                         note = Artificially synthesized peptide tag sequence
source                   1..18
                         mol_type = other DNA
                         organism = synthetic construct
CDS                      1..18
SEQUENCE: 21
caccaccatc atcaccac                                                 18

SEQ ID NO: 22            moltype = AA    length = 6
FEATURE                  Location/Qualifiers
REGION                   1..6
                         note = Synthetic Construct
source                   1..6
                         mol_type = protein
                         organism = synthetic construct
SEQUENCE: 22
HHHHHH                                                               6

SEQ ID NO: 23            moltype = DNA   length = 24
FEATURE                  Location/Qualifiers
misc_feature             1..24
                         note = Artificially synthesized peptide tag sequence
source                   1..24
                         mol_type = other DNA
                         organism = synthetic construct
CDS                      1..24
SEQUENCE: 23
gactataagg acgacgacga caag                                          24

SEQ ID NO: 24            moltype = AA    length = 8
FEATURE                  Location/Qualifiers
REGION                   1..8
                         note = Synthetic Construct
source                   1..8
                         mol_type = protein
                         organism = synthetic construct
SEQUENCE: 24
DYKDDDDK                                                             8

SEQ ID NO: 25            moltype = DNA   length = 39
FEATURE                  Location/Qualifiers
misc_feature             1..39
                         note = Artificially synthesized peptide tag sequence
source                   1..39
                         mol_type = other DNA
                         organism = synthetic construct
CDS                      1..39
SEQUENCE: 25
ggggcgccgg ttccataccc cgacccacta gaaccacgt                          39
```

| SEQ ID NO: 26 | moltype = AA   length = 13 |
| --- | --- |
| FEATURE | Location/Qualifiers |
| REGION | 1..13 |
| | note = Synthetic Construct |
| source | 1..13 |
| | mol_type = protein |
| | organism = synthetic construct |

SEQUENCE: 26
GAPVPYPDPL EPR                                                          13

| SEQ ID NO: 27 | moltype = DNA   length = 39 |
| --- | --- |
| FEATURE | Location/Qualifiers |
| misc_feature | 1..39 |
| | note = Artificially synthesized peptide tag sequence |
| source | 1..39 |
| | mol_type = other DNA |
| | organism = synthetic construct |
| CDS | 1..39 |

SEQUENCE: 27
ggcgctccgg taccttatcc tgatcctctg gagccaagg                               39

| SEQ ID NO: 28 | moltype = AA   length = 13 |
| --- | --- |
| FEATURE | Location/Qualifiers |
| REGION | 1..13 |
| | note = Synthetic Construct |
| source | 1..13 |
| | mol_type = protein |
| | organism = synthetic construct |

SEQUENCE: 28
GAPVPYPDPL EPR                                                          13

| SEQ ID NO: 29 | moltype = DNA   length = 303 |
| --- | --- |
| FEATURE | Location/Qualifiers |
| source | 1..303 |
| | mol_type = genomic DNA |
| | organism = Arabidopsis thaliana |

SEQUENCE: 29
ccaacactcg aatccccacc cgttggacca aacccggctc attaagcgtc ggttcagatt        60
tatttccttt atttaaaaaa aaggaaaggg taaaaaatag aaaattggaa acagttaaag       120
cccaaaattg taatttaccg agaattgtaa atttacctga aaaccctacg ctatagtttc       180
gactataaat accaaactta ggacctcact tcagaatccc ctcgtcgctg cgtctctctc       240
ccgcaacctt cgatttttcgt ttattcgcat ccatcggaga gagaaaacaa tcaataagcg       300
acc                                                                    303

| SEQ ID NO: 30 | moltype = DNA   length = 675 |
| --- | --- |
| FEATURE | Location/Qualifiers |
| source | 1..675 |
| | mol_type = genomic DNA |
| | organism = Arabidopsis thaliana |

SEQUENCE: 30
atatttcaca aattgaacat agactacaga attttagaaa acaaactttc tctctcttat        60
ctcacccttta tcttttagag agaaaaagtt cgatttccgg ttgaccggaa tgtatctttg       120
ttttttttgt tttgtaacat atttcgtttt ccgatttaga tcggatctcc tttttccgttt       180
tgtcggacct tcttccggtt tatccggatc taataatatc catcttagac ttagctaagt       240
ttggatctgt tttttggtta gctcttgtca atcgcctcat catcagcaag aaggtgaaat       300
ttttgacaaa taaatcttag aatcatgtag tgtctttgga ccttgggaat gatagaaacg       360
atttgttata gctactctat gtatcagacc ctgaccaaga tccaacaatc tcataggttt       420
tgtgcatatg aaaccttcga ctaacgagaa gtggtctttt aatgagagag atatctaaaa       480
tgttatctta aaagcccact caaatctcaa ggcataaggt agaaatgcaa atttggaaag       540
tgggctgggc ctttttgtggt aaaggcctgt aacctagccc aatattagca aaaccctaga       600
cgcgtacatt gacatatata aacccgcctc ctccttgttt agggtttcta cgtgagagaa       660
gacgaaaacac aaaag                                                      675

| SEQ ID NO: 31 | moltype = DNA   length = 255 |
| --- | --- |
| FEATURE | Location/Qualifiers |
| source | 1..255 |
| | mol_type = genomic DNA |
| | organism = Cauliflower mosaic virus |

SEQUENCE: 31
attgagactt tcaacaaag ggtaatatcc ggaaacctcc tcggattcca ttgcccagct         60
atctgtcact ttattgtgaa gatagtggaa aaggaaggtg gctcctacaa atgccatcat       120
tgcgataaag gaaaggccat cgttgaagat gcctctgccg acagtggtcc caaagatgga       180
cccccaccca cgaggagcat cgtggaaaaa gaagacgttc caaccacgtc ttcaaagcaa       240
gtggattgat gtgat                                                       255

| SEQ ID NO: 32 | moltype = DNA   length = 665 |
| --- | --- |
| FEATURE | Location/Qualifiers |
| misc_feature | 1..665 |

```
                    note = Artificially synthesized 2x 35S promoter cassette
source              1..665
                    mol_type = other DNA
                    organism = synthetic construct
SEQUENCE: 32
gcgttaactg caggtccgat tgagactttt caacaaaggg taatatccgg aaacctcctc    60
ggattccatt gcccagctat ctgtcacttt attgtgaaga tagtggaaaa ggaaggtggc   120
tcctacaaat gccatcattg cgataaagga aaggccatcg ttgaagatgc ctctgccgac   180
agtggtccca aagatggacc cccacccacg aggagcatcg tggaaaaaga agacgttcca   240
accacgtctt caaagcaagt ggattgatgt gatggtccga ttgagacttt tcaacaaagg   300
gtaatatccg gaaacctcct cggattccat tgcccagcta tctgtcactt tattgtgaag   360
atagtggaaa aggaaggtgg ctcctacaaa tgccatcatt gcgataaagg aaaggccatc   420
gttgaagatg cctctgccga cagtggtccc aaagatggac ccccacccac gaggagcatc   480
gtggaaaaag aagacgttcc aaccacgtct caaagcaag tggattgatg tgatatctcc   540
actgacgtaa gggatgacgc acaatcccac tatccttcgc aagacccttc ctctatataa   600
ggaagttcat tcatttgga gaggacacgc tgacaagctg actctagcag atcactagtg   660
ggtac                                                              665

SEQ ID NO: 33       moltype = DNA  length = 254
FEATURE             Location/Qualifiers
source              1..254
                    mol_type = genomic DNA
                    organism = Agrobacterium tumefaciens
SEQUENCE: 33
gatcgttcaa acatttggca ataaagtttc ttaagattga atcctgttgc cggtcttgcg    60
atgattatca tataatttct gttgaattac gttaagcatg taataattaa catgtaatgc   120
atgacgttat ttatgagatg ggttttttatg attagagtcc cgcaattata catttaatac   180
gcgatagaaa acaaaatata gcgcgcaaac taggataaat tatcgcgcgc ggtgtcatct   240
atgttactag atcg                                                    254

SEQ ID NO: 34       moltype = DNA  length = 295
FEATURE             Location/Qualifiers
source              1..295
                    mol_type = genomic DNA
                    organism = Pisum sativum
SEQUENCE: 34
gttcgagtat tatggcattg ggaaaactgt ttttcttgta ccatttgttg tgcttgtaat    60
ttactgtgtt ttttattcgg ttttcgctat cgaactgtga aatggaaatg gatggagaag   120
agttaatgaa tgatatggtc cttttgttca ttctcaaatt aatatattt gtttttctc    180
ttatttgttg tgtgttgaat ttgaaattat aagagatatg caaacatttt gttttgagta   240
aaaatgtgtc aaatcgtggc ctctaatgac cgaagttaat atgaggagta aaaca        295

SEQ ID NO: 35       moltype = DNA  length = 27
FEATURE             Location/Qualifiers
misc_feature        1..27
                    note = Artificially synthesized HA encoding nucleotide
                    sequence A
source              1..27
                    mol_type = other DNA
                    organism = synthetic construct
SEQUENCE: 35
tacccatacg atgttccaga ttacgct                                       27

SEQ ID NO: 36       moltype = DNA  length = 27
FEATURE             Location/Qualifiers
misc_feature        1..27
                    note = Artificially synthesized HA encoding nucleotide
                    sequence B
source              1..27
                    mol_type = other DNA
                    organism = synthetic construct
SEQUENCE: 36
tatccatatg atgttccaga ttatgct                                       27

SEQ ID NO: 37       moltype = AA  length = 9
FEATURE             Location/Qualifiers
REGION              1..9
                    note = Artificially synthesized HA tag
source              1..9
                    mol_type = protein
                    organism = synthetic construct
SEQUENCE: 37
YPYDVPDYA                                                            9
```

```
SEQ ID NO: 38          moltype = AA  length = 14
FEATURE                Location/Qualifiers
source                 1..14
                       mol_type = protein
                       organism = Arabidopsis thaliana
SEQUENCE: 38
VSSSTLNIIS KLFP                                                                  14
```

COMPOSITIONS AND METHODS FOR CONFERRING RESISTANCE TO GEMINIVIRUS

CROSS REFERENCE TO RELATED APPLICATIONS

The instant application is a U.S. National Stage Application of PCT International Patent Application Serial No. PCT/US2022/075981, filed Sep. 6, 2022, which claims the benefit of U.S. Provisional Patent Application Ser. No. 63/240,724, filed Sep. 3, 2021, the disclosure of each of which incorporated herein by reference in its entirety.

REFERENCE TO SEQUENCE LISTING XML

The Sequence Listing XML associated with the instant disclosure has been electronically submitted to the United States Patent and Trademark Office via the Patent Center as an 85,539 byte UTF-8-encoded XML file created on Sep. 6, 2022 and entitled "297_354_PCT.xml". The Sequence Listing submitted via Patent Center is hereby incorporated by reference in its entirety.

TECHNICAL FIELD

The presently disclosed subject matter pertains to isolated nucleic acid molecules that encode polypeptides for geminivirus resistance. The presently disclosed subject matter also relates to methods for using nucleic acid molecules and/or polypeptides from *Arabidopsis* and derivatives thereof in transgenic plants to confer the desired agronomic traits, and to uses of such nucleic acid molecules to assist germplasm enhancement by breeding.

BACKGROUND

Geminiviruses are very serious threats to agriculture, especially under the global warming trend, which will allow their insect vectors to colonize previously restricted areas (Beam & Ascencio-Ibanez, 2020). The geminiviruses are a large and diverse family of plant DNA viruses, with circular single-stranded (ss) DNA genomes that replicate through circular double stranded DNA intermediates. See Lazarowitz, 1992; Timmermans et al., 1994; Hanley-Bowdoin et al., 1999. Viral DNA replication, which results in both single and double stranded viral DNAs in large amounts, involves the expression of only a small number of viral proteins that are involved in replication or viral transcription. Geminiviruses rely primarily on the machinery of the host to copy their genomes and express their genes, including the nuclear DNA and RNA polymerases of their plant hosts. These properties of geminiviruses are unusual among plant viruses, most of which are RNA viruses or replicate through RNA intermediates using virus-encoded replicases.

Geminiviruses are subdivided based primarily their genome structure, and insect vector. Geminiviruses in the Mastrevirus genus are transmitted by leafhoppers and infect primarily monocots, although mastreviruses that infect dicots are also known. Geminiviruses in the Curtovirus genus are transmitted by leafhoppers and infect dicots. Geminiviruses in the Begomovirus genus are transmitted by whiteflies and infect dicots. Mastreviruses and Curtoviruses have genomes comprising a single ssDNA component; Begomoviruses can have bipartite genomes comprising two similarly sized DNAs (usually termed A and B), as illustrated by African cassava mosaic virus (ACMV), tomato golden mosaic virus (TGMV), and potato yellow mosaic virus. However, monopartite begomoviruses that infect dicots are known, for example Tomato Yellow Leaf Curl Virus (TYLCV). The genomes of monopartite begomoviruses and curtoviruses have an arrangement of genes similar to the AL1, AL2 and AL3 genes found on the A DNA component of bipartite begomoviruses.

Geminiviruses infect a broad variety of plants and cause significant crop losses worldwide. However, very few geminivirus resistance genes have been found in plants, and those few that have remain uncharacterized. For at least these reasons, finding new genetic loci that confer resistance to these pathogens, especially broad resistance, would be a welcome discovery for the agricultural world. The presently disclosed subject matter addresses this need.

SUMMARY

This Summary lists several embodiments of the presently disclosed subject matter, and in many cases lists variations and permutations of these embodiments of the presently disclosed subject matter. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter relates to expression cassettes, in some embodiments heterologous expression cassettes. In some embodiments, an expression cassette of the presently disclosed subject matter comprises, consists essentially of, or consists of (i) a polynucleotide that encodes a polypeptide that is at least 96% identical to SEQ ID NO: 2; (ii) operably linked to a promoter that is functional in plants; and (iii) a transcription terminator. In some embodiments, the promoter is functional in a plant selected from the group consisting of tomato, cassava, and cotton. In some embodiments, the promoter is selected from the group consisting of an *Arabidopsis* translationally controlled tumor protein (AtTCTP) promoter, an *Arabidopsis* ubiquitin extension protein 1 (AtUBQ1) promoter, a cauliflower mosaic virus 35S promoter, and a duplicated 35S (2× 35S) promoter. In some embodiments, the AtTCTP promoter comprises, consists essentially of, or consists of a nucleotide sequence as set forth in SEQ ID NO: 29, the AtUBQ1 promoter comprises, consists essentially of, or consists of a nucleotide sequence as set forth in SEQ ID NO: 30, the cauliflower mosaic virus 35S promoter comprises, consists essentially of, or consists of a nucleotide sequence as set forth in SEQ ID NO: 31, and/or the 2× 35S promoter comprises, consists essentially of, or consists of a nucleotide sequence as set forth in SEQ ID NO: 32. In some embodiments, the transcription terminator is selected from the group consisting of an *Agrobacterium* NOS terminator and a pea rbcS (E9) terminator. In some embodiments, the *Agrobacterium* NOS terminator comprises, consists essentially of, or consists of a nucleotide sequence as set forth in SEQ ID NO: 33, and/or the pea rbcS (E9) terminator comprises, consists essentially of, or consists of a nucleotide sequence as set forth in SEQ ID NO: 34. In some embodiments, the polynucleotide encodes an amino acid sequence comprising, consisting essentially of, or consisting of SEQ ID NO: 2, operably linked to both the promoter and the transcription terminator.

In some embodiments, the polynucleotide further comprises a tag sequence in the same reading frame as the polynucleotide. In some embodiments, the tag sequence is present in the expression cassette (a) between the promoter and the polynucleotide, and/or (b) between the polynucleotide and the terminator. In some embodiments, the tag sequence encodes a peptide tag comprising an amino acid sequence selected from the group consisting of SEQ ID NOs: 6, 7, 20, 22, 24, 26, 28, or any combination thereof.

In some embodiments, the expression cassette comprises a promoter, a polynucleotide, a tag sequence, and a transcription terminator in 5' to 3' orientation selected from the group consisting of (a) SEQ ID NO: 30, SEQ ID NO: 1, SEQ ID NO: 35 or SEQ ID NO: 36, and SEQ ID NO: 34; (b) SEQ ID NO: 29, SEQ ID NO: 1, SEQ ID NO: 35 or SEQ ID NO: 36, and SEQ ID NO: 33; (c) SEQ ID NO: 32, SEQ ID NO: 1, SEQ ID NO: 35 or SEQ ID NO: 36, and SEQ ID NO: 34; and (d) SEQ ID NO: 29, SEQ ID NO: 1, SEQ ID NO: 19, and SEQ ID NO: 33.

In some embodiments, the expression cassette comprises a first promoter, a first polynucleotide, a first tag sequence, and a first transcription terminator, and a second promoter, a second polynucleotide, a second tag sequence, and a second transcription terminator. In some embodiments, the first promoter, first polynucleotide nucleotide sequence, first tag sequence, and first transcription terminator in 5' to 3' orientation are SEQ ID NO: 29, SEQ ID NO: 1, SEQ ID NO: 19, and SEQ ID NO: 33 and the second promoter, second polynucleotide nucleotide sequence, second tag sequence, and second transcription terminator in 5' to 3' orientation are SEQ ID NO: 30, SEQ ID NO: 1, SEQ ID NO: 35 or SEQ ID NO: 36, and SEQ ID NO: 34.

In some embodiments, the presently disclosed subject matter relates to recombinant vectors comprising an expression cassette as disclosed herein.

In some embodiments, the presently disclosed subject matter relates to cells comprising an expression cassette as disclosed herein.

In some embodiments, the presently disclosed subject matter relates to transgenic plants comprising an expression cassette as disclosed herein. In some embodiments, the transgenic plant is a dicot. In some embodiments, the transgenic plant is selected from the group consisting of tomato, cassava, and cotton, optionally wherein the promoter is a tomato, a cassava, or a cotton promoter.

In some embodiments, the presently disclosed subject matter relates to progeny and/or seed from a transgenic plant as disclosed herein.

The presently disclosed subject matter also relates in some embodiments to methods for altering geminivirus resistance of plants. In some embodiments, the methods comprise, consist essentially of, or consist of expressing in a plant an expression cassette as disclosed herein. In some embodiments, the plant is selected from the group consisting of tomato, cassava, and cotton, optionally wherein the promoter is a tomato, a cassava, or a cotton promoter.

The presently disclosed subject matter also relates in some embodiments to methods for suppressing virus-induced leaf chlorosis, leaf curling, or both in a plant. In some embodiments, the methods comprise, consist essentially of, or consist of expressing in a plant an expression cassette as disclosed herein. In some embodiments, the plant is selected from the group consisting of tomato, cassava, and cotton, optionally wherein the promoter is a tomato, cassava, or a cotton promoter.

Thus, it is an object of the presently disclosed subject matter to provide expression cassettes comprising polynucleotides encoding polypeptides that enhance resistance to geminiviruses and other pathogens including but not limited to those that cause tomato yellow leaf curl disease, cassava mosaic disease, and cotton leaf curl disease, operably linked to promoters and transcription terminators, and methods for modulating geminivirus resistance and suppressing virus-induced leaf chlorosis, leaf curling, or both in plants.

An object of the presently disclosed subject matter having been stated herein above, and which is achieved in whole or in part by the presently disclosed subject matter, other objects will become evident as the description proceeds when taken in connection with the accompanying Figures as best described herein below.

BRIEF DESCRIPTION OF THE FIGURES

FIG. 4 summarizes exemplary steps to characterize candidate genes. Transcriptomic analysis by RNA-Seq was used to obtain gene expression information in the GRP loci and help to pinpoint the candidate geminivirus resistance genes. RNAs were extracted from leaves of healthy Pla-1 or Col-0 plants or plants 4 days after local cabbage leaf curl virus (CaLCuV) infection with mock infection as control. cDNAs were generated with Oligo dT primers for library construction with NEBNext Ultra II Directional RNA Library Prep Kit for Illumina and sequencing was run in NovaSeq 6000 Sequencing System that produced 151-nt paired reads. The sequence reads were processed, mapped to the Col-0 or Ler-0 reference genome sequences, and counted using the HISAT2 software. Comparisons of RNA levels of the genes between samples were performed with the DESeq2 software package for R. The Pla-1 GRP-1 and GRP-2 loci contain 24 and 36 expressed genes, respectively. Of these 60 genes, 33 are considered candidate resistance genes because (1) they are found only in Pla-1 but not in Col-0 or encode proteins with different amino acid sequences from their counterparts in Col-0 (21 genes); or (2) they are upregulated in healthy and/or CaLCuV-infected Pla-1 than in Col-0 or by CaLCuV infection in Pla-1 (26 genes). NLR and RCD1, located in the GRP-1 and GRP-2 loci, respectively, encode proteins with polymorphisms between Pla-1 and Col-0, have higher expression in healthy Pla-1 plants than in Col-0 plant and are the only two genes showing higher expression in CaLCuV-infected Pla-1 than in Col-0 when controlled by mock infection.

FIG. 9A is a photograph showing CaLCuV infection of Col-0 transgenic lines homozygous for the empty cassette, NLR, RCD1, or NLR+RCD1 at 28 days post-infection (dpi). FIG. 9B is a bar graph of average symptom scores of independent Col-0 T3 lines carrying the empty cassette (bars 1 and 2 in each half of FIG. 9B; gray in a color version of FIG. 9B), NLR (bars 3-7 in each half of FIG. 9B; dark blue in a color version of FIG. 9B), RCD1 (bars 8 and 9 in each half of FIG. 9B; cream in a color version of FIG. 9B), or NLR+RCD1 (bars 10-12 in each half of FIG. 9B; light blue in a color version of FIG. 9B). The plants were scored separately for leaf curling (left half of FIG. 9B) and leaf chlorosis (right half of FIG. 9B). Plants transformed with the NLR expression cassettes did not show leaf chlorosis. FIG. 9C is a bar graph of average symptom scores TRV VIGS of the NLR overcame resistance in Pla-1. The asterisks indicate p-values of less than 0.05 using a Mann Whitney test. Mock: light gray bars; infected: orange bars.

FIGS. 10A and 10B are summaries of the sequence the Pla-1 NLR resistance gene polypeptide (FIG. 10A) and three-dimensional structure (FIG. 10B) of the Col-0-NLR gene polypeptide. In FIG. 10A, two isoforms are shown, one that includes and one that lacks the unusual integrated domain (UID). The different colors of the amino acids in the color version of FIG. 10A show the amino acids that make up the TIR (red; amino acids 11-185 of SEQ ID NO: 2), the NBS (green; amino acids 201-415 of SEQ ID NO: 2), the LRR (orange; amino acids 500-911 of SEQ ID NO: 2), and the UID (purple; amino acids 912-1164 of SEQ ID NO: 2). Amino acids highlighted in light blue indicate amino acids that are unique in Pla-NLR as compared to the AT1G31540 gene from A. thaliana Col-0 and the allele from the geminivirus susceptible Pla-0 accession: one (1) the TIR domain, 0 in the NBS domain, 18 in the LRR domain, and 11 in the UID domain. The underlined amino acids are present in the longer isoform but missing in the shorter isoform. In the latter, the amino acid sequence includes Lys-762 followed by the 14-amino acid sequence VSSSKLNIISKLFS (SEQ ID NO: 38, corresponds to amino acids 763-776 of SEQ ID NO: 4). FIG. 10B shows the three-dimensional structure of the longer isoform of the Col-NLR gene polypeptide as determined by AlphaFold three-dimensional prediction software (AlphaFold, accessible from the website of the EMBL-EBI, Cambridgeshire, United Kingdom). In FIG. 10B, the locations of the TIR, NBS, LRR, and UID domains are indicated. This predicted 3-D structure can be used as a proxy for the Pla-1 NLR protein since its amino acid sequence is 95.4% identical to the Col-0 AT1G31540 NLR protein. The sole amino acid difference in the TIR domain between Pla-1 (Ile-74 of SEQ ID NO: 2) and Col-0 (Lys-74 in the Col-0 longer isoform) is marked with an arrow. Like in Col-0, the three most closely related NLR sequences in cassava have a lysine at the equivalent position. Pla-1, on the other hand, includes a non-conservative isoleucine substitution at amino acid 74.

BRIEF DESCRIPTION OF THE SEQUENCE LISTING

Figure 1A:
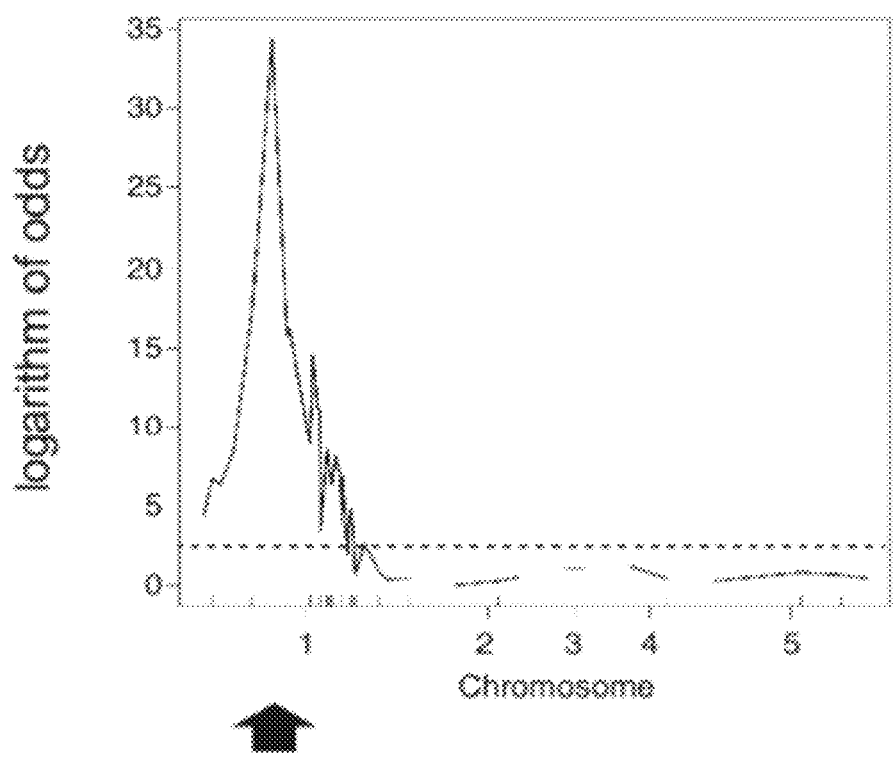
FIGS. 1A and 1B are graphical representations of the results of QTL mapping and KASP mapping, respectively, of Pla-1 resistance in *Arabidopsis*.

SEQ ID NOs: 1 and 2 are the nucleotide and amino acid sequences, respectively, of an exemplary Pla-1 longer isoform.

SEQ ID NOs: 3 and 4 are the nucleotide and amino acid sequences, respectively, of an exemplary Pla-1 shorter isoform.

SEQ ID NO: 5 is a nucleotide sequence of the Pla-1 genomic locus.

SEQ ID NO: 6 is the amino acid sequence of a V5 tag.

SEQ ID NO: 7 is the amino acid sequence of a second peptide tag.

SEQ ID NO: 8 is the reverse complement of nucleotides 11,288,378-11,293,799 of A. thaliana chromosome 1 as set forth in Accession No. NC_003070.9 of the GENBANK® biosequence database. It corresponds to the Col-0 AT1G31540 genetic locus.

SEQ ID NOs: 9 and 10 are the nucleotide and amino acid sequences, respectively, of an exemplary Col-0 longer isoform. SEQ ID NOs: 9 and 10 correspond to Accession Nos. NM_001123924.2 and NP_001117396.1 of the GENBANK® biosequence database.

SEQ ID NOs: 11 and 12 are the nucleotide and amino acid sequences, respectively, of an exemplary Col-0 shorter isoform. SEQ ID NOs: 9 and 10 correspond to Accession Nos. NM_001332968.1 and NP_001319123.1 of the GENBANK® biosequence database.

SEQ ID NOs: 13 and 14 are the nucleotide and amino acid sequences, respectively, of an exemplary Col-0 shorter isoform. SEQ ID NOs: 9 and 10 correspond to Accession Nos. NM_102893.3 and NP_174439.2 of the GENBANK® biosequence database.

SEQ ID NOs: 15 and 16 are the nucleotide sequences of exemplary PCR primers that can be employed together to place a C-terminal HA tag on the longer isoform of the Pla-1 resistance gene coding sequence.

SEQ ID NOs: 17 and 18 are the nucleotide and amino acid sequences, respectively, of the longer isoform of the Pla-1 resistance gene products with a C-terminal HA tag.

SEQ ID NO: 19 is a nucleic acid sequence that encodes an exemplary myc tag. SEQ ID NO: 20 is the amino acid sequence encoded by SEQ ID NO: 19.

SEQ ID NO: 21 is a nucleic acid sequence that encodes an exemplary His6 tag. SEQ ID NO: 22 is the amino acid sequence encoded by SEQ ID NO: 21.

SEQ ID NO: 23 is a nucleic acid sequence that encodes an exemplary FLAG tag.

SEQ ID NO: 24 is the amino acid sequence encoded by SEQ ID NO: 23.

SEQ ID NOs: 25 and 27 are nucleic acid sequences that encode exemplary E-tags.

SEQ ID NOs: 26 and 28 are the amino acid sequences encoded by SEQ ID NOs: 25 and 27, respectively.

SEQ ID NO: 29 is a nucleotide sequence of an *Arabidopsis* TCTP promoter.

SEQ ID NO: 30 is a nucleotide sequence of an *Arabidopsis* UBQ1 promoter.

SEQ ID NO: 31 is a nucleotide sequence of a cauliflower mosaic virus (CaMV) 35S promoter.

SEQ ID NO: 32 is a nucleotide sequence of a duplicated CaMV 35S promoter cassette.

SEQ ID NO: 33 is a nucleotide sequence of an *Agrobacterium* NOS terminator.

SEQ ID NO: 34 is a nucleotide sequence of a Pea rbcS (E9) terminator.

SEQ ID NOs: 35 and 36 are exemplary nucleic acid sequences that encode an exemplary human influenza hemagglutinin (HA) tag. SEQ ID NO: 37 is the amino acid sequence encoded by SEQ ID NOs: 35 and 36.

SEQ ID NO: 38 is the amino acid sequence VSSSTLNIISKLFP which is the C-terminal 14 amino acids of the Pla-1 shorter isoforms (corresponds to amino acids 763-776 of SEQ ID NO: 4).

DETAILED DESCRIPTION

I. General Considerations

A goal of functional genomics is to identify genes controlling expression of organismal phenotypes, and functional genomics employs a variety of methodologies including, but not limited to, bioinformatics, gene expression studies, gene and gene product interactions, genetics, biochemistry, and molecular genetics. For example, bioinformatics can assign function to a given gene by identifying genes in heterologous organisms with a high degree of similarity (homology) at the amino acid or nucleotide level. Studies of the expression of a gene at the mRNA or polypeptide levels can assign function by linking expression of the gene to an environmental response, a developmental process, or a genetic (mutational) or molecular genetic (gene overexpression or underexpression) perturbation. Expression of a gene at the mRNA level can be ascertained either alone (for example, by Northern analysis and/or quantitative PCR) or in concert with other genes (for example, by microarray analysis and/or next generation sequencing), whereas expression of a gene at the polypeptide level can be ascertained either alone (for example, by native or denatured polypeptide gel or immunoblot analysis) or in concert with other genes (for example, by proteomic analysis). Knowledge of polypeptide/polypeptide and polypeptide/DNA interactions can assign function by identifying polypeptides and nucleic acid sequences acting together in the same biological process. Genetics can assign function to a gene by demonstrating that DNA lesions (mutations) in the gene have a quantifiable effect on the organism, including, but not limited to, its development; hormone biosynthesis and response; growth and growth habit (plant architecture); mRNA expression profiles; polypeptide expression profiles; ability to resist diseases such as those associated with geminivirus infection; ability to acquire nutrients; photosynthetic efficiency; altered primary and secondary metabolism; and the composition of various plant organs. Biochemistry can assign function by demonstrating that the polypeptide(s) encoded by the gene, typically when expressed in a heterologous organism, possesses a certain functional activity, either alone or in combination with other polypeptides. Molecular genetics can assign function by studying the overexpression or underexpression of a gene in the native plant or in heterologous organisms, and observing quantifiable effects as disclosed in functional assignment by genetics above. In functional genomics, any or all of these approaches are utilized, often in concert, to assign functions to genes across any of a number of organismal phenotypes.

It is recognized by those skilled in the art that these different methodologies can each produce evidence for the function of a particular gene, and that such evidence is stronger as increasing amounts of data are used for functional assignment: in some embodiments from a single methodology, in some embodiments from two methodologies, and in some embodiments from more than two methodologies. In addition, those skilled in the art are aware that different methodologies can differ in the strength of the evidence provided for the assignment of gene function. Typically, but not always, a datum of biochemical, genetic, or molecular genetic evidence is considered stronger than a datum of bioinformatic or gene expression evidence. Finally, those skilled in the art recognize that for different genes, a single datum from a single methodology can differ in terms of the strength of the evidence provided by each distinct datum for the assignment of the function of these different genes.

The objective of crop trait functional genomics is to identify crop trait genes of interest, for example, genes capable of conferring useful agronomic traits in crop plants. Such agronomic traits include, but are not limited to, enhanced yield, whether in quantity or quality; enhanced nutrient acquisition and metabolic efficiency; enhanced or altered nutrient composition of plant tissues used for food, feed, fiber, or processing; enhanced utility for agricultural or industrial processing; enhanced resistance to plant diseases, such as diseases associated with geminivirus infection; and alterations in plant architecture or development, including changes in developmental timing. The deployment of such identified trait genes by either transgenic or non-transgenic means can materially improve crop plants for the benefit of agriculture.

Cereals are the most important crop plants on the planet in terms of both human and animal consumption. Genomic synteny (conservation of gene order within large chromosomal segments) is observed in rice, maize, wheat, barley, rye, oats, and other agriculturally important monocots, which facilitates the mapping and isolation of orthologous genes from diverse cereal species based on the sequence of a single cereal gene. Rice has the smallest (about 420 Mb) genome among the cereal grains, and has recently been a major focus of public and private genomic and EST sequencing efforts. See Goff et al., 2002.

In some embodiments of the presently disclosed subject matter and to identify crop trait genes in plant genomes controlling responses to biotic stress (e.g., infection with geminiviruses and its consequences), genes from plant draft genome sequences can be prioritized based on one or more functional genomic methodologies. For example, genome-wide expression studies of plants grown in the presence and absence of geminivirus can be used to prioritize candidate genes controlling geminivirus resistance. Full-length and partial cDNAs of trait gene candidates can then be analyzed based on analysis of the whole-genome sequence of the plant and isolated by designing and using primers for PCR amplification using a commercially available PCR primer-picking program. Primers can then be used for PCR amplification of full-length or partial cDNAs from cDNA libraries or first-strand cDNA. cDNA clones resulting from either approach can be used for the construction of vectors designed for altering expression of these genes in transgenic plants using plant molecular genetic methodologies. Alteration of plant phenotypes through overexpression or underexpression of key trait genes in transgenic plants is a robust and established method for assigning functions to plant genes. Assays to identify transgenic plants with alterations in traits of interest can be used to unambiguously assign the usefulness of these genes for the improvement of plants by transgenic and/or classical breeding methods.

However, in some embodiments commercially relevant dicots can also be modified using the compositions and methods of the presently disclosed subject matter. Such dicots include, but are not limited to, tomato, cassava, cotton, pepper, apples, banyan, bitter gourd, brinjal, lemon, mango, neem, *papaya*, soybean, sunflower, squash, broccoli, cauliflower, and tobacco.

The presently disclosed subject matter can be better understood by referring to the specification and Figures attached hereto. The components in the specification and Figures are not necessarily to scale, emphasis instead being placed upon illustrating the principles of the presently disclosed subject matter (often schematically). A further understanding of the presently disclosed subject matter can be obtained by reference to embodiments set forth in the illustrations of the accompanying specification and Figures. Although the illustrated embodiments are merely exemplary of systems for carrying out the presently disclosed subject matter, both the organization and method of operation of the presently disclosed subject matter, in general, together with further objectives and advantages thereof, may be more easily understood by reference to the specification and Figures. The Figures are not intended to limit the scope of this presently disclosed subject matter, but merely to clarify and exemplify the presently disclosed subject matter.

II. Definitions

Unless otherwise defined, all technical and scientific terms used herein have the same meaning as commonly understood by one of ordinary skill in the art to which the presently disclosed subject matter pertains. For clarity of the present specification, certain definitions are presented hereinbelow.

Following long-standing patent law convention, the terms "a" and "an" mean "one or more" when used in this application, including in the claims.

As used herein, the phrase "altered geminivirus resistance" refers to a state wherein a plant exhibits a different response to geminivirus exposure and/or infection than does another plant of the same species as a result of a manipulation of the plant's genome. In some embodiments, altered geminivirus resistance comprises enhanced resistance, wherein "enhanced geminivirus resistance" is defined as an increased ability of a plant (for example, a recombinant or transgenic plant) to withstand geminivirus exposure and/or infection as compared to a native plant of the same species. As used herein, the phrase "altering an geminivirus stress tolerance" refers in some embodiments to a manipulation of a plant's genome to produce a recombinant or transgenic plant in which the manipulation results in a change in the plant's resistance to geminivirus and consequences thereof, including but not limited to the development of leaf chlorosis and/or leaf curling. In some embodiments, altering an geminivirus resistance comprises enhancing a plant's resistance to geminivirus exposure and/or infection.

The term "amino acid" is used interchangeably with "amino acid residue", and may refer to a free amino acid and to an amino acid residue of a peptide. It will be apparent from the context in which the term is used whether it refers to a free amino acid or a residue of a peptide. Amino acids can be classified into seven groups on the basis of the side chain: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the presently disclosed subject matter follows the conventional practice wherein the amino group is presented to the left and the carboxy group to the right of each amino acid residue. In the formulae representing selected specific embodiments of the presently disclosed subject matter, the amino-and carboxy-terminal groups, although not specifically shown, will be understood to be in the form they would assume at physiologic pH values, unless otherwise specified.

As used herein, amino acids are represented by the full name thereof, by the three letter code corresponding thereto, or by the one-letter code corresponding thereto, as indicated in Table 1:

TABLE 1

Table of Amino Acids and Functionally Equivalent Codons

| Amino Acid | 3-Letter Code | 1-Letter Code | Codons |
|---|---|---|---|
| Alanine | Ala | A | GCA; GCC; GCG; GCU |
| Cysteine | Cys | C | UGC; UGU |
| Aspartic Acid | Asp | D | GAC; GAU |
| Glutamic acid | Glu | E | GAA; GAG |
| Phenylalanine | Phe | F | UUC; UUU |
| Glycine | Gly | G | GGA; GGC; GGG; GGU |
| Histidine | His | H | CAC; CAU |
| Isoleucine | Ile | I | AUA; AUC; AUU |
| Lysine | Lys | K | AAA; AAG |
| Leucine | Leu | L | UUA; UUG; CUA; CUC; CUG; CUU |
| Methionine | Met | M | AUG |
| Asparagine | Asn | N | AAC; AAU |
| Proline | Pro | P | CCA; CCC; CCG; CCU |
| Glutamine | Gln | Q | CAA; CAG |
| Arginine | Arg | R | AGA; AGG; CGA; CGC; CGG; CGU |
| Serine | Ser | S | ACG; AGU; UCA; UCC; UCG; UCU |
| Threonine | Thr | T | ACA; ACC; ACG; ACU |
| Valine | Val | V | GUA; GUC; GUG; GUU |
| Tryptophan | Trp | W | UGG |
| Tyrosine | Tyr | Y | UAC; UAU |

As used herein, the terms "associated with" and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked or situated such that the regulator DNA sequence can affect the expression level of the coding or structural DNA sequence.

As used herein, the term "chimera" refers to a nucleic acid or polypeptide that encodes or comprises domains or other features that are derived from different nucleic acids or polypeptides or are in a position relative to each other that is not naturally occurring.

As used herein, the term "chimeric construct" refers to a recombinant nucleic acid molecule in which a promoter or regulatory nucleic acid sequence is operatively linked to, or associated with, a nucleic acid sequence that codes for an mRNA or which is expressed as a polypeptide, such that the regulatory nucleic acid sequence is able to regulate transcription or expression of the associated nucleic acid sequence. The regulatory nucleic acid sequence of the chimeric construct is not normally operatively linked to the associated nucleic acid sequence as found in nature.

As used herein, the term "co-factor" refers to a natural reactant, such as an organic molecule or a metal ion, required in an enzyme-catalyzed reaction. A co-factor can be, for example, NAD(P), riboflavin (including FAD and FMN), folate, molybdopterin, thiamin, biotin, lipoic acid, pantothenic acid, and coenzyme A, S-adenosylmethionine, pyridoxal phosphate, ubiquinone, and menaquinone. In some embodiments, a co-factor can be regenerated and reused.

As used herein, the terms "coding sequence" and "open reading frame" (ORF) are used interchangeably and refer to a nucleic acid sequence that is transcribed into RNA such as mRNA, rRNA, tRNA, snRNA, sense RNA, or antisense RNA. In some embodiments, the RNA is then translated in vivo or in vitro to produce a polypeptide.

As used herein, the term "complementary" refers to two nucleotide sequences that comprise antiparallel nucleotide sequences capable of pairing with one another upon formation of hydrogen bonds between the complementary base residues in the antiparallel nucleotide sequences. As is known in the art, the nucleic acid sequences of two complementary strands are the reverse complement of each other when each is viewed in the 5' to 3' direction. Unless specifically indicated to the contrary, the term "complementary" as used herein refers to 100% complementarity throughout the length of at least one of the two antiparallel nucleotide sequences.

As used herein, the terms "domain" and "feature", when used in reference to a polypeptide or amino acid sequence, refers to a subsequence of an amino acid sequence that has a particular biological function. Domains and features that have a particular biological function include, but are not limited to, ligand binding, nucleic acid binding, catalytic activity, substrate binding, and polypeptide-polypeptide interacting domains. Similarly, when used herein in reference to a nucleic acid sequence, a "domain" or "feature" is that subsequence of the nucleic acid sequence that encodes a domain or feature of a polypeptide. Particularly with reference to a nucleic acid molecule, a "domain" or "feature" is also intended to encompass nucleotide sequences that have a function apart from encoding a domain or feature of a polypeptide. For example, a nucleotide sequence that binds a polypeptide can also be a "domain" (in this case, a protein binding domain).

As used herein, the term "enzyme activity" refers to the ability of an enzyme to catalyze the conversion of a substrate into a product. A substrate for the enzyme can comprise the natural substrate of the enzyme but also can comprise analogues of the natural substrate, which can also be converted by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme can also be measured by determining the amount of an unused co-factor of the reaction remaining in the reaction mixture after a certain period of time or by determining the amount of used co-factor in the reaction mixture after a certain period of time. The activity of the enzyme can also be measured by determining the amount of a donor of free energy or energy-rich molecule (e.g. ATP, phosphoenolpyruvate, acetyl phosphate, or phosphocreatine) remaining in the reaction mixture after a certain period of time or by determining the amount of a used donor of free energy or energy-rich molecule (e.g. ADP, pyruvate, acetate, or creatine) in the reaction mixture after a certain period of time.

As used herein, the term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example an antisense RNA or a non-translated RNA in the sense or antisense direction.

As used herein, the term "functional" in the context of a promoter, transcriptional terminator, or any other element of an expression cassette, refers to an element that performs the same biological activity in a transgenic plant as that element performs or would perform in the plant from which it is derived. By way of example and not limitation, a "functional promoter" is a promoter that directs transcription of an operably linked polynucleotide, a "functional transcription terminator" is a transcription terminator that terminates transcription of an operably linked polynucleotide, etc. In the context of an expression cassette, a "functional expression cassette" is one that when introduced into a plant to create a transgenic plant, expresses the polynucleotide (in some embodiments, the coding sequence or open reading frame present therein) present therein in a detectable amount.

In some embodiments, the expression cassette is a "heterologous expression cassette", which refers to an expression cassette comprising nucleotide sequences that are derived from at least two different species. In some embodiments, a heterologous expression cassette of the presently disclosed subject matter comprises a promoter, a polynucleotide encoding a polypeptide of interest, and a transcription terminator, wherein the promoter, the polynucleotide, and the transcription terminator are not all naturally occurring in a single plant genus, species, accession, or ecotype.

The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. Typically, however, the expression cassette is heterologous with respect to the host; i.e., the particular DNA sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus. In the case of a multicellular organism such as a plant, the promoter can also be specific to a particular cell type, tissue, organ, or stage of development.

As used herein, the term "fragment" refers to a sequence that comprises a subset of another sequence. When used in the context of a nucleic acid or amino acid sequence, the terms "fragment" and "subsequence" are used interchangeably. A fragment of a nucleic acid sequence can be any number of nucleotides that is less than that found in another nucleic acid sequence, and thus includes, but is not limited to, the sequences of an exon or intron, a promoter, an enhancer, an origin of replication, a 5' or 3' untranslated region, a coding region, and/or a polypeptide binding domain. It is understood that a fragment or subsequence can also comprise less than the entirety of a nucleic acid sequence, for example, a portion of an exon or intron, promoter, enhancer, etc. Similarly, a fragment or subsequence of an amino acid sequence can be any number of residues that is less than that found in a naturally occurring polypeptide, and thus includes, but is not limited to, domains, features, repeats, etc. Also similarly, it is understood that a fragment or subsequence of an amino acid sequence need not comprise the entirety of the amino acid sequence of the domain, feature, repeat, etc. A fragment can also be a "functional fragment", in which the fragment retains a specific biological function of the nucleic acid sequence or amino acid sequence of interest. For example, a functional fragment of a transcription factor can include, but is not limited to, a DNA binding domain, a transactivating domain, or both. Similarly, a functional fragment of a receptor tyrosine kinase includes, but is not limited to a ligand binding domain, a kinase domain, an ATP binding domain, and combinations thereof.

As used herein, the term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The terms "heterologous", "recombinant", and "exogenous", when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or other recombinant techniques. The terms also include non-naturally occurring multiple copies of a naturally occurring DNA sequence. Thus, the terms refer to a DNA segment that is foreign to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

An "endogenous" or "native" nucleic acid (or amino acid) sequence is a nucleic acid (or amino acid) sequence naturally associated with a host cell into which it is introduced. In this context, the terms "heterologous" and "endogenous" are antonymous.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. The phrase "bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

As used herein, the term "inhibitor" refers to a chemical substance that inactivates or decreases the biological activity of a polypeptide such as a biosynthetic and catalytic activity, receptor, signal transduction polypeptide, structural gene product, or transport polypeptide. The term "herbicide" (or "herbicidal compound") is used herein to define an inhibitor applied to a plant at any stage of development, whereby the herbicide inhibits the growth of the plant or kills the plant.

As used herein, the term "isolated", when used in the context of an isolated nucleic acid or an isolated polypeptide, is a nucleic acid or polypeptide that, by the hand of man, exists apart from its native environment and is therefore not a product of nature. An nucleic acid molecule or polypeptide can exist in a purified form or can exist in a non-native environment such as, for example, in a transgenic host cell.

As used herein, the term "mature polypeptide" refers to a polypeptide from which the transit peptide, signal peptide, and/or propeptide portions have been removed.

As used herein, the term "minimal promoter" refers to the smallest piece of a promoter, such as a TATA element, that can support any transcription. A minimal promoter typically has greatly reduced promoter activity in the absence of upstream or downstream activation. In the presence of a suitable transcription factor, a minimal promoter can function to permit transcription.

As used herein, the term "modified enzyme activity" refers to enzyme activity that is different from that which naturally occurs in a plant (i.e. enzyme activity that occurs naturally in the absence of direct or indirect manipulation of such activity by man). In some embodiments, a modified enzyme activity is displayed by a non-naturally occurring enzyme that is tolerant to inhibitors that inhibit the cognate naturally occurring enzyme activity.

As used herein, the term "native" refers to a gene that is naturally present in the genome of an untransformed plant cell. Similarly, when used in the context of a polypeptide, a "native polypeptide" is a polypeptide that is encoded by a native gene of an untransformed plant cell's genome. Thus, the terms "native" and "endogenous" are synonymous.

As used herein, the term "naturally occurring" refers to an object that is found in nature as distinct from being artificially produced or manipulated by man. For example, a polypeptide or nucleotide sequence that is present in an organism (including a virus) in its natural state, which has not been intentionally modified or isolated by man in the laboratory, is naturally occurring. As such, a polypeptide or nucleotide sequence is considered "non-naturally occurring" if it is encoded by or present within a recombinant molecule, even if the amino acid or nucleic acid sequence is identical to an amino acid or nucleic acid sequence found in nature.

As used herein, the term "nucleic acid" refers to deoxyribonucleotides or ribonucleotides and polymers thereof in either single or double stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions can be achieved by generating sequences in which the third position of one or more selected (or all) codons is substituted with mixed base and/or deoxyinosine residues (Batzer et al., 1991; Ohtsuka et al., 1985; Rossolini et al., 1994). The terms "nucleic acid" or "nucleic acid sequence" can also be used interchangeably with gene, cDNA, and mRNA encoded by a gene.

As used herein, the term "operably" as in "operably linked" refers to a functional linkage between a first sequence (e.g., a promoter) and a second sequence (e.g., a coding sequence), wherein the first sequence influences a biological event (e.g., transcription, transcription, replication, etc.) that occurs with respect to the second sequence. Generally, operably linked means that the nucleotide sequences being linked are contiguous in a single molecule. Examples of nucleotide sequences that can be operably linked in, for example, expression cassettes include promoters, coding sequences, and transcription terminators.

As used herein, the phrase "percent identical", in the context of two nucleic acid or polypeptide sequences, refers to two or more sequences or subsequences that have in some embodiments 60%, in some embodiments 70%, in some embodiments 80%, in some embodiments 90%, in some embodiments 95%, and in some embodiments at least 99% nucleotide or amino acid residue identity, respectively, when compared and aligned for maximum correspondence, as measured using one of the following sequence comparison algorithms or by visual inspection. The percent identity exists in some embodiments over a region of the sequences that is at least about 50 residues in length, in some embodiments over a region of at least about 100 residues, and in some embodiments, the percent identity exists over at least about 150 residues. In some embodiments, the percent identity exists over the entire length of the sequences.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm disclosed in Smith & Waterman, 1981, by the homology alignment algorithm disclosed in Needleman & Wunsch, 1970, by the search for similarity method disclosed in Pearson & Lipman, 1988, by computerized implementations of these algorithms (GAP, BESTFIT, FASTA, and TFASTA in the GCG® WISCONSIN PACKAGE® (Womble, 2000), available from Accelrys, Inc., San Diego, California, United States of America), or by visual inspection. See generally, Altschul et al., 1990; Ausubel et al., 2002 and Ausubel et al., 2003.

One example of an algorithm that is suitable for determining percent sequence identity and sequence similarity is the BLAST algorithm, which is described in Altschul et al., 1990. Software for performing BLAST analysis is publicly available through the website of the National Center for Biotechnology Information. This algorithm involves first identifying high scoring sequence pairs (HSPs) by identifying short words of length W in the query sequence, which either match or satisfy some positive valued threshold score T when aligned with a word of the same length in a database sequence. T is referred to as the neighborhood word score threshold. See generally, Altschul et al., 1990. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences (see e.g., Karlin & Altschul, 1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

As used herein, the term "shuffled nucleic acid" refers to a recombinant nucleic acid molecule in which the nucleotide sequence comprises a plurality of nucleotide sequence fragments, wherein at least one of the fragments corresponds to a region of a nucleotide sequence listed in SEQ ID NO: 1, 3, or 17, and wherein at least two of the plurality of sequence fragments are in an order, from 5' to 3', which is not an order in which the plurality of fragments naturally occur in a nucleic acid The term "substantially identical", in the context of two nucleotide or amino acid sequences, refers to two or more sequences or subsequences that have in some embodiments at least about 60% nucleotide or amino acid identity, in some embodiments at least about 65% nucleotide or amino acid identity, in some embodiments at least about 70% nucleotide or amino acid identity, in some embodiments at least about 75% nucleotide or amino acid identity, in some embodiments at least about 80% nucleotide or amino acid identity, in some embodiments at least about 85% nucleotide or amino acid identity, in some embodiments at least about 90% nucleotide or amino acid identity, in some embodiments at least about 91% nucleotide or amino acid identity, in some embodiments at least about 92% nucleotide or amino acid identity, in some embodiments at least about 93% nucleotide or amino acid identity, in some embodiments at least about 94% nucleotide or amino acid identity, in some embodiments at least about 95% nucleotide or amino acid identity, in some embodiments at least about 96% nucleotide or amino acid identity, in some embodiments at least about 97% nucleotide or amino acid identity, in some embodiments at least about 98% nucleotide or amino acid identity, in some embodiments at least about 99% nucleotide or amino acid identity, and in some embodiments at least about 100% nucleotide or amino acid identity, when compared and aligned for maximum correspondence, as measured using one of the above-referenced sequence comparison algorithms or by visual inspection. In one example, the substantial identity exists in nucleotide or amino acid sequences of at least 50 residues, in another example in nucleotide or amino acid sequence of at least about 100 residues, in another example in nucleotide or amino acid sequences of at least about 150 residues, and in yet another example in nucleotide or amino acid sequences comprising complete coding sequences or complete amino acid sequences.

In some embodiments, two nucleic acid or amino acid sequences that are substantially identical also have the same function. In these embodiments, the phrase "the same function" applies to two or more nucleic acid molecules or polypeptides that perform the same biochemical role in either different cell types in the same plant, similar cell types in the same plant, similar cell types in different plants, or even different cell types in different plants. Exemplary functions include, but are not limited to kinase activity, phosphatase activity, nucleic acid binding activity, heat shock activity, and any other enzymatic activity. Two nucleic acids or polypeptides are also deemed to have "the same function" if they participate in the same step of a biochemical pathway, bind to the same, or similar substrates, or produce the same or similar products as a result of their biochemical activities. Exemplary non-limited pathways in which the nucleic acids and polypeptides of the presently disclosed subject matter can function include carbon metabolism, photosynthesis, signal transduction, cell growth, reproduction, disease processes, gene regulation, and resistance to geminivirus-associated disease and its consequences.

In one aspect, polymorphic sequences can be substantially identical sequences. The term "polymorphic" refers to the two or more genetically determined alternative sequences or alleles in a population. An allelic difference can be as small as one base pair. Nonetheless, one of ordinary skill in the art would recognize that the polymorphic sequences correspond to the same gene.

Another indication that two nucleotide sequences are substantially identical is that the two molecules specifically or substantially hybridize to each other under conditions of medium or high stringency. In the context of nucleic acid hybridization, two nucleic acid sequences being compared can be designated a "probe sequence" and a "target sequence". A "probe sequence" is a reference nucleic acid molecule, and a "'target sequence" is a test nucleic acid molecule, often found within a heterogeneous population of nucleic acid molecules. A "target sequence" is synonymous with a "test sequence".

An exemplary nucleotide sequence employed for hybridization studies or assays includes probe sequences that are complementary to or mimic in some embodiments at least an about 14 to 40 nucleotide sequence of a nucleic acid molecule of the presently disclosed subject matter. In one example, probes comprise 14 to 20 nucleotides, or even longer where desired, such as 30, 40, 50, 60, 100, 200, 300, or 500 nucleotides or up to the full length (for example, the full complement) of any of the nucleic acid sequence set forth in the SEQ ID NO: 1, 3, or 17. Such fragments can be readily prepared by, for example, directly synthesizing the fragment by chemical synthesis, by application of nucleic acid amplification technology, or by introducing selected sequences into recombinant vectors for recombinant production.

The phrase "hybridizing substantially to" refers to complementary hybridization between a probe nucleic acid molecule and a target nucleic acid molecule and embraces minor mismatches (for example, polymorphisms) that can be accommodated by reducing the stringency of the hybridization and/or wash media to achieve the desired hybridization.

"Stringent hybridization conditions" and "stringent hybridization wash conditions" in the context of nucleic acid hybridization experiments such as Southern and Northern blot analyses, are both sequence- and environment-dependent. Longer sequences hybridize specifically at higher temperatures. An extensive guide to the hybridization of nucleic acids is found in Tijssen, 1993. Generally, high stringency hybridization and wash conditions are selected to be about 5° C. lower than the thermal melting point (Tm) for the specific sequence at a defined ionic strength and pH. Typically, under "highly stringent conditions" a probe will hybridize specifically to its target subsequence, but to no other sequences. Similarly, medium stringency hybridization and wash conditions are selected to be more than about 5° C. lower than the Tm for the specific sequence at a defined ionic strength and pH. Exemplary medium stringency conditions include hybridizations and washes as for high stringency conditions, except that the temperatures for the hybridization and washes are in some embodiments 8° C., in some embodiments 10° C., in some embodiments 12° C., and in some embodiments 15° C. lower than the Tm for the specific sequence at a defined ionic strength and pH.

The Tm is the temperature (under defined ionic strength and pH) at which 50% of the target sequence hybridizes to a perfectly matched probe. Very stringent conditions are selected to be equal to the Tm for a particular probe. An example of highly stringent hybridization conditions for Southern or Northern Blot analysis of complementary nucleic acids having more than about 100 complementary residues is overnight hybridization in 6×SSC (or 6×SSPE)/ 0.5% SDS at 65° C., or the same solution including 50% formamide at 42° C. An example of highly stringent wash conditions is 15 minutes in 0.1× standard saline citrate (SSC), 0.1% (w/v) SDS at 65° C. Another example of highly stringent wash conditions is 15 minutes in 0.2×SSC buffer at 65° C. (see Sambrook & Russell, 2001 for a description of SSC buffer and other stringency conditions). Often, a high stringency wash is preceded by a lower stringency wash to remove background probe signal. An example of medium stringency wash conditions for a duplex of more than about 100 nucleotides is 15 minutes in 1×SSC at 55° C. Another example of medium stringency wash conditions for a duplex of more than about 100 nucleotides is 15 minutes in 1×SSC at 50° C. Another example of medium stringency wash conditions for a duplex of more than about 100 nucleotides is 15 minutes in 1×SSC at 45° C. An example of medium stringency wash conditions for a duplex of more than about 100 nucleotides is 15 minutes in 1×SSC at 40° C. Another example of medium stringency wash for a duplex of more than about 100 nucleotides is 15 minutes in 4-6×SSC at 40° C. Another example of medium stringency wash for a duplex of more than about 100 nucleotides is 15 minutes in 4-6× SSC at 40° C. For short probes (e.g., about 10 to 50 nucleotides), stringent conditions typically involve salt concentrations of less than about 1M Na$^+$ ion, typically about 0.01 to 1M Na$^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to clone homologous nucleotide sequences that are substantially identical to reference nucleotide sequences of the presently disclosed subject matter: a probe nucleotide sequence hybridizes in one example to a target nucleotide sequence in 7% sodium dodecyl sulfate (SDS), 0.5M NaPO$_4$, 1 mm ethylene diamine tetraacetic acid (EDTA), 1% BSA at 50° C. followed by washing in 2×SSC, 0.1% SDS at 50° C.; in another example, a probe and target sequence hybridize in 7% SDS, 0.5 M NaPO$_4$, 1 mm EDTA, 1% BSA at 50° C. followed by washing in 1×SSC, 0.1% SDS at 50° C.; in another example, a probe and target sequence hybridize in 7% SDS, 0.5 M NaPO$_4$, 1 mm EDTA, 1% BSA at 50° C. followed by washing in 0.5×SSC, 0.1% SDS at 50° C.; in another example, a probe and target sequence hybridize in 7% SDS, 0.5 M NaPO$_4$, 1 mm EDTA, 1% BSA at 50° C. followed by washing in 0.1×SSC, 0.1% SDS at 50° C.; in yet another example, a probe and target sequence hybridize in 7% SDS, 0.5 M NaPO$_4$, 1 mm EDTA, 1% BSA at 50° C. followed by washing in 0.1×SSC, 0.1% SDS at 65° C. In some embodiments, hybridization conditions comprise hybridization in a roller tube for at least 12 hours at 42° C. In each of the above conditions, the sodium phosphate hybridization buffer can be replaced by a hybridization buffer comprising 6×SSC (or 6×SSPE), 5×Denhardt's reagent, 0.5% SDS, and 100 g/ml carrier DNA, including 0-50% formamide, with hybridization and wash temperatures chosen based upon the desired stringency. Other hybridization and wash conditions are known to those of skill in the art (see also Sambrook & Russell, 2001; Ausubel et al., 2002; and Ausubel et al., 2003, each of which is incorporated herein in its entirety). As is known in the art, the addition of formamide in the hybridization solution reduces the Tm by about 0.4° C. Thus, high stringency conditions include the use of any of the above solutions and 0% formamide at 65° C., or any of the above solutions plus 50% formamide at 42° C.

As used herein, the term "pre-polypeptide" refers to a polypeptide that is normally targeted to a cellular organelle, such as a chloroplast, and still comprises a transit peptide.

As used herein, the terms "purified" and "isolated", when applied to a nucleic acid or polypeptide, denotes that the nucleic acid or polypeptide is essentially free of other cellular components with which it is associated in the natural state. It can be in a homogeneous state although it can be in either a dry or aqueous solution. Purity and homogeneity are typically determined using analytical chemistry techniques such as polyacrylamide gel electrophoresis or high performance liquid chromatography. A polypeptide that is the predominant species present in a preparation is substantially purified. The term "purified" denotes that a nucleic acid or polypeptide gives rise to essentially one band in an electrophoretic gel. Particularly, it means that the nucleic acid or polypeptide is in some embodiments at least about 50% pure, in some embodiments at least about 85% pure, and in some embodiments at least about 99% pure.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross over oligonucleotide. For indirect recombination, no more than one of the sequences is an actual substrate for recombination, and in some cases, neither sequence is a substrate for recombination.

As used herein, the term "regulatory elements" refers to nucleotide sequences involved in controlling the expression of a nucleotide sequence. Regulatory elements can comprise a promoter operatively linked to the nucleotide sequence of interest and termination signals. Regulatory sequences also include enhancers and silencers. They also typically encompass sequences required for proper translation of the nucleotide sequence.

As used herein, the term "significant increase" refers to an increase in activity (for example, enzymatic activity) that is larger than the margin of error inherent in the measurement technique, in some embodiments an increase by about 2 fold or greater over a baseline activity (for example, the activity of the wild type enzyme in the presence of the inhibitor), in some embodiments an increase by about 5 fold or greater, and in some embodiments an increase by about 10 fold or greater.

As used herein, the terms "significantly less" and "significantly reduced" refer to a result (for example, an amount of a product of an enzymatic reaction) that is reduced by more than the margin of error inherent in the measurement technique, in some embodiments a decrease by about 2 fold or greater with respect to a baseline activity (for example, the activity of the wild type enzyme in the absence of the inhibitor), in some embodiments, a decrease by about 5 fold or greater, and in some embodiments a decrease by about 10 fold or greater.

As used herein, the terms "specific binding" and "immunological cross-reactivity" refer to an indicator that two molecules are substantially identical. An indication that two nucleic acid sequences or polypeptides are substantially identical is that the polypeptide encoded by the first nucleic acid is immunologically cross reactive with, or specifically binds to, the polypeptide encoded by the second nucleic acid. Thus, a polypeptide is typically substantially identical to a second polypeptide, for example, where the two polypeptides differ only by conservative substitutions.

The phrase "specifically (or selectively) binds to an antibody", or "specifically (or selectively) immunoreactive with", when referring to a polypeptide or peptide, refers to a binding reaction which is determinative of the presence of the polypeptide in the presence of a heterogeneous population of polypeptides and other biologics. Thus, under designated immunoassay conditions, the specified antibodies bind to a particular polypeptide and do not bind in a significant amount to other polypeptides present in the sample. Specific binding to an antibody under such conditions can require an antibody that is selected for its specificity for a particular polypeptide. For example, antibodies raised to the polypeptide with the amino acid sequence encoded by any of the nucleic acid sequences of the presently disclosed subject matter can be selected to obtain antibodies specifically immunoreactive with that polypeptide and not with other polypeptides except for polymorphic variants. A variety of immunoassay formats can be used to select antibodies specifically immunoreactive with a particular polypeptide. For example, solid phase ELISA immunoassays, Western blots, or immunohistochemistry are routinely used to select monoclonal antibodies specifically immunoreactive with a polypeptide. See Harlow & Lane, 1988, for a description of immunoassay formats and conditions that can be used to determine specific immunoreactivity. Typically, a specific or selective reaction will be at least twice background signal or noise and more typically more than 10 to 100 times background.

As used herein, the term "subsequence" refers to a sequence of nucleic acids or amino acids that comprises a part of a longer sequence of nucleic acids or amino acids (e.g., polypeptide), respectively.

As used herein, the term "substrate" refers to a molecule that an enzyme naturally recognizes and converts to a product in the biochemical pathway in which the enzyme naturally carries out its function; or is a modified version of the molecule, which is also recognized by the enzyme and is converted by the enzyme to a product in an enzymatic reaction similar to the naturally-occurring reaction.

As used herein, the term "suitable growth conditions" refers to growth conditions that are suitable for a certain desired outcome, for example, the production of a recombinant polypeptide or the expression of a nucleic acid molecule.

As used herein, the term "transformation" refers to a process for introducing heterologous DNA into a plant cell, plant tissue, or plant. Transformed plant cells, plant tissue, or plants are understood to encompass not only the end product of a transformation process, but also transgenic progeny thereof.

As used herein, the terms "transformed", "transgenic", and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

As used herein, the term "viability" refers to a fitness parameter of a plant. Plants are assayed for their homozygous performance of plant development, indicating which polypeptides are essential for plant growth.

III. Nucleic Acid Molecules and Polypeptides of the Presently Disclosed Subject Matter III.A. Description of the Sequences In some embodiments, the presently disclosed subject matter relates to nucleic acid sequences encoding gene products that confer partial or complete resistance to geminiviruses and/or that, when present in and/or introduced into a plant that is susceptible to a disease associated with geminivirus infection (including but not limited to tomato yellow leaf curl disease, cassava mosaic disease, and cotton leaf curl disease) reduce the incidence or severity of the disease. Exemplary such sequences are members of the disease resistance protein (TIR-NBS-LRR class) family (NLR), or modified derivatives thereof.

In some embodiments, the genes and gene products are referred to as "Pla-1 homolog of AT1G31540.2" or "Pla-1", which has the following genomic sequence.

(SEQ ID NO: 5)

agaattcctaagacccagttggaggactaatgacattgccacacatataacaaaagagac ggtaaaacatgattcaattgattaataaaataaaaagtttagaaatcttctcctatttga taaaaatgatggattcttcttccaaaggtgtttacaatgaagaaaaaatgttgagtgtta aaagtagatttctagagatctttaatctaaatgtatatatattttggaaaatggtccggt tacatggatagtatgttaagattgttagactattggtaatatgtagatttatttatttaa -continued atactttcatttgggacaaaactaaaattacaggttgtggggtttgggaaattacgagtt atggtacagcgttcattgaattcaacgatcttgcgagagatacttcagtatccttccagc tggacacacgttttcaggtaacccaaaaatctcatacaccagtggcttattttagtttta caccaattgcgataatgtaatgacttagcttcttcatagtcaaatctcttgttgtttagc atatgattcgaacttcttttgtagaaaatatatagactgcaataacgcagcttttactct attttcagtctattatattgttcagcaagtggttgatagtatcaacgtgatacttattac ttaatagagttccaacatgaatacagattcagaaccaagactaagcaatgcatgatttat tttattttgattaaataaatcttaaaaaaatagcatcaaaattagattatctttgttca tgttgacaatatttacattttaacacaaataagtccttgtttaaaatctttccaaatgtg tgtcttattagttctaataggtaaaatgtgtaaagaaaccatcaccttttccaaaaacat gtaaaacaccgtcaactattttgtgggtttttaagctctcaccttttttaaaatggtaa aataacacctatgattattaaattaatttaaaataagacaaaataaatataaataataaa agtaatttggtttaagatttatttttcctaaaatttcaaaagttagaacaaatttgaacaa aaataaaattaaatatgctaagctataaactagttttagtttacataacgatttgtaatg gcaatgaaacttacttttatatcgcaaaaaccaacaactaaatactggaaaagaaatc gaactcgaatttgaaatagataaatacaaaataaattgttttatttatgtttcaaaataa tagtttatttgatatttatttggtttgataatattagatgttatattaccatttttaaa aggtgagggtttaaataccaaaagaaaagttgacggttttttacatgttattggataaag gagaggttttttttacccattttccgttctaatataatgattattttgctatttctcac agtaaactcatgttgcccataatgtgagagtacttctccacaaatcctctcctttgcata aaatgagaagcacatctactggatttggagtatgatgagctatacatatttattaagaat atgtaaatgaatgagatagtaatgtaaagacaagaggctatgaaagatggttgtgaccac tgagtcaacaaagaggaaacttccgccaagttgcatcagaaaagtctaagaaatgattgc gaaaacttgtgtggccgtgattaagtcaagttacctctcagctgttatgttaaatgtttt atatccaccaagacagactcactacttctcctctatttctcttcttaaaagtcttcgttc cttgtttcctccttctaaCTCTCTCTCTCTCT*ATG*GCTTCTTCATCTTCTTCTCACAATT

GGTTATATGATGTTTTCTTGAGCTTCAGAGGGGAAGACGTCCGCGTAACATTCCGTAGCC

ACTTTCTCAAAGAGCTTGATCGGAAACTAATCACTGCTTTCAGAGACAATGAGATCGAGA

GAAGCCACTCTCTCTGGCCCGATCTTGAACAAGCCATCAAGGAATCCAGGATCGCTGTGG

TCGTTTTCTCCATAAACTACGCTTCATCGAGCTGGTGTCTTAACGAGTTGCTGGAGATTG

TAAACTGCAATGATAAAATTGTCATACCAGTTTTCTACCATGTGGATCCTTCACAAGTGA

GGCATCAAATCGGCGACTTCGGAAAGATCTTTGAAAATACTTGCAAGAGACAAACAGATG

AGGAAGTGAAAAATCAATGGAAGAAAGCGCTGACTCTTGTAGCGAATATGCTTGGATTTG

ACTCTGCCAAATGgtatgttttttttaattattagatacatcttgaaataaattgttgt ttcatatttgttaaattatctttcatcttattagGAACGACGAAGCAAAAATGATTGAAG

AAATAGCCAATGATGTTTGGGTAAACTGCTTTTAACTACACCTAAGGATTCTGAGGAAC

TTGTTGGCATCGAAGATCACATCGCTGAAATGAGTTTACTGCTGCAACTGGAATCTGAAG

AAGTGAGAATGGTTGGTATATCGGGTTCCTCAGGGATTGGTAAGACTACCATTGCAAGAG

CTCTGTTTAAACGACTTTCTCGACATTTCCAAGGTAGCACTTTCATCGACAGGGCTTTTG

TATCTTATAGTCGGAATATTTATAGTGGCGCCAATCCGGACGACCCCAATATGAAGTTGC

-continued

```
AGCTACAAGGACACTTCCTATCTGAAATTCTCGGCAAAAAGGACATAAAGATAGATGATC
CAGCTGCACTGGAAGAGAGGCTAAAGCACCAAAAAGTTCTTATCATTATTGATGATTTGG
ATGATATAATGGTACTAGATACATTAGTGGGTCAAACTCAATGGTTTGGATATGGGAGCA
GAATCATTGTGGTTACAAATGATAAGCACTTCTTGATTGCTCATGGAATTGATCATATTT
ATGAAGTAAGTTTCCCAACTGATGTGCATGCTTGTCAGATGTTATGTCAATCTGCATTCA
AGCAAAACTATGCTCCTAAAGGTTTTGAGGATCTTGTAGTTGATGTAGTAAGACATGCGG
GCAATTTTCCTTTGGGTCTTAATCTTTTGGGTAAATATTTGCGGAGGAGGGATATGGAAT
ACTGGATGGATATGCTGCCAAGGCTTGAGAATAGTCTACGTATAGACGGTAAAATTGAAA
AAATACTAAGAATCAGCTATGATGGGTTAGAGAGTGAAGATCAAGAGATATTTCGTCATA
TCGCATGTCTTTTCAATCATATGGAAGTCACAACCATCAAGTCCTTGCTGGCAGATAGTG
ATGTTAGTTTTGCACTAGAAAACCTAGCTGATAAGTCCCTTATTCATGTCAGACAAGGTT
ATGTGGTGATGCACCGTTCGCTACAAGAAATGGGTAGAAAAATTGTTCGCATTCAGTCCA
TTGACAAACCTGGAGAACGAGAATTTCTGGTGGATCCAAATGATATACATGATATACTCA
ATGCATGCACTgtaagttttaaaaaaatattttttgatcctttcataactcaatatacgta
taaggtttaagagatgccatctgataaacaatgaattgtatgggggttgtctatttctcat
atatatcatatttttcagGGTACTCAAAAGGTTTTAGGTATATCACTGGATATAAGGAAT
ATTCGTGAGTTGGATGTACATGAGAGGGCCTTCAAAGGGATGTCTAATCTCCGTTTCTTA
GAAATTAAGAACTTTGGTTTGAAAGAAGACGGTTTGCATTTACCTCCAAGTTTCGACTAT
TTGCCCCGTACACTCAAACTATTGTGCTGGCCCAAATTTCCAATGAGGTGTATGCCTTTT
GGTTTTCGTCCTGAAAACCTTGTCAAGCTCGAAATGCAGTGCAGCAAGCTACATAAGCTA
TGGGAAGGAGTTGTGgtaagttttgagaataatttcttatgttgttatttttttttttt
tatgataatagtgccacgtgatgtgtaatttctgttgagctctatgtttgattttgttg
gatacagCCACTTGCATGTCTAAAGGAAATGGATCTGCGCGTATCATTAAAGCTGAAAGT
AATTCCAGATCTTTCTGAAGCTACTAATCTCGAGATACTTAATCTTTCGTTTTGCGAGAG
TTTGGTCGAGCTCCCATCCTCTATACGAAATCTCAATAAACTGTTGAACTTGGACATGTT
CTACTGCAAAAGTCTGAAAATTCTTCCTACCGGATTCAACCTCAAATCTCTTGACCGCCT
CCATCTCGATCATTGCTCAAAGTTGAAGACTTTTCCCAAATTCTCAACCAACATCTCAGT
TCTCAGTCTAAATCTAACAAACATTGAAGATTTCCCTTCTAATTTACATCTCCAGAATCT
TGTTGAGTTTAGCATATCAAAAGACGAGAGTGATGAGAAACAATGGGAAGAAGAGAAGgt
aagtagttctaaacttaacattatctccaaactcttttcctaacacttttataaaagaaa
agaaaaatcattgtcgttgactcaaactttgtacacttgtatgtgaaaacttaaaaaaca
ctaattttttatttatttatgaatattttaatttgattggaaagtaaattttggttacaaa
gaatgaagaagaaaatatctgattttaaaaataaataaataaaaagtaaaaaacagataa
aaatggaaagaaaataagaaattaaagatgatatcaattgggttttttcctttgtcgtga
tatcattaaaacgtaaaagaaaattatacatgggattttcttaatttattattttttagct
atttctaatgacatatattatgtaattaaaaaataacggttttaataaagagtagatgt
gagcgtgaatggaaagttccaaacaattatattaatgctgatgagatttacccataatac
attagtactgttattcttttcgttttaaagatttattttctaaaatttaactttaaaag
taatttgccactgaaaacccgtaaaacttgttatttggttcagCCGCTTACGCCCTTCCT
GGCGATGATGTTGTCTCCCACTTTGACGATCTTGCATCTCTGTGATATGCCAAGTTTGGT
GGAGCTTCCTTCCTCATTTCAGAATCTCAATCAACTGAAGGAGTTGATCATAATAAACTG
```

-continued

CATAAATCTGGAGACTCTGCCCACCGGAATCAACCTCCAATCTCTCTATTACCTTAGTTT
CAGAGGATGCTCACAGTTGAGGAGCTTTCCTGAAATCTCAACCAACATCTCAGTGCTCTA
TCTAGACGAAACAGCGATTGAAGAGGTTCCTTGGTGGATCGAGAAATTCTCTAACCTCAC
TGAGCTAAGAATGGACAGGTGCAGCAGGCTAAATGTGTGTTCCTACACATTTCTAAACT
GAAACATCTTCAGGAAGCTTTGTTTCGAAATTGTGGTACATTGACCAGAGTTGAATTGAG
TGGATATCCAAGTGGGATGGAGGTGATGAAAGCAGACAATATTGACACAGCCTCCTCTTC
TCTTCCTAAAGTCGTACTCAGTTTCTTGGACTGCTTCAACTTGGATCCAGAAACTGTCCT
TCATCACCAAGAATCAATTATTTTCAACTACATGTTATTTACAGGGAAAGGAGAAGTGCC
ATCATATTTCACTTACCGTACTACTGGAAGCTCCTCTCTGACCATTCCTCTACTTCACGT
CCATCTCTCCCAACCATTCTTCAGATTTAGGATTGGCGCATTGGTAACTATAGTTAATAC
GGAGGAGCCAGTAGAGCTCGAGGTAAAATGTGAGTTCAAAGACAGATTTGGGAACAACTT
TGATTATGACATTTATTTCGAAGTTTATAATCAAAACTATTGTGTGGAGGATGACTATAT
TATAGCTATATTGGACTGTCGTATCCCTCTAAACGAAGATAATGCTGCTCTAGCTCAACC
GAACTACTACGATCATGTGGATATAAAGATTGAGCAATTAGAGGAAGAGGAAAGATATGG
TGATATTGAACAATGGGGTATACGACTCTTAGAGGACTGTTCATCAGCGGAGACTCGACT
TGATAATTCAAACAGTACTCTTCCACATGTTTCTGAAGCCGAAGAAGGCAATATAGGGTA
TACACCTCTTCAAGGACTTGTTAATGAGATTGAACACAGTGAAGAGCCTGGAGATATCAA
TGTAGAAACTGAGAGAAGCACGAAGCGCATGCGGgtaagcattaagcaataattgaacat
aatgactattcatctctcaattcttttttgcattattgacaactagattcttttgcagCTA
TATCACTTCATA*TAA*GTAATATTAGGGTGTCTACGTCCAAACTAAACGGATGGGGTATAC
GACACTTAGAGGACTGTCATCAGCGAAGAACCGACATGGTAATCCAAACACTATGCAGCA
TGTTTGTGAAGCTGATGAAGGCAATGATGGATGCCATTAGACTGATCAGAACGAAGAGCG
AGGAGACAGTGATGAATAGTGATATAGGTAGGGAGAGTGATCACTTTGAAGAGTGCGAAT
ATAGTGATATAAGCAATGAGAGTGATTAGAGTGAAGAGCATGGGGATAGTGACGATGATG
GTATAAGCAATGAGACTAATCTGTTGGAAGAGTGTGGAAACAGTGATTAGGCAATGAGCT
TGATCAGAATGAAGACAGTTGAGATAGAGAGAACCAATACACAATACAAGgtaagtatta
atcaagaactgaacagaatatcagatatctcacagtcaggatctttaatagtatagatca
ctgagttgttttcttttacttgcagATTACGTGAAAAAGAAATGAATCTTTGAGATACTT
TTATGGTGATGGAATGAGTAGTTTTGCTGTCGGTTCTATGGAACAACAAGGAGAGCCCAA
GATTCTTCATTGTCTTCAGGGCAGATGAAGATGTTGCTGTTCATGTGAATGTTTTAAAAT
GTTTTGTTTCTTTTCTTAGGTTGCACGTTTGTGATAAGCTTATTTCATTACTATAACGAT
TCCTTTAATTTGCTGTCTAGCACAAAGTTTTACAGTGAACCCGAATTGAGTTTGTGATTT
ATAATAGTTCTCTTTTTTTATGAATAGTTgaaaagtgttatgtatagcatacacctatta
tggagagaaatcgaacgactgacttactttgtagccacacctgcaaagttttaggcatc
tttcaaagtccataaaccaacttagtctatttccgaattaactatataacacaaattgtt
tcaaatgcaagtcgtgttgtggatacaaaaaaactgatggaattcacggaaactggtata
agattaaaaggatttggtataagattctctgaagatggtaatgtagagagataattagtt
ggtccaaaaaatattttttgcttgcggccaccaaatccctagggacggctctggctatatg
gctttgtagctactccagctacgtaagaaatgagatcggataacttcattaacagaggtt
ttgtagaagaaaatatatctatataacaaaat The cDNA sequence (uppercase letters above) was experimentally determined, but the boundaries do not necessarily indicate transcription start and polyadenylation sites. Underlined lowercase letters are introns. The translational start and stop codons are in bold italics in the sequence above.

A coding sequence (CDS) for the Pla-1 homolog of AT1G31540.2 was determined by RT-PCR cDNA cloning and sequencing. The sequence of the identified open reading frame (ORF) is:

(SEQ ID NO: 1)
```
ATGGCTTCTTCATCTTCTTCTCACAATTGGTTATATGATGTTTCTTGAGCTTCAGAGGG
GAAGACGTCCGCGTAACATTCCGTAGCCACTTTCTCAAAGAGCTTGATCGGAAACTAATC
ACTGCTTTCAGAGACAATGAGATCGAGAGAAGCCACTCTCTCTGGCCCGATCTTGAACAA
GCCATCAAGGAATCCAGGATCGCTGTGGTCGTTTTCTCCATAAACTACGCTTCATCGAGC
TGGTGTCTTAACGAGTTGCTGGAGATTGTAAACTGCAATGATAAAATTGTCATACCAGTT
TTCTACCATGTGGATCCTTCACAAGTGAGGCATCAAATCGGCGACTTCGGAAAGATCTTT
GAAAATACTTGCAAGAGACAAACAGATGAGGAAGTGAAAAATCAATGGAAGAAAGCGCTG
ACTCTTGTAGCGAATATGCTTGGATTTGACTCTGCCAAATGGAACGACGAAGCAAAAATG
ATTGAAGAAATAGCCAATGATGTTTTGGGTAAACTGCTTTTAACTACACCTAAGGATTCT
GAGGAACTTGTTGGCATCGAAGATCACATCGCTGAAATGAGTTTACTGCTGCAACTGGAA
TCTGAAGAAGTGAGAATGGTTGGTATATCGGGTTCCTCAGGGATTGGTAAGACTACCATT
GCAAGAGCTCTGTTTAAACGACTTTCTCGACATTTCCAAGGTAGCACTTTCATCGACAGG
GCTTTTGTATCTTATAGTCGGAATATTTATAGTGGCGCCAATCCGGACGACCCCAATATG
AAGTTGCAGCTACAAGGACACTTCCTATCTGAAATTCTCGGCAAAAAGGACATAAAGATA
GATGATCCAGCTGCACTGGAAGAGAGGCTAAAGCACCAAAAAGTTCTTATCATTATTGAT
GATTTGGATGATATAATGGTACTAGATACATTAGTGGGTCAAACTCAATGGTTTGGATAT
GGGAGCAGAATCATTGTGGTTACAAATGATAAGCACTTCTTGATTGCTCATGGAATTGAT
CATATTTATGAAGTAAGTTTCCCAACTGATGTGCATGCTTGTCAGATGTTATGTCAATCT
GCATTCAAGCAAAACTATGCTCCTAAAGGTTTTGAGGATCTTGTAGTTGATGTAGTAAGA
CATGCGGGCAATTTTCCTTTGGGTCTTAATCTTTTGGGTAAATATTTGCGGAGGAGGGAT
ATGGAATACTGGATGGATATGCTGCCAAGGCTTGAGAATAGTCTACGTATAGACGGTAAA
ATTGAAAAAATACTAAGAATCAGCTATGATGGGTTAGAGAGTGAAGATCAAGAGATATTT
CGTCATATCGCATGTCTTTTCAATCATATGGAAGTCACAACCATCAAGTCCTTGCTGGCA
GATAGTGATGTTAGTTTTGCACTAGAAAACCTAGCTGATAAGTCCCTTATTCATGTCAGA
CAAGGTTATGTGGTGATGCACCGTTCGCTACAAGAAATGGGTAGAAAAATTGTTCGCATT
CAGTCCATTGACAAACCTGGAGAACGAGAATTTCTGGTGGATCCAAATGATATACATGAT
ATACTCAATGCATGCACTGGTACTCAAAAGGTTTTAGGTATATCACTGGATATAAGGAAT
ATTCGTGAGTTGGATGTACATGAGAGGGCCTTCAAAGGGATGTCTAATCTCCGTTTCTTA
GAAATTAAGAACTTTGGTTTGAAAGAAGACGGTTTGCATTTACCTCCAAGTTTCGACTAT
TTGCCCCGTACACTCAAACTATTGTGCTGGCCCAAATTTCCAATGAGGTGTATGCCTTTT
GGTTTTCGTCCTGAAAACCTTGTCAAGCTCGAAATGCAGTGCAGCAAGCTACATAAGCTA
TGGGAAGGAGTTGTGCCACTTGCATGTCTAAAGGAAATGGATCTGCGCGTATCATTAAAG
CTGAAAGTAATTCCAGATCTTTCTGAAGCTACTAATCTCGAGATACTTAATCTTTCGTTT
TGCGAGAGTTTGGTCGAGCTCCCATCCTCTATACGAAATCTCAATAAACTGTTGAACTTG
GACATGTTCTACTGCAAAAGTCTGAAAATTCTTCCTACCGGATTCAACCTCAAATCTCTT
GACCGCCTCCATCTCGATCATTGCTCAAAGTTGAAGACTTTTCCCAAATTCTCAACCAAC
ATCTCAGTTCTCAGTCTAAATCTAACAAACATTGAAGATTTCCCTTCTAATTTACATCTC
```

```
CAGAATCTTGTTGAGTTTAGCATATCAAAAGACGAGAGTGATGAGAAACAATGGGAAGAA

GAGAAGCCGCTTACGCCCTTCCTGGCGATGATGTTGTCTCCCACTTTGACGATCTTGCAT

CTCTGTGATATGCCAAGTTTGGTGGAGCTTCCTTCCTCATTTCAGAATCTCAATCAACTG

AAGGAGTTGATCATAATAAACTGCATAAATCTGGAGACTCTGCCCACCGGAATCAACCTC

CAATCTCTCTATTACCTTAGTTTCAGAGGATGCTCACAGTTGAGGAGCTTTCCTGAAATC

TCAACCAACATCTCAGTGCTCTATCTAGACGAAACAGCGATTGAAGAGGTTCCTTGGTGG

ATCGAGAAATTCTCTAACCTCACTGAGCTAAGAATGGACAGGTGCAGCAGGCTAAAATGT

GTGTTCCTACACATTTCTAAACTGAAACATCTTCAGGAAGCTTTGTTTCGAAATTGTGGT

ACATTGACCAGAGTTGAATTGAGTGGATATCCAAGTGGGATGGAGGTGATGAAAGCAGAC

AATATTGACACAGCCTCCTCTTCTCTTCCTAAAGTCGTACTCAGTTTCTTGGACTGCTTC

AACTTGGATCCAGAAACTGTCCTTCATCACCAAGAATCAATTATTTTCAACTACATGTTA

TTTACAGGGAAAGGAGAAGTGCCATCATATTTCACTTACCGTACTACTGGAAGCTCCTCT

CTGACCATTCCTCTACTTCACGTCCATCTCTCCCAACCATTCTTCAGATTTAGGATTGGC

GCATTGGTAACTATAGTTAATACGGAGGAGCCAGTAGAGCTCGAGGTAAAATGTGAGTTC

AAAGACAGATTTGGGAACAACTTTGATTATGACATTTATTTCGAAGTTTATAATCAAAAC

TATTGTGTGGAGGATGACTATATTATAGCTATATTGGACTGTCGTATCCCTCTAAACGAA

GATAATGCTGCTCTAGCTCAACCGAACTACTACGATCATGTGGATATAAAGATTGAGCAA

TTAGAGGAAGAGGAAAGATATGGTGATATTGAACAATGGGGTATACGACTCTTAGAGGAC

TGTTCATCAGCGGAGACTCGACTTGATAATTCAAACAGTACTCTTCCACATGTTTCTGAA

GCCGAAGAAGGCAATATAGGGTATACACCTCTTCAAGGACTTGTTAATGAGATTGAACAC

AGTGAAGAGCCTGGAGATATCAATGTAGAAACTGAGAGAAGCACGAAGCGCATGCGGCTA

TATCACTTCATATAA ,
``` which encodes the following Pla-1 homolog of AT1G31540.2 amino acid sequence (1164 aa, pI=5.27, MM=133804.52 daltons).

```
                                            (SEQ ID NO: 2)
MASSSSSHNWLYDVFLSFRGEDVRVTFRSHFLKELDRKLITAFRDNEIER

SHSLWPDLEQAIKESRIAVVVFSINYASSSWCLNELLEIVNCNDKIVIPV

FYHVDPSQVRHQIGDFGKIFENTCKRQTDEEVKNQWKKALTLVANMLGED

SAKWNDEAKMIEEIANDVLGKLLLTTPKDSEELVGIEDHIAEMSLLLQLE

SEEVRMVGISGSSGIGKITIARALFKRLSRHFQGSTFIDRAFVSYSRNIY

SGANPDDPNMKLQLQGHFLSEILGKKDIKIDDPAALEERLKHQKVLIIID

DLDDIMVLDTLVGQTQWFGYGSRIIVVINDKHFLIAHGIDHIYEVSFPTD

VHACQMLCQSAFKQNYAPKGFEDLVVDVVRHAGNFPLGLNLLGKYLRRRD

MEYWMDMLPRLENSLRIDGKIEKILRISYDGLESEDQEIFRHIACLFNHM

EVTTIKSLLADSDVSFALENLADKSLIHVRQGYVVMHRSLQEMGRKIVRI

QSIDKPGEREFLVDPNDIHDILNACTGTQKVLGISLDIRNIRELDVHERA

FKGMSNLRFLEIKNFGLKEDGLHLPPSFDYLPRTLKLLCWPKFPMRCMPF

GFRPENLVKLEMQCSKLHKLWEGVVPLACLKEMDLRVSLKLKVIPDLSEA

TNLEILNLSFCESLVELPSSIRNLNKLLNLDMFYCKSLKILPTGFNLKSL

DRLHLDHCSKLKTFPKFSTNISVLSLNLTNIEDFPSNLHLQNLVEFSISK

DESDEKQWEEEKPLTPFLAMMLSPTLTILHLCDMPSLVELPSSFQNLNQL

KELIIINCINLETLPTGINLQSLYYLSFRGCSQLRSFPEISTNISVLYLD

ETAIEEVPWWIEKFSNLTELRMDRCSRLKCVFLHISKLKHLQEALFRNCG

TLTRVELSGYPSGMEVMKADNIDTASSSLPKVVLSFLDCFNLDPETVLHH

QESIIFNYMLFTGKGEVPSYFTYRTTGSSSLTIPLLHVHLSQPFFRFRIG

ALVTIVNTEEPVELEVKCEFKDRFGNNFDYDIYFEVYNQNYCVEDDYIIA

ILDCRIPLNEDNAALAQPNYYDHVDIKIEQLEEEERYGDIEQWGIRLLED

CSSAETRLDNSNSTLPHVSEAEEGNIGYTPLQGLVNEIEHSEEPGDINVE

TERSTKRMRLYHFI
```

A second isoform has also been identified that lacks amino acids the C-terminal 253 amino acids of SEQ ID NO: 2 (i.e., the UID) and has a unique C-terminal 14 amino acids, with the following open reading frame sequence:

```
                                            (SEQ ID NO: 3)
ATGGCTTCTTCATCTTCTTCTCACAATTGGTTATATGATGTTTTCTTGAG

CTTCAGAGGGGAAGACGTCCGCGTAACATTCCGTAGCCACTTTCTCAAAG

AGCTTGATCGGAAACTAATCACTGCTTTCAGAGACAATGAGATCGAGAGA
```

-continued

```
AGCCACTCTCTCTGGCCCGATCTTGAACAAGCCATCAAGGAATCCAGGAT
CGCTGTGGTCGTTTTCTCCATAAACTACGCTTCATCGAGCTGGTGTCTTA
ACGAGTTGCTGGAGATTGTAAACTGCAATGATAAAATTGTCATACCAGTT
TTCTACCATGTGGATCCTTCACAAGTGAGGCATCAAATCGGCGACTTCGG
AAAGATCTTTGAAAATACTTGCAAGAGACAAACAGATGAGGAAGTGAAAA
ATCAATGGAAGAAAGCGCTGACTCTTGTAGCGAATATGCTTGGATTTGAC
TCTGCCAAATGGAACGACGAAGCAAAAATGATTGAAGAAATAGCCAATGA
TGTTTTGGGTAAACTGCTTTTAACTACACCTAAGGATTCTGAGGAACTTG
TTGGCATCGAAGATCACATCGCTGAAATGAGTTTACTGCTGCAACTGGAA
TCTGAAGAAGTGAGAATGGTTGGTATATCGGGTTCCTCAGGGATTGGTAA
GACTACCATTGCAAGAGCTCTGTTTAAACGACTTTCTCGACATTTCCAAG
GTAGCACTTTCATCGACAGGGCTTTTGTATCTTATAGTCGGAATATTTAT
AGTGGCGCCAATCCGGACGACCCCAATATGAAGTTGCAGCTACAAGGACA
CTTCCTATCTGAAATTCTCGGCAAAAAGGACATAAAGATAGATGATCCAG
CTGCACTGGAAGAGAGGCTAAAGCACCAAAAAGTTCTTATCATTATTGAT
GATTTGGATGATATAATGGTACTAGATACATTAGTGGGTCAAACTCAATG
GTTTGGATATGGGAGCAGAATCATTGTGGTTACAAATGATAAGCACTTCT
TGATTGCTCATGGAATTGATCATATTTATGAAGTAAGTTTCCCAACTGAT
GTGCATGCTTGTCAGATGTTATGTCAATCTGCATTCAAGCAAAACTATGC
TCCTAAAGGTTTTGAGGATCTTGTAGTTGATGTAGTAAGACATGCGGGCA
ATTTTCCTTTGGGTCTTAATCTTTTGGGTAAATATTTGCGGAGGAGGGAT
ATGGAATACTGGATGGATATGCTGCCAAGGCTTGAGAATAGTCTACGTAT
AGACGGTAAAATTGAAAAAATACTAAGAATCAGCTATGATGGGTTAGAGA
GTGAAGATCAAGAGATATTTCGTCATATCGCATGTCTTTTCAATCATATG
GAAGTCACAACCATCAAGTCCTTGCTGGCAGATAGTGATGTTAGTTTTGC
ACTAGAAAACCTAGCTGATAAGTCCCTTATTCATGTCAGACAAGGTTATG
TGGTGATGCACCGTTCGCTACAAGAAATGGGTAGAAAAATTGTTCGCATT
CAGTCCATTGACAAACCTGGAGAACGAGAATTTCTGGTGGATCCAAATGA
TATACATGATATACTCAATGCATGCACTGGTACTCAAAAGGTTTTAGGTA
TATCACTGGATATAAGGAATATTCGTGAGTTGGATGTACATGAGAGGGCC
TTCAAAGGGATGTCTAATCTCCGTTTCTTAGAAATTAAGAACTTTGGTTT
GAAAGAAGACGGTTTGCATTTACCTCCAAGTTTCGACTATTTGCCCCGTA
CACTCAAACTATTGTGCTGGCCCAAATTTCCAATGAGGTGTATGCCTTTT
GGTTTTCGTCCTGAAAACCTTGTCAAGCTCGAAATGCAGTGCAGCAAGCT
ACATAAGCTATGGGAAGGAGTTGTGCCACTTGCATGTCTAAAGGAAATGG
ATCTGCGCGTATCATTAAAGCTGAAAGTAATTCCAGATCTTTCTGAAGCT
ACTAATCTCGAGATACTTAATCTTTCGTTTTGCGAGAGTTTGGTCGAGCT
CCCATCCTCTATACGAAATCTCAATAAACTGTTGAACTTGGACATGTTCT
ACTGCAAAAGTCTGAAAATTCTTCCTACCGGATTCAACCTCAAATCTCTT
GACCGCCTCCATCTCGATCATTGCTCAAAGTTGAAGACTTTTCCCAAATT
CTCAACCAACATCTCAGTTCTCAGTCTAAATCTAACAAACATTGAAGATT
TCCCTTCTAATTTACATCTCCAGAATCTTGTTGAGTTTAGCATATCAAAA
GACGAGAGTGATGAGAAACAATGGGAAGAAGAGAAGGTAAGTAGTTCTAA
ACTTAACATTATCTCCAAACTCTTTTCCTAA,
``` which encodes the following amino acid sequence:

(SEQ ID NO: 4)
MASSSSSHNWLYDVFLSFRGEDVRVTFRSHFLKELDRKLITAFRDNEIER
SHSLWPDLEQAIKESRIAVVVFSINYASSSWCLNELLEIVNCNDKIVIPV
FYHVDPSQVRHQIGDFGKIFENTCKRQTDEEVKNOWKKALTLVANMLGFD
SAKWNDEAKMIEEIANDVLGKLLLTTPKDSEELVGIEDHIAEMSLLLQLE
SEEVRMVGISGSSGIGKTTIARALFKRLSRHFQGSTFIDRAFVSYSRNIY
SGANPDDPNMKLQLQGHFLSEILGKKDIKIDDPAALEERLKHQKVLIIID
DLDDIMVLDTLVGQTQWFGYGSRIIVVTNDKHFLIAHGIDHIYEVSFPTD
VHACQMLCQSAFKQNYAPKGFEDLVVDVVRHAGNFPLGLNLLGKYLRRRD
MEYWMDMLPRLENSLRIDGKIEKILRISYDGLESEDQEIFRHIACLFNHM
EVTTIKSLLADSDVSFALENLADKSLIHVRQGYVVMHRSLQEMGRKIVRI
QSIDKPGEREFLVDPNDIHDILNACTGTQKVLGISLDIRNIRELDVHERA
FKGMSNLRFLEIKNFGLKEDGLHLPPSFDYLPRTLKLLCWPKFPMRCMPF
GFRPENLVKLEMQCSKLHKLWEGVVPLACLKEMDLRVSLKLKVIPDLSEA
TNLEILNLSFCESLVELPSSIRNLNKLLNLDMFYCKSLKILPTGFNLKSL
DRLHLDHCSKLKTFPKFSTNISVLSLNLTNIEDFPSNLHLQNLVEFSISK
DESDEKQWEEEKVSSSKLNIISKLFS.

Amino acids 1-762 of SEQ ID NOs: 2 and 4 are identical, whereas amino acids 763-776 of SEQ ID NO: 4 (underlined above) are unique to the shorter isoform.

The presently disclosed subject matter encompasses the identification and isolation of cDNAs encoding genes of interest in the expression of geminivirus resistance. Altering the expression of genes related to these traits can be used to improve or modify the crop plants, grain, or fruit, or both plants and grain or fruit, as desired. Examples describe the isolated genes of interest and methods for analyzing the alteration of expression and their effects on the plant characteristics.

IIIA.1. Nucleic Acid Molecules

In some embodiments, the presently disclosed subject matter relates to nucleic acids, optionally isolated nucleic acids. In some embodiments, an isolated nucleic acid molecule of the presently disclosed subject matter comprises, consists essentially of, or consists of a nucleotide sequence, its full complement, or its full reverse complement, the nucleotide sequence encoding a polypeptide selected from the group consisting of (a) a polypeptide comprising, consisting essentially of, or consisting of an amino acid sequence listed in SEQ ID NOs: 2, 4, or 18, or a functional fragment, domain, repeat, or feature thereof; (b) a polypeptide comprising, consisting essentially of, or consisting of an amino acid sequence that is at least 90% identical to and having a same function as a polypeptide comprising, consisting essentially of, or consisting of an amino acid sequence of one of SEQ ID NOs: 2, 4, and/or 18; (c) a polypeptide comprising, consisting essentially of, or consisting of an amino acid sequence encoded by a nucleotide sequence having at least 90% identity to a nucleotide sequence listed in SEQ ID NOs: 1, 3, or 17, or a functional fragment, domain, or feature thereof, or a sequence fully complementary thereto; and (d) a polypeptide comprising, consisting essentially of, or consisting of an amino acid sequence encoded by a nucleotide sequence capable of hybridizing under high stringency conditions to a nucleotide sequence listed in one of SEQ ID NOs: 1, 3, and/or 17, or to a sequence fully complementary thereto. In some embodiments, an isolated nucleic acid molecule of the presently disclosed subject matter comprises, consists essentially of, or consists of a nucleotide sequence, the nucleotide sequence selected from the group consisting of (a) a nucleotide sequence listed in SEQ ID NOs: 1, 3, or 17; (b) a nucleotide sequence that is at least 90% identical to (a); (c) a nucleotide sequence capable of hybridizing to (a) under high stringency conditions; (d) a nucleotide sequence complementary to (a), (b) or (c); and (e) a nucleotide sequence which is the reverse complement of (a), (b) or (c).

In some embodiments, a nucleic acid molecule of the presently disclosed subject matter functions in geminivirus resistance, optionally by providing partial or complete resistance to a geminivirus. In some embodiments, the geminivirus is selected from the group consisting of a begomovirus, a mastrevirus, a curtovirus, or any other geminivirus. In some embodiments, the partial or complete resistance is characterized by a reduction in or an elimination of leaf chlorosis and/or leaf curling in a plant that comprises the nucleic acid molecule and/or the functional fragment of the presently disclosed subject matter as compared to the degree of leaf chlorosis and/or leaf curling that the same plant under the same circumstances would have had had it not comprised the nucleic acid and/or the functional fragment of the presently disclosed subject matter.

Embodiments of the presently disclosed subject matter thus encompass isolated nucleic acid molecules corresponding to genes that function in geminivirus resistance, optionally by providing partial or complete resistance to a geminivirus. In some embodiments, an isolated nucleic acid molecule of the presently disclosed subject matter comprises a nucleotide sequence set forth in SEQ ID NOs: 1, 3, and/or 17, or a functional fragment, domain, or feature thereof. In some embodiments, an isolated nucleic acid molecule of the presently disclosed subject matter comprises a nucleotide sequence having substantial identity to a nucleotide sequence set forth in SEQ ID NOs: 1, 3, and/or 17, or a functional fragment, domain, or feature thereof. Another embodiment of the presently disclosed subject matter encompasses an isolated nucleic acid molecule comprising a nucleotide sequence that is complementary to, or the reverse complement of, a nucleotide sequence listed in SEQ ID NOs: 1, 3, and/or 17, or a functional fragment, domain, or feature thereof. Some embodiments of the presently disclosed subject matter encompass an isolated nucleic acid molecule comprising a nucleotide sequence that is complementary to, or the reverse complement of, a nucleotide sequence that has substantial identity to, or is capable of hybridizing to, a nucleotide sequence listed in SEQ ID NOs: 1, 3, and/or 17, or a functional fragment, domain, or feature thereof.

In some embodiments, the substantial identity is at least about 60% identity, in some embodiments at least about 65% identity, in some embodiments at least about 70% identity, in some embodiments at least about 75% identity, in some embodiments at least about 80% identity, in some embodiments at least about 85% identity, in some embodiments at least about 90% identity, in some embodiments at least about 91% identity, in some embodiments at least about 92% identity, in some embodiments at least about 93% identity, in some embodiments at least about 94% identity, in some embodiments at least about 95% identity, in some embodiments at least about 96% acid identity, in some embodiments at least about 97% identity, in some embodiments at least about 98% identity, in some embodiments at least about 99% identity, and in some embodiments about 100% identity to the nucleotide sequences listed in SEQ ID NOs: 1, 3, and/or 17, or a functional fragment, domain, or feature thereof.

In some embodiments, the nucleotide sequence having substantial identity comprises an allelic variant of the nucleotide sequences listed in SEQ ID NOs: 1, 3, and/or 17, or a functional fragment, domain, or feature thereof. In some embodiments, the nucleotide sequence having substantial identity comprises a naturally occurring variant. In some embodiments, the nucleotide sequence having substantial identity comprises a polymorphic variant of the nucleotide sequences listed in SEQ ID NOs: 1, 3, and/or 17, or a functional fragment, domain, or feature thereof.

In some embodiments, the nucleic acid having substantial identity comprises a deletion or insertion of at least one nucleotide. In some embodiments, the deletion or insertion comprises less than about thirty nucleotides. In some embodiments, the deletion or insertion comprises less than about five nucleotides. In some embodiments, the sequence of the isolated nucleic acid having substantial identity comprises a substitution in at least one codon. In some embodiments, the substitution is conservative (i.e., encodes a conservative amino acid substitution as compared to the reference sequence).

In some embodiments, the isolated nucleic acid comprises a nucleotide sequence capable of hybridizing to a nucleotide sequence listed in SEQ ID NOs: 1, 3, and/or 17, or a functional fragment, domain, or feature thereof. In some embodiments, hybridization allows the sequence to form a duplex at medium or high stringency.

In some embodiments, the isolated nucleic acid comprises a plurality of regions having a nucleotide sequence listed in SEQ ID NOs: 1, 3, and/or 17, or an exon, domain, or feature thereof.

In some embodiments, the sequence having substantial identity to the nucleotide sequences listed in SEQ ID NOs: 1, 3, and/or 17, or a functional fragment, domain, or feature thereof, is from a plant. In some embodiments, the plant is a dicot. In some embodiments, the plant is a gymnosperm. In some embodiments, the plant is a monocot. In some embodiments, the monocot is a cereal. In some embodiments, the cereal can be, for example, maize, wheat, barley, oats, rye, millet, sorghum, triticale, *secale*, einkorn, spelt, emmer, teff, milo, flax, gramma grass, *Tripsacum* sp., or teosinte. In some embodiments, the plant is a dicot. In some embodiments, the dicot is selected from the group consisting of tomato, cassava, and cotton, In some embodiments, the plant is selected from the group consisting of *Arabidopsis*, rice, wheat, barley, rye, corn, potato, canola, soybean, sunflower, carrot, sweet potato, sugarbeet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, *papaya*, mango, banana, soybean, tobacco, tomato, sorghum, sugarcane, and cassava.

In some embodiments, the nucleic acid is expressed in a specific location or tissue of a plant. In some embodiments, the location or tissue includes, but is not limited to, epidermis, root, vascular tissue, meristem, cambium, cortex, pith, leaf, flower, and combinations thereof. In some embodiments, the location or tissue is a leaf. In some embodiments, the location or tissue is a seed.

In some embodiments, the nucleic acid encodes a polypeptide involved in a function including, but not limited to, carbon metabolism, photosynthesis, signal transduction, cell growth, reproduction, disease processes, gene regulation, and differentiation. In some embodiments, the nucleic acid encodes a polypeptide involved in geminivirus-caused disease resistance, enhanced yield, or nutritional content.

As used herein, the phrase "involved in" in reference to a gene or gene product is means that the gene or gene product functions in a particular biochemical pathway or reaction. By way of example, the gene or protein glucose-6-phosphate dehydrogenase is involved in (i.e. functions) in glucose metabolism.

Embodiments of the presently disclosed subject matter further relate to an isolated polynucleotide comprising a nucleotide sequence of at least 10 bases, which sequence is identical, complementary (for example, fully complementary), or substantially identical to a region of any sequence of SEQ ID NOs: 1, 3, and/or 17, and wherein the polynucleotide is adapted for any of numerous uses.

In some embodiments, the polynucleotide is used as a chromosomal marker. In some embodiments, the polynucleotide is used as a marker for restriction fragment length polymorphism (RFLP) analysis. In some embodiments, the polynucleotide is used as a marker for quantitative trait-linked analysis and/or breeding. In some embodiments, the polynucleotide is used as a marker for marker-assisted breeding. In some embodiments, the polynucleotide is used as a bait sequence in a two-hybrid system to identify sequence-encoding polypeptides interacting with the polypeptide encoded by the bait sequence. In some embodiments, the polynucleotide is used as a diagnostic indicator for genotyping or identifying an individual or population of individuals. In some embodiments, the polynucleotide is used for genetic analysis to identify boundaries of genes or exons.

Embodiments of the presently disclosed subject matter also relate to a shuffled nucleic acid molecule comprising a plurality of nucleotide sequence fragments, wherein at least one of the fragments corresponds to a region of a nucleotide sequence listed in SEQ ID NOs: 1, 3, and/or 17, and wherein at least two of the plurality of sequence fragments are in an order, from 5' to 3', which is not an order in which the plurality of fragments naturally occur. In some embodiments, all of the fragments in a shuffled nucleic acid comprising a plurality of nucleotide sequence fragments are from a single gene. In some embodiments, the plurality of fragments is derived from at least two different genes. In some embodiments, the shuffled nucleic acid is operatively linked to a promoter sequence. In some embodiments, the shuffled nucleic acid comprises a chimeric polynucleotide comprising a promoter sequence operatively linked to the shuffled nucleic acid. In some embodiments, the shuffled nucleic acid is contained within a host cell.

III.A.2. Cassettes, Vectors, Cells, Transgenic Plants, and Progeny and Seed Derived Therefrom In some embodiments, the presently disclosed subject matter relates to nucleic acid cassettes comprising one or more of the nucleic acid molecules and fragments disclosed herein. In some embodiments, the nucleic acid cassette comprises, consists essentially of, or consists of a nucleic acid sequence as set forth in SEQ ID NO: 1, SEQ ID NO: 3, SEQ ID NO: 17, or a functional fragment thereof, or a sequence at least 90% identical thereto.

In some embodiments, the presently disclosed subject matter relates to expression cassettes, wherein the expression cassettes comprise a promoter operatively linked to a nucleic acid molecule of the presently disclosed subject matter such that when introduced into a plant or plant cell, the nucleic acid molecule is expressed in the plant or plant cell. In some embodiments, the presently disclosed subject matter thus relates to recombinant vectors that comprise the expression cassettes disclosed herein.

Similarly, in some embodiments the presently disclosed subject matter relates to cells that comprise the expression cassettes disclosed herein. As would be understood by one of ordinary skill in the art, the cells of the presently disclosed subject matter can be produced by transformation of plants and/or plant cells. Plant transformation with the nucleic acid molecules of the presently disclosed subject matter can in some embodiments involve the construction of such an expression vector that functions in plant cells and comprises a nucleic acid sequence of the presently disclosed subject matter that confers partial or complete resistance to a geminivirus. This nucleic acid sequence is in some embodiments controlled or operatively linked to one or more regulatory element, such as a promoter. The expression vector can contain one or more such operably linked gene/regulatory element combinations, provided that at least one of the genes contained in the combinations encodes a gene product that confers partial or complete resistance to a geminivirus. The vector(s) can be in the form of a plasmid, and can be used, alone or in combination with other plasmids, to provide transgenic plants that are resistant to geminivirus, using transformation methods known in the art, such as the *Agrobacterium* transformation system, biolistic transformation, etc. See e.g., U.S. Pat. Nos. 4,945,050; 5,932,782; and 5,981,184, each of which is incorporated herein by reference in its entirety. In some embodiments, a transformation method is chosen based on the appropriateness of that method for a particular plant species.

By way of example and not limitation, in some embodiments an expression cassette of the presently disclosed subject matter comprises, consists essentially of, or consists of a promoter operably linked to a coding sequence, which is also operably linked to a transcription terminator. In some embodiments, the expression cassette comprises, consists essentially of, or consists of a promoter having a nucleotide sequence selected from the group consisting of SEQ ID NO: 29 and SEQ ID NO: 30, a coding sequence comprising, consisting essentially of, or consisting of SEQ ID NO: 1, and a transcription terminator selected from the group consisting of SEQ ID NO: 33 and SEQ ID NO: 34. In particular non-limiting examples, an expression cassette of the presently disclosed subject matter comprises, consists essentially of, or consists of the following nucleotide sequences in 5' to 3' order:

(a) SEQ ID NO: 30, SEQ ID NO: 1, and SEQ ID NO: 34; or (b) SEQ ID NO: 29, SEQ ID NO: 1, and SEQ ID NO: 33; or (c) SEQ ID NO: 32, SEQ ID NO: 1, and SEQ ID NO: 34; or (d) SEQ ID NO: 29, SEQ ID NO: 1, and SEQ ID NO: 33.

In some embodiments, the expression cassette comprises, consists essentially of, or consists of a promoter, a polynucleotide nucleotide sequence (e.g., a coding sequence), a tag sequence, and a transcription terminator. In particular non-limiting examples, an expression cassette of the presently disclosed subject matter comprises, consists essentially of, or consists of the following nucleotide sequences in 5' to 3' order:

(a) SEQ ID NO: 30, SEQ ID NO: 1, SEQ ID NO: 35 or SEQ ID NO: 36, and SEQ ID NO: 34;
(b) SEQ ID NO: 29, SEQ ID NO: 1, SEQ ID NO: 35 or SEQ ID NO: 36, and SEQ ID NO: 33;
(c) SEQ ID NO: 32, SEQ ID NO: 1, SEQ ID NO: 35 or SEQ ID NO: 36, and SEQ ID NO: 34; and
(d) SEQ ID NO: 29, SEQ ID NO: 1, SEQ ID NO: 19, and SEQ ID NO: 33.

In some embodiments, the expression cassette includes at least two promoter/coding sequence/transcription terminator sequences, optionally with tag sequences between the coding sequence and the transcription terminator. In some embodiments, the tag sequences are the same in the first and second promoter/coding sequence/tag sequence/transcription terminator sequences, and in some embodiments the tag sequences are different in the first promoter/coding sequence/tag sequence/transcription terminator sequence and the second promoter/coding sequence/tag sequence/transcription terminator sequence. Thus, in some embodiments the expression cassette comprises, consists essentially of a first promoter, first polynucleotide nucleotide sequence, first tag sequence, and first transcription terminator and a second promoter, second polynucleotide nucleotide sequence, second tag sequence, and second transcription terminator. In some embodiments, the first promoter is the same as the second promoter and in some embodiments the first promoter is different from the second promoter. In some embodiments, the first coding sequence is the same as the second coding sequence and in some embodiments the first coding sequence is different from the second coding sequence. In some embodiments, the first tag sequence, if present, is the same as the second tag sequence, if present, and in some embodiments the first tag sequence, if present, is different from the second tag sequence, if present. In some embodiments, a first tag sequence is present and a second tag sequence is absent, and in some embodiments a first tag sequence is absent and a second tag sequence is present. In some embodiments, the first promoter, first polynucleotide nucleotide sequence, first tag sequence, and first transcription terminator in 5' to 3' orientation are SEQ ID NO: 29, SEQ ID NO: 1, SEQ ID NO: 19, and SEQ ID NO: 33, respectively, and the second promoter, second polynucleotide nucleotide sequence, second tag sequence, and second transcription terminator in 5' to 3' orientation are SEQ ID NO: 30, SEQ ID NO: 1, SEQ ID NO: 35 or SEQ ID NO: 36, and SEQ ID NO: 34, respectively.

In some embodiments, the presently disclosed subject matter also provides transgenic plants that comprise an expression cassette as described herein. In some embodiments, the transgenic plant is a dicot or a monocot. In some embodiments, the transgenic plant is selected from the group consisting of tomato, cassava, cotton, rice, wheat, barley, rye, corn, potato, canola, soybean, sunflower, carrot, sweet potato, sugarbeet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, *papaya*, mango, banana, soybean, tobacco, sorghum, and sugarcane. In some embodiments, the transgenic plant is tomato. In some embodiments, the transgenic plant is cassava. In some embodiments, the transgenic plant is cotton. In some embodiments, the expression cassette is expressed in a tissue selected from the group consisting of the epidermis, root, vascular tissue, meristem, cambium, cortex, pith, leaf, flower, and combinations thereof.

Thus, in some embodiments the transgenic plant of the presently disclosed subject matter has altered geminivirus resistance. In some embodiments, the geminivirus is selected from the group consisting of a begomovirus, a mastrevirus, a capulavirus, a citlodavirus, a eragrovirus, a grablovirus, a maldovirus, a mulcrilevirus, a opunvirus, a topilevirus, a topocuvirus, a turncurtovirus and a curtovirus.

Also provided are progeny and seed from a plant of the presently disclosed subject matter, wherein the progeny exhibits partial or complete resistance to a geminivirus and/or wherein the seed produces a plant that exhibits partial or complete resistance to a geminivirus.

In some embodiments, rather than transforming the plant or the plant cell with a nucleic acid sequence that confers partial or complete resistance to a geminivirus, an endogenous plant gene is edited to generate a modified endogenous nucleic acid that confers partial or complete resistance to a geminivirus. Methods for gene editing in plants are known. By way of example and not limitation, recombinant transcription factors comprising the DNA binding domains from zinc finger proteins ("ZFPs") or TAL-effector domains ("TALEs") and engineered nucleases including zinc finger nucleases ("ZFNs"), TALENs, CRISPR/Cas nuclease systems, and homing endonucleases that are all designed to specifically bind to target DNA sites have the ability to regulate gene expression of endogenous genes and are useful in genome engineering and gene therapy. See e.g., U.S. Pat. Nos. 9,045,763; 9,005,973; 8,956,828; 8,945,868; 8,586,526; 6,534,261; 6,599,692; 6,503,717; 6,689,558; 7,067,317; 7,262,054; 7,888,121; 7,972,854; 7,914,796; 7,951,925; 8,110,379; and 8,409,861; and U.S. Patent Publication Nos. 2003/0232410; 2005/0208489; 2005/0026157; 2005/0064474; 2006/0063231; 2008/0159996; 2010/0218264; 2011/0265198; 2012/0017290; 2013/0122591; 2013/0137104; 2013/0177960; 2013/0177983; and 2015/0056705, the disclosure of each of which is incorporated by reference in its entirety for all purposes.

Further, targeted nucleases are being developed based on the Argonaute system (e.g., from *T. thermophilus*, known as 'TtAgo' (see Swarts et al., 2014), which also may have the potential for uses in genome editing and gene therapy.

Thus, in some embodiments the presently disclosed subject matter relates to a method for altering geminivirus resistance of a plant by expressing in the plant an expression cassette comprising a nucleic acid molecule of the presently disclosed subject matter that encodes a polypeptide as disclosed herein that confers partial or complete resistance to a geminivirus.

Additionally, in some embodiments the presently disclosed subject matter relates to a method for increasing the expression of an isolated nucleic acid molecule of the presently disclosed subject matter in a plant, the method comprising (a) inserting into the plant an expression cassette comprising an isolated nucleic acid molecule of the presently disclosed subject matter that confers partial or complete resistance to a geminivirus; and (b) growing the plant comprising the expression cassette under suitable growth conditions, wherein the expression of the isolated nucleic acid molecule of the presently disclosed subject matter is increased to thereby confer partial or complete resistance to a geminivirus.

Nuclease-mediated gene therapy can be used to genetically engineer a cell to have one or more inactivated genes and/or to cause that cell to express a product not previously being produced in that cell (e.g., via transgene insertion and/or via correction of an endogenous sequence), thereby improving both the safety and efficiency with which plants and plant cells can be engineered. In particular, the use of engineered nucleases such as zinc finger nucleases (ZFNs), TALENs, TtAgo, and CRISPR/Cas9 systems provide the capability of precisely engineering specific genes. The nucleases act by creating double-stranded breaks (DSB) at a targeted DNA sequence, whose subsequent repair is then exploited to achieve one of three outcomes: gene knockout, gene mutation, or the site-specific addition (i.e., insertion or integration) of new genetic material (transgenes or fragments thereof) at the locus. For example, if DSB repair occurs through the error-prone NHEJ pathway, the result can be small insertions and/or deletions of nucleotides at the break site that thereby disrupt an open-reading frame. Methods for employing CRISPR/Cas9 systems to edit genes in plants include, but are not limited to those described in U.S. Pat. Nos. 10,662,437; 10,557,146; and 9,745,600; and in U.S. Patent Application Publication Nos. 2018/0073035, 2017/0166912, 2017/0114351, and 2015/0067922, the disclosure of each of which is incorporated by reference herein in its entirety. In some embodiments, a wild type plant gene (e.g., a wild-type AT1G31540 gene product) is modified by gene editing to produce in the plant a genetic locus that encodes a disease resistance protein (TIR-NBS-LRR class) family derivative that has a nucleic acid sequence that is identical to or at least 90%, 91%, 92%, 93%, 94%, 95%, 96%, 97%, 98%, or 99% identical to one of SEQ ID NOs: 1, 3, and/or 17 and that confers partial or complete resistance to a geminivirus. In some embodiments, the nucleic acid sequence includes a tag sequence that encodes a tag, including but not limited to a tag having an amino acid sequence as set forth in any of SEQ ID NOs: 6, 7, 20, 22, 24, 26, 28, or 37. In some embodiments, the tag sequence is incorporated into the nucleic acid sequence such that upon translation, the tag is incorporated into the resulting protein at its N-terminus or its C-terminus. Stated another way, in some embodiments the tag sequence is operably linked to an in frame with the nucleotide sequence of SEQ ID NO: 1, 3, or 17.

III.A.3. Identifying, Cloning, and Sequencing Nucleic Acids

The cloning and sequencing of the nucleic acids of the presently disclosed subject matter, including but not limited to cDNAs, can be accomplished using techniques known in the art. See generally, Silhavy et al., 1984; Reiter et al., 1992; Schultz et al., 1998; Sambrook & Russell, 2001; Ausubel et al., 2002; and Ausubel et al., 2003.

The isolated nucleic acids and polypeptides of the presently disclosed subject matter are usable over a range of plants—both monocots and dicots—in particular, dicots such as, but not limited to tomato, cassava, cotton, pepper, squash, broccoli, cauliflower, and tobacco. In some embodiments, the monocot is a cereal. In some embodiments, the cereal can be, for example, maize, wheat, barley, oats, rye, millet, sorghum, triticale, *secale*, einkorn, spelt, emmer, teff, milo, flax, gramma grass, *Tripsacum* sp., or teosinte. Other plant genera relevant to the presently disclosed subject matter include, but are not limited to *Cucurbita, Rosa, Vitis, Juglans, Gragaria, Lotus, Medicago, Onobrychis, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum*, Heterocallis, Nemesis, *Pelargonium, Panieum, Pennisetum, Ranunculus, Senecio, Salpiglossis, Cucumis*, Browaalia, Glycine, *Pisum, Phaseolus, Lolium, Oryza, Avena, Hordeum, Secale, Allium*, and *Triticum*.

The presently disclosed subject matter also provides a method for genotyping a plant or plant part comprising a nucleic acid molecule of the presently disclosed subject matter. Optionally, the plant is a monocot such as, but not limited to, rice or wheat. Further optionally, the plant is a dicot such as, but not limited to, tomato, pepper, cotton, squash, broccoli, cauliflower, cassava, and tobacco. Genotyping provides a methodology for distinguishing homologs of a chromosome pair and can be used to differentiate segregants in a plant population. Molecular marker methods can be used in phylogenetic studies, characterizing genetic relationships among crop varieties, identifying crosses or somatic hybrids, localizing chromosomal segments affecting monogenic traits, mapping based cloning, and the study of quantitative inheritance (see Clark, 1997; Paterson, 1996).

The method for genotyping can employ any number of molecular marker analytical techniques including, but not limited to, restriction length polymorphisms (RFLPs). As is well known in the art, RFLPs are produced by differences in the DNA restriction fragment lengths resulting from nucleotide differences between alleles of the same gene. Thus, the presently disclosed subject matter provides a method for following segregation of a gene or nucleic acid of the presently disclosed subject matter or chromosomal sequences genetically linked by using RFLP analysis. Linked chromosomal sequences are in some embodiments within 50 centimorgans (cM), in some embodiments within 40 cM, in some embodiments within 30 cM, in some embodiments within 20 cM, in some embodiments within 10 cM, and in some embodiments within 5, 3, 2, or 1 cM of the nucleic acid of the presently disclosed subject matter.

Embodiments of the presently disclosed subject matter also relate to an isolated nucleic acid molecule comprising a nucleotide sequence, its complement (for example, its full complement), or its reverse complement (for example, its full reverse complement), the nucleotide sequence encoding a polypeptide (for example, a biologically active polypeptide). In some embodiments, the nucleotide sequence encodes a polypeptide comprising a polypeptide sequence listed in SEQ ID NOs: 2, 4, or 18, or a functional fragment, domain, repeat, feature, or chimera thereof. In some embodiments, the nucleotide sequence encodes a polypeptide comprising a polypeptide sequence having substantial identity to a polypeptide sequence listed in SEQ ID NOs: 2, 4, or 18, or a functional fragment, domain, repeat, feature, or chimera thereof. In some embodiments, the nucleotide sequence encodes a polypeptide comprising a polypeptide sequence encoded by a nucleotide sequence identical to or having substantial identity to a nucleotide sequence listed in SEQ ID NOs: 1, 3, or 17, or a functional fragment, domain, or feature thereof, or a sequence complementary thereto. In some embodiments, the nucleotide sequence encodes a polypeptide comprising a polypeptide sequence encoded by a nucleotide sequence capable of hybridizing under medium stringency conditions to a nucleotide sequence listed in SEQ ID NOs: 1, 3, or 17, or to a sequence complementary thereto. In some embodiments, the nucleotide sequence encodes a functional fragment of a polypeptide of the presently disclosed subject matter.

In some embodiments, the isolated nucleic acid comprises a polypeptide-encoding sequence. In some embodiments, the polypeptide-encoding sequence comprises, consists essentially of, or consists of a nucleotide sequence as set forth in SEQ ID NOs: 1, 3, or 17 and/or that encodes a polypeptide comprising, consisting essentially of, or consists of an amino acid sequence as set forth in SEQ ID NOs: 2, 4, or 18, or a functional fragment thereof. In some embodiments, the polypeptide-encoding sequence comprises a 20 base pair nucleotide portion identical in sequence to a consecutive 20 base pair nucleotide portion of a nucleic acid sequence listed in SEQ ID NOs: 2, 4, or 18. In some embodiments, the polypeptide is a plant polypeptide. In some embodiments, the plant is a dicot. In some embodiments, the plant is a gymnosperm. In some embodiments, the plant is a monocot. In some embodiments, the monocot is a cereal. In some embodiments, the cereal includes, but is not limited to, maize, wheat, barley, oats, rye, millet, sorghum, triticale, *secale*, einkorn, spelt, emmer, teff, miloflax, gramma grass, *Tripsacum*, and teosinte. In some embodiments, the plant is a dicot such as, but not limited to tomato, cassava, cotton, pepper, squash, broccoli, cauliflower, and tobacco.

Embodiments of the presently disclosed subject matter also relate to an isolated nucleic acid molecule comprising a nucleotide sequence, its complement (for example, its full complement), or its reverse complement (for example, its full reverse complement), encoding a polypeptide selected from the group consisting of (a) a polypeptide sequence listed in SEQ ID NOs: 2, 4, or 18, or a functional fragment, domain, repeat, feature, or chimera thereof; (b) a polypeptide sequence having substantial identity to (a); (c) a polypeptide having an amino acid sequence that is at least 60% identical to and having a same function as a polypeptide having an amino acid sequence of one of SEQ ID NOs: 2, 4, or 18 (e.g. the same polypeptide having an amino acid sequence of one of SEQ ID NO: 2, 4, or 18 to which it has at least 60% identity); (d) a polypeptide sequence encoded by a nucleotide sequence identical to or having substantial identity to a nucleotide sequence listed in SEQ ID NOs: 1, 3, or 17, or a functional fragment, domain, or feature thereof, or a sequence complementary thereto; (e) a polypeptide sequence encoded by a nucleotide sequence capable of hybridizing under medium stringency conditions to a nucleotide sequence listed in SEQ ID NOs: 1 of 3, or to a sequence complementary thereto; and (f) a functional fragment of (a), (b), (c) or (d).

In some embodiments, the polypeptide having substantial identity comprises an allelic variant of a polypeptide sequence listed in SEQ ID NOs: 2, 4, or 18, or a functional fragment, domain, repeat, feature, or chimera thereof. In some embodiments, the isolated nucleic acid comprises a plurality of regions from the polypeptide sequence encoded by a nucleotide sequence identical to or having substantial identity to a nucleotide sequence listed in SEQ ID NOs: 1, 3, or 17, or a functional fragment, domain, or feature thereof, or a sequence complementary thereto.

In some embodiments, the sequence of the isolated nucleic acid encodes a polypeptide useful for generating an antibody having immunoreactivity against a polypeptide encoded by a nucleotide sequence listed in SEQ ID NOs: 1, 3, or 17, or a functional fragment, domain, or feature thereof. In some embodiments, the presently disclosed subject matter relates to an antibody that having immunoreactivity against a polypeptide encoded by a nucleotide sequence listed in SEQ ID NOs: 1, 3, or 17, or a functional fragment, domain, or feature thereof.

Figure 10B:
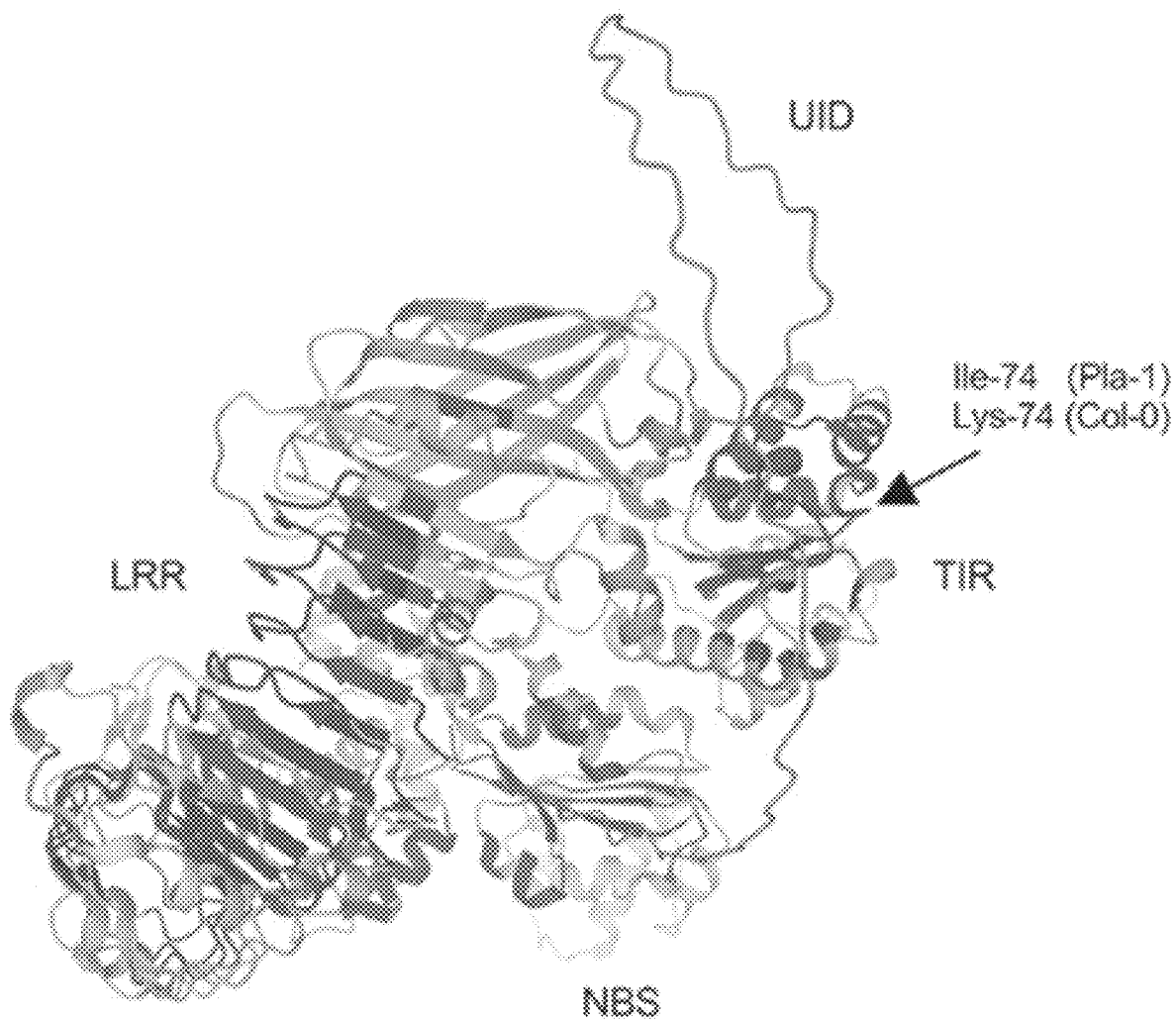

Whereas the presently disclosed subject matter can in some embodiments employ any of SEQ ID NOs: 1-4, functional equivalents thereof including but not limited to functional subsequences thereof, and variants thereof that have nucleotide or amino acid sequences that are at least 60%, 65%, 70%, 75%, 80%, 85%, 90%, 91%, 92%, 93%, 94%, 95%, 96%, 97%, 98%, or at least 99% identical to any one of SEQ ID NOs: 1-4 or any functional equivalent thereof, in some embodiments the nucleic acid or amino acid molecule is derived from a plant other than *Arabidopsis*. It is known that plants other than *Arabidopsis* are susceptible to geminivirus infection, and resistance genes and gene products similar to (e.g., orthologous to) those of the presently disclosed subject matter can also be employed in the presently disclosed compositions and methods. Exemplary such resistance genes and gene products include those disclosed in the following Accession Nos. of the GENBANK® biosequence database: KAG7648161.1 and KAG7532492.1 (*Arabidopsis thaliana* x *Arabidopsis arenosa* Winged helix DNA-binding domain superfamily member), KAG7656088.1 (Toll/interleukin-1 receptor homology (TIR) domain from *Arabidopsis suecica*), KAG7656332.1 (Toll/interleukin-1 receptor homology (TIR) domain from *Arabidopsis suecica*), EFH39673.1 and XP_020878609.1 (*Arabidopsis lyrata* subsp. lyrate), XP_010441602.1 and XP_010441603.1 (Camelina *sativa*), XP_006281533.1 (*Capsella rubella*), and others. In some embodiments, any of these related gene products can be modified at positions that correspond to those that have been modified in the Pla-1 gene products disclosed herein relative to the Col-0 gene products (see e.g., FIG. 10A).

III.B. Polypeptides

The presently disclosed subject matter further relates to isolated polypeptides. In some embodiments, the presently disclosed polypeptides are selected from the group consisting of (a) a polypeptide having an amino acid sequence of one of SEQ ID NOs: 2, 4, and/or 18; (b) a polypeptide having an amino acid sequence that is at least 90%, 91%, 92%, 93%, 94%, 95%, 06%, 97%, 98%, or 99% identical to and having a same function as a polypeptide having an amino acid sequence of one of SEQ ID NOs: 2, 4, and/or 18; (c) a polypeptide having an amino acid sequence encoded by a nucleotide sequence that is at least about 90% identical to a nucleotide sequence of one of SEQ ID NOs: 1, 3, and/or 17; (d) a polypeptide having an amino acid sequence encoded by a nucleic acid molecule capable of hybridizing under highly stringent conditions to a nucleic acid molecule of one of one of SEQ ID NOs: 1, 3, and/or 17 or to a sequence fully complementary thereto; and (e) a functional fragment of a polypeptide encoded by a nucleic acid molecule encoding the amino acid sequence of (a), (b), (c), or (d). In some embodiments, a polypeptide of the presently disclosed subject matter functions in geminivirus resistance, optionally by providing partial or complete resistance to a geminivirus. In some embodiments, the geminivirus is selected from the group consisting of a begomovirus, a mastrevirus, and a curtovirus. In some embodiments, the partial or complete resistance is characterized by a reduction in or an elimination of leaf chlorosis and/or leaf curling in a plant that comprises the polypeptide and/or the functional fragment of the presently disclosed subject matter as compared to the degree of leaf chlorosis and/or leaf curling that the same plant under the same circumstances would have had had it not comprised the polypeptide and/or the functional fragment of the presently disclosed subject matter. In some embodiments, the geminivirus is associated with a disease selected from the group consisting of tomato yellow leaf curl disease, cassava mosaic disease, or cotton left curl disease.

In some embodiments, the polypeptide comprises a chimera of a polypeptide sequence listed in any one of SEQ ID NOs: 2, 4, and/or 18, where the chimera can comprise functional polypeptide motifs, including domains, repeats, post-translational modification sites, or other features. In some embodiments, the polypeptide is a plant polypeptide. In some embodiments, the plant is a dicot. In some embodiments, the plant is a gymnosperm. In some embodiments, the plant is a monocot. In some embodiments, the monocot is a cereal. In some embodiments, the cereal is, for example, maize, wheat, barley, oats, rye, millet, sorghum, triticale, *secale*, einkorn, spelt, emmer, teff, milo, flax, gramma grass, *Tripsacum*, or teosinte. In some embodiments, the plant is a dicot such as, but not limited to tomato, cassava, cotton, pepper, squash, broccoli, cauliflower, and tobacco.

In some embodiments, the polypeptide is expressed in a specific location or tissue of a plant. In some embodiments, the location or tissue includes, but is not limited to, epidermis, root, vascular tissue, meristem, cambium, cortex, pith, leaf, flower, and combinations thereof. In some embodiments, the location or tissue is a seed.

In some embodiments, the polypeptide is involved in a function such as geminivirus-caused disease resistance, enhanced yield, and/or nutritional quality or composition. In some embodiments, the polypeptide is involved in geminivirus resistance.

In some embodiments, isolated polypeptides comprise the amino acid sequences set forth in SEQ ID NOs: 2, 4, or 18, and variants having conservative amino acid modifications. The term "conservative modified variants" refers to polypeptides that can be encoded by nucleic acid sequences having degenerate codon substitutions wherein at least one position of one or more selected (or all) codons is substituted with mixed-base and/or deoxyinosine residues (Batzer et al., 1991; Ohtsuka et al., 1985; Rossolini et al., 1994). Additionally, one skilled in the art will recognize that individual substitutions, deletions, or additions to a nucleic acid, peptide, polypeptide, or polypeptide sequence that alters, adds, or deletes a single amino acid or a small percentage of amino acids in the encoded sequence is a "conservative modification" where the modification results in the substitution of an amino acid with a chemically similar amino acid. Conservative modified variants provide similar biological activity as the unmodified polypeptide. Conservative substitution tables listing functionally similar amino acids are known in the art. See Creighton, 1984.

The term "conservatively modified variant" also refers to a peptide having an amino acid residue sequence substantially identical to a sequence of a polypeptide of the presently disclosed subject matter in which one or more residues have been conservatively substituted with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Amino acid substitutions, such as those which might be employed in modifying the polypeptides described herein, are generally based on the relative similarity of the amino acid side-chain substituents, for example, their hydrophobicity, hydrophilicity, charge, size, and the like. An analysis of the size, shape, and type of the amino acid side-chain substituents reveals that arginine, lysine, and histidine are all positively charged residues; that alanine, glycine, and serine are all of similar size; and that phenylalanine, tryptophan, and tyrosine all have a generally similar shape. Therefore, based upon these considerations, arginine, lysine, and histidine; alanine, glycine, and serine; and phenylalanine, tryptophan, and tyrosine; are defined herein as biologically functional equivalents. Other biologically functionally equivalent changes will be appreciated by those of skill in the art.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids can be substituted for other amino acids having a similar hydropathic index or score and still retain a similar biological activity. Substitutions of amino acids involve amino acids for which the hydropathic indices are in some embodiments within ±2 of the original value, in some embodiments within ±1 of the original value, and in some embodiments within ±0.5 of the original value in making changes based upon the hydropathic index.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Substitutions of amino acids involve amino acids for which the hydrophilicity values are in some embodiments within ±2 of the original value, in some embodiments within ±1 of the original value, and in some embodiments within ±0.5 of the original value in making changes based upon similar hydrophilicity values.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

In an alternative embodiment, the sequence having substantial identity contains a deletion or insertion of at least one amino acid. In some embodiments, the deletion or insertion is of less than about ten amino acids. In some embodiments, the deletion or insertion is of less than about three amino acids.

In some embodiments, the sequence having substantial identity encodes a substitution in at least one amino acid.

Embodiments of the presently disclosed subject matter also provide an isolated polypeptide comprising, consisting essentially of, or consisting of a polypeptide sequence selected from the group consisting of (a) a polypeptide sequence listed in SEQ ID NO: 2, 4, or 18, or a domain or feature thereof, (b) a polypeptide sequence having substantial identity to (a); (c) a polypeptide having an amino acid sequence that is at least 60% identical to and having a same function as a polypeptide having an amino acid sequence of one of SEQ ID NO: 2, 4, or 18 (e.g. the same polypeptide having an amino acid sequence of one of SEQ ID NO: 2, 4, or 18 to which it has at least 60% identity); (d) a polypeptide sequence encoded by a nucleotide sequence identical to or having substantial identity to a nucleotide sequence listed in SEQ ID NO: 1, 3, or 17, or an exon, domain, or feature thereof, or a sequence complementary thereto; (e) a polypeptide sequence encoded by a nucleotide sequence capable of hybridizing under medium stringency conditions to a nucleotide sequence listed in SEQ ID NO: 1, 3, or 17, or to a sequence complementary thereto; and (f) a functional fragment of (a), (b), (c) or (d).

In some embodiments, a polypeptide having substantial identity to a polypeptide sequence listed in SEQ ID NO: 2, 4, or 18, or a domain or feature thereof, is an allelic variant of the polypeptide sequence listed in SEQ ID NO: 2, 4, or 18. In some embodiments, a polypeptide having substantial identity to a polypeptide sequence listed in SEQ ID NO: 2, 4, or 18, or a domain or feature thereof, is a naturally occurring variant of the polypeptide sequence listed in SEQ ID NO: 2, 4, or 18. In some embodiments, a polypeptide having substantial identity to a polypeptide sequence listed in SEQ ID NO: 2, 4, or 18, or a domain or feature thereof, is a polymorphic variant of the polypeptide sequence listed in SEQ ID NO: 2, 4, or 18.

In some embodiments, the polypeptide is a polypeptide comprising one of the amino acid sequences listed in SEQ ID NO: 2, 4, or 18. In some embodiments, the polypeptide is a functional fragment or domain of a polypeptide comprising one of the amino acid sequences listed in SEQ ID NOs: 2, 4, and/or 18. In some embodiments, the polypeptide is a chimera, where the chimera comprises a functional polypeptide domain, including, but not limited to, a domain, a repeat, a post-translational modification site, and combinations thereof. In some embodiments, the polypeptide is a plant polypeptide. In some embodiments, the plant is a dicot. In some embodiments, the plant is a gymnosperm. In some embodiments, the plant is a monocot. In some embodiments, the monocot is a cereal. In some embodiments, the cereal can be, for example, maize, wheat, barley, oats, rye, millet, sorghum, triticale, *secale*, einkorn, spelt, emmer, teff, milo, flax, gramma grass, *Tripsacum*, or teosinte. In some embodiments, the plant is a dicot such as, but not limited to tomato, cassava, cotton, pepper, squash, broccoli, cauliflower, and tobacco.

In some embodiments, the polypeptide is expressed in a specific location or tissue of a plant. In some embodiments, the location or tissue includes, but is not limited to, epidermis, vascular tissue, meristem, cambium, cortex, or pith. In some embodiments, the location or tissue is leaf or sheath, root, flower, and developing ovule or seed. In some embodiments, the location or tissue can be, for example, epidermis, root, vascular tissue, meristem, cambium, cortex, pith, leaf, or flower. In some embodiments, the location or tissue is a seed.

In some embodiments, the polypeptide sequence is encoded by a nucleotide sequence having substantial identity to a nucleotide sequence listed in SEQ ID NO: 1, 3, or 17 or a functional fragment, domain, or feature thereof or a sequence complementary thereto, wherein the nucleotide sequence includes a deletion or insertion of at least one nucleotide. In some embodiments, the deletion or insertion is of less than about thirty nucleotides. In some embodiments, the deletion or insertion is of less than about five nucleotides. In some embodiments, the polypeptide sequence encoded by a nucleotide sequence having substantial identity to a nucleotide sequence listed in SEQ ID NO: 1, 3, or 17, or a functional fragment, domain, or feature thereof or a sequence complementary thereto, includes a substitution of at least one codon. In some embodiments, the substitution is conservative. In some embodiments, the polypeptide sequences having substantial identity to the polypeptide sequence listed in SEQ ID NO: 2, 4, or 18, or a functional fragment, domain, repeat, feature, or chimera thereof, includes a deletion or insertion of at least one amino acid.

The polypeptides of the presently disclosed subject matter, fragments thereof, or variants thereof, can comprise any number of contiguous amino acid residues from a polypeptide of the presently disclosed subject matter, wherein the number of residues is selected from the group of integers consisting of from 10 to the number of residues in a full-length polypeptide of the presently disclosed subject matter. In some embodiments, the portion or fragment of the polypeptide is a functional polypeptide. The presently disclosed subject matter includes active polypeptides having specific activity of at least in some embodiments 20%, in some embodiments 30%, in some embodiments 40%, in some embodiments 50%, in some embodiments 60%, in some embodiments 70%, in some embodiments 80%, in some embodiments 90%, and in some embodiments 95% that of the native (non-synthetic) endogenous polypeptide. Further, the substrate specificity (kcat/Km) can be substantially identical to the native (non-synthetic), endogenous polypeptide. Typically, the Km will be at least in some embodiments 30%, in some embodiments 40%, in some embodiments 50% of the native, endogenous polypeptide; and in some embodiments at least 60%, in some embodiments 70%, in some embodiments 80%, and in some embodiments 90% of the native, endogenous polypeptide. Methods for assaying and quantifying measures of activity and substrate specificity are well known to those of skill in the art.

The isolated polypeptides of the presently disclosed subject matter can elicit production of an antibody specifically reactive to a polypeptide of the presently disclosed subject matter when presented as an immunogen. Therefore, the polypeptides of the presently disclosed subject matter can be employed as immunogens for constructing antibodies immunoreactive to a polypeptide of the presently disclosed subject matter for such purposes including, but not limited to, immunoassays or polypeptide purification techniques. Immunoassays for determining binding are well known to those of skill in the art and include, but are not limited to, enzyme-linked immunosorbent assays (ELISAs) and competitive immunoassays.

Embodiments of the presently disclosed subject matter also relate to chimeric polypeptides encoded by the isolated nucleic acid molecules of the present disclosure including a chimeric polypeptide containing a polypeptide sequence encoded by an isolated nucleic acid containing a nucleotide sequence selected from the group consisting of (a) a nucleotide sequence listed in SEQ ID NO: 1, 3, or 17, or an exon, domain, or feature thereof, (b) a nucleotide sequence having substantial identity to (a); (c) a nucleotide sequence at least about 60% identical to (a); (d) a nucleotide sequence capable of hybridizing to (a) under medium stringency; (e) a nucleotide sequence complementary (for example, fully complementary) to (a), (b) or (c); and (f) a nucleotide sequence which is the reverse complement (for example, full reverse complement) of (a), (b) or (c); (g) or a functional fragment thereof.

Also, a polypeptide containing a polypeptide sequence encoded by an isolated nucleic acid containing a nucleotide sequence, its complement, or its reverse complement, encoding a polypeptide including a polypeptide sequence including (a) a polypeptide sequence listed in SEQ ID NO: 2, 4, or 18, or a domain, repeat, feature, or chimeras thereof, (b) a polypeptide sequence having substantial identity to (a); (c) a polypeptide sequence encoded by a nucleotide sequence identical to or having substantial identity to a nucleotide sequence listed in SEQ ID NO: 1, 3, or 17, or a domain or feature thereof, or a sequence complementary thereto; (d) a polypeptide sequence encoded by a nucleotide sequence capable of hybridizing under medium stringency conditions to a nucleotide sequence listed in SEQ ID NO: 1, 3, or 17, or to a sequence complementary thereto; and (e) a functional fragment of (a), (b), (c) or (d).

III.C. Compositions Comprising Nucleic Acids and/or Polypeptides

In some embodiments, the presently disclosed subject matter provides a novel sequence of a gene in *Arabidopsis thaliana* Pla-1 that confers resistance to geminiviruses. The gene is an NLR gene, and its gene ID is AT1G31540. However, it has differences in DNA and amino acid sequences with the AT1G31540 from *A. thaliana* Col-0 (the originally sequenced accession). In some embodiments, the Pla-1 gene product that confers resistance to geminiviruses and/or that suppresses a disease associated with geminivirus infection comprises, consists essentially of, or consists of an amino acid sequence as set forth in SEQ ID NO: 2. In some embodiments, *A. thaliana* susceptible lines containing a transgene in accordance with the presently disclosed subject matter that show resistance to geminiviruses have been produced. In some embodiments, a tomato, cassava, or cotton line is modified to show the resistance. In some embodiments, crops that can be modified to show resistance in accordance with the presently disclosed subject matter include but are not limited to tomato, cassava, cotton, chili pepper, potato and other solanaceous plants, beet, cucurbits, maize, wheat, and many others, including many weeds. In some embodiments, the presently disclosed subject matter affords protections against dicot-infecting geminiviruses and against monocot-infecting geminiviruses. In some embodiments, to develop resistance in other plant species, the presently disclosed gene from *Arabidopsis* is used as a transgene. In some embodiments, a constitutive promoter is employed with the transgene. In some embodiments, to develop resistance in other plant species, a native gene is identified and edited based on the manageability of the edits. In some embodiments, to develop resistance in other plant species, an allele already present in a variety of a plant is bred into elite lines.

With regard to gain-of-function or loss-of-function, it has been shown that when the gene is present, the partial or complete resistance can be shown. And some evidence exists that suggest that is a dose response trait. Further, it has been shown that overexpression of AT1G31540 from Pla-1 in *A. thaliana* Col-0 provides resistance against cabbage leaf curl virus in still segregating transgenic plants (T2). In some embodiments, the homozygous T3 lines are also tested.

IV. Controlling and Altering the Expression of Nucleic Acid Molecules

One aspect of the presently disclosed subject matter provides compositions and methods for altering (i.e. increasing or decreasing) the level of nucleic acid molecules and/or polypeptides of the presently disclosed subject matter in plants. In particular, the nucleic acid molecules and polypeptides of the presently disclosed subject matter are expressed constitutively, temporally, or spatially (e.g. at developmental stages), in certain tissues, and/or quantities, which are uncharacteristic of non-recombinantly engineered plants. Therefore, the presently disclosed subject matter provides utility in such exemplary applications as altering the specified characteristics identified above.

The isolated nucleic acid molecules of the presently disclosed subject matter are useful for expressing a polypeptide of the presently disclosed subject matter in a recombinantly engineered cell such as a bacterial, yeast, insect, mammalian, or plant cell. Expressing cells can produce the polypeptide in a non-natural condition (e.g. in quantity, composition, location and/or time) because they have been genetically altered to do so. Those skilled in the art are knowledgeable in the numerous expression systems available for expression of nucleic acids encoding a polypeptide of the presently disclosed subject matter.

Embodiments of the presently disclosed subject matter provide an expression cassette comprising a promoter sequence operatively linked to an isolated nucleic acid, the isolated nucleic acid comprising (a) a nucleotide sequence listed in SEQ ID NO: 1, 3, or 17, or a functional fragment, domain, or feature thereof; (b) a nucleotide sequence having substantial identity to (a); (c) a nucleotide sequence at least 60% identical to (a); (d) a nucleotide sequence capable of hybridizing to (a) under medium stringency; (e) a nucleotide sequence complementary (for example, fully complementary) to (a), (b) or (c); and (f) a nucleotide sequence which is the reverse complement (for example, the full reverse complement) of (a), (b) or (c).

Further encompassed within the presently disclosed subject matter is a recombinant vector comprising an expression cassette according to the embodiments of the presently disclosed subject matter. Also encompassed are plant cells comprising expression cassettes according to the present disclosure, and plants comprising these plant cells. In some embodiments, the plant is a dicot. In some embodiments, the plant is a gymnosperm. In some embodiments, the plant is a monocot. In some embodiments, the monocot is a cereal. In some embodiments, the cereal is, for example, maize, wheat, barley, oats, rye, millet, sorghum, triticale, *secale*, einkorn, spelt, emmer, teff, milo, flax, gramma grass, *Tripsacum* or teosinte. In some embodiments, the plant is a dicot such as, but not limited to tomato, cassava, cotton, pepper, squash, broccoli, cauliflower, and tobacco.

In some embodiments, the expression cassette is expressed throughout the plant. In some embodiments, the expression cassette is expressed in a specific location or tissue of a plant. In some embodiments, the location or tissue includes, but is not limited to, epidermis, root, vascular tissue, meristem, cambium, cortex, pith, leaf, flower, and combinations thereof. In some embodiments, the location or tissue is a seed.

In some embodiments, the expression cassette is involved in a function including, but not limited to, disease resistance and/or disease processes (for example, geminivirus resistance). In some embodiments, the chimeric polypeptide is involved in a function such as resistance to geminivirus-associated disease, enhanced yield, or nutritional composition.

Embodiments of the presently disclosed subject matter also relate to an expression vector comprising a nucleic acid molecule selected from the group consisting of (a) a nucleic acid encoding a polypeptide comprising, consisting essentially of, or consisting of an amino acid sequence as set forth in SEQ ID NO: 2, 4, or 18; (b) a functional fragment, domain, or featured region comprising, consisting essentially of, or consisting of an amino acid sequence as set forth in SEQ ID NO: 2, 4, or 18; and (c) a complete nucleic acid sequence comprising, consisting essentially of, or consisting of a nucleotide sequence as set forth in SEQ ID NO: 1, 3, or 17, or a functional fragment thereof, in combination with a heterologous sequence.

Thus, in some embodiments the presently disclosed subject matter relates to methods for altering the expression of a polypeptide as disclosed herein in a plant, the method comprising expressing an expression cassette encoding a polypeptide as disclosed herein in the plant. In some embodiments, the polypeptide is expressed in a predetermined location or tissue of a plant. In some embodiments, the location or tissue is selected from the group consisting of epidermis, root, vascular tissue, meristem, cambium, cortex, pith, leaf, flower, seed, and combinations thereof.

In some embodiments, the expression vector comprises one or more elements including, but not limited to, a promoter-enhancer sequence, a selection marker sequence, an origin of replication, an epitope tag-encoding sequence, and an affinity purification tag-encoding sequence. In some embodiments, the promoter-enhancer sequence comprises, for example, the cauliflower mosaic virus (CaMV) 35S promoter, the CaMV 19S promoter, the *Arabidopsis* TCTP promoter, the *Arabidopsis* UBQ1 promoter, the tobacco PR-1a promoter, the ubiquitin promoter, or the phaseolin promoter. In some embodiments, the promoter is operable in plants, and in some embodiments, the promoter is a constitutive or inducible promoter. In some embodiments, the selection marker sequence encodes an antibiotic resistance gene. In some embodiments, the epitope tag sequence encodes a V5 tag (e.g., GKPIPNPLLGLDST; SEQ ID NO: 6; Southern et al., 1991), a peptide FHHTT tag (e.g., SEQ ID NO: 7), a hemagglutinin (HA) tag (e.g., SEQ ID NO: 37), a His6 tag (e.g., SEQ ID NO: 22), a FLAG tag (e.g., SEQ ID NO: 24), an E-tag (SEQ ID NO: 26 or 28), a glutathione-S-transferase tag, or any combination thereof. In some embodiments the affinity purification tag sequence encodes a polyamino acid sequence or a polypeptide. In some embodiments, the polyamino acid sequence comprises polyhistidine. In some embodiments, the polypeptide is chitin-binding domain or glutathione-S-transferase. In some embodiments, the affinity purification tag sequence comprises an intein encoding sequence. In some embodiments, the tagged cassette comprises SEQ ID NO: 17 or encodes SEQ ID NO: 18. With respect to SEQ ID NOs: 17 and 18, these sequences encode or comprise an HA tag (SEQ ID NO: 37), but one of ordinary skill in the art would know how to substitute any other epitope tag for the HA tag present therein, including but not limited to a myc tag (such as but not limited to SEQ ID NO: 20, optionally encoded by SEQ ID NO: 19), a His6 tag (such as but not limited to SEQ ID NO: 22, optionally encoded by SEQ ID NO: 21), a FLAG tag (such as but not limited to SEQ ID NO: 24, optionally encoded by SEQ ID NO: 23), an E-tag (such as but not limited to SEQ ID NO: 26 or SEQ ID NO: 28, optionally encoded by SEQ ID NO: 25 or SEQ ID NO: 27, respectively), a V5 tag (such as but not limited to SEQ ID NO: 6), or any combination thereof in any order. Similarly, upon review of the instant disclosure, one of ordinary skill in the art would understand how to add any of these tags, alone or in combination, to any of the nucleic acids and polypeptides of the presently disclosed subject matter.

In some embodiments, the expression vector comprises a eukaryotic expression vector, and in some embodiments, the expression vector comprises a prokaryotic expression vector. In some embodiments, the eukaryotic expression vector comprises a tissue-specific promoter. In some embodiments, the expression vector is operable in plants.

Embodiments of the presently disclosed subject matter also relate to a cell comprising a nucleic acid construct comprising an expression vector and a nucleic acid comprising a nucleic acid encoding a polypeptide comprising, consisting essentially of, or consisting of an amino acid sequence as set forth in SEQ ID NO: 2, 4, or 18, or a nucleic acid sequence comprising, consisting essentially of, or consisting of a nucleotide sequence as set forth in SEQ ID NO: 1, 3, or 17, or a subsequence thereof, in combination with a heterologous sequence.

In some embodiments, the cell is a bacterial cell, a fungal cell, a plant cell, or an animal cell. In some embodiments, the polypeptide is expressed in a specific location or tissue of a plant. In some embodiments, the location or tissue includes, but is not limited to, epidermis, root, vascular tissue, meristem, cambium, cortex, pith, leaf, flower, and combinations thereof. In an alternative embodiment, the location or tissue is a seed. In some embodiments, the polypeptide is involved in a function such as, for example, carbon metabolism, photosynthesis, signal transduction, cell growth, reproduction, disease processes, gene regulation, and differentiation. In some embodiments, the polypeptide is involved in a function such as resistance to geminivirus-associated disease, enhanced yield, or nutritional composition.

Prokaryotic cells including, but not limited to, *Escherichia coli* and other microbial strains known to those in the art, can be used a host cells. Methods for expressing polypeptides in prokaryotic cells are well known to those in the art and can be found in many laboratory manuals such as Sambrook & Russell, 2001. A variety of promoters, ribosome binding sites, and operators to control expression are available to those skilled in the art, as are selectable markers such as antibiotic resistance genes. The type of vector is chosen to allow for optimal growth and expression in the selected cell type.

A variety of eukaryotic expression systems are available such as, for example, yeast, insect cell lines, plant cells, and mammalian cells. Expression and synthesis of heterologous polypeptides in yeast is well known (see Sherman et al., 1982). Yeast strains widely used for production of eukaryotic polypeptides are *Saccharomyces cerevisiae* and *Pichia pastoris*, and vectors, strains, and protocols for expression are available from commercial suppliers (e.g., Invitrogen Corp., Carlsbad, California, United States of America).

Mammalian cell systems can be transformed with expression vectors for production of polypeptides. Suitable host cell lines available to those in the art include, but are not limited to, the HEK293, BHK21, and CHO cells lines. Expression vectors for these cells can include expression control sequences such as an origin of replication, a promoter, (e.g., the CMV promoter, a Herpes Simplex Virus thymidine kinase (HSV-tk) promoter or phosphoglycerate kinase (pgk) promoter), an enhancer, and polypeptide processing sites such as ribosome binding sites, RNA splice sites, polyadenylation sites, and transcription terminator sequences. Other animal cell lines useful for the production of polypeptides are available commercially or from depositories such as the American Type Culture Collection (ATCC; Manassas, Virginia, United States of America).

Expression vectors for expressing polypeptides in insect cells are usually derived from baculovirus or other viruses known in the art. A number of suitable insect cell lines are available including, but not limited to, mosquito larvae, silkworm, armyworm (for example, Spodopterafrugiperda), moth, and Drosophila cell lines.

Methods for transforming eukaryotic cells are known. Numerous methods can be used to introduce exogenous DNA into eukaryotic cells including, but not limited to, calcium phosphate precipitation, fusion of the recipient cell with bacterial protoplasts containing the DNA, treatment of the recipient cells with liposomes containing the DNA, DEAE dextrin, electroporation, biolistics, and microinjection of the DNA directly into the cells. Transformed cells are cultured using techniques that are well known in the art (see Kuchler, 1997).

Agrobacterium-Mediated Transformation.

An exemplary method for introducing an expression vector into plants is based on the natural transformation system ofAgrobacterium. See e.g., Valles et al., 1984; Horsch et al., 1985; Jefferson et al., 1987; Dinant et al., 1997. A. tumefaciens and A. rhizogenes are plant pathogenic soil bacteria which genetically transform plant cells. The Ti and Ri plasmids of A. tumefaciens and A. rhizogenes, respectively, carry genes responsible for genetic transformation of the plant. See e.g., Kado & Hooykaas, 1991. Descriptions of Agrobacterium vector systems and methods for Agrobacterium-mediated gene transfer are also disclosed in Gruber et al., 1993; Miki et al., 1993; Moloney et al., 1989; and U.S. Pat. No. 5,591,616

Direct Gene Transfer.

Despite the fact the host range for Agrobacterium-mediated transformation is broad, some major crop species have generally been recalcitrant to this mode of gene transfer, even though some success has been achieved in rice and corn. Hiei et al., 1994; U.S. Pat. No. 5,591,616. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 micron. The expression vector is introduced into plant tissues with a biolistic device that accelerates the microprojectiles to speeds of 300 to 600 m/s which is sufficient to penetrate plant cell walls and membranes. Russell et al., 1993; Aragao et al., 1992; Aragao, 1996; Kim & Minamikawa, 1996; Sanford et al., 1987, Sanford, 1988, Klein et al., 1988, Sanford, 1990, Klein et al., 1992; Gray et al., 1994.

Another method for physical delivery of DNA to plants is sonication of target cells. See Zhang et al., 1991. Alternatively, liposome and spheroplast fusion have been used to introduce expression vectors into plants. See Deshayes et al., 1985 and Christou et al., 1987. Direct uptake of DNA into protoplasts using $CaCl_2$) precipitation, polyvinyl alcohol or poly-L-ornithine has also been reported. See Hain et al., 1985; Draper et al., 1982. Electroporation of protoplasts and whole cells and tissues have also been described. See D'Halluin et al., 1992 and Spencer et al., 1994.

Once a polypeptide of the presently disclosed subject matter is expressed it can be isolated and purified from the expressing cells using methods known to those skilled in the art. The purification process can be monitored using Western blot techniques, radioimmunoassay, or other standard immunoassay techniques. Polypeptide purification techniques are commonly known and used by those skilled in the art (see Scopes, 1982; Deutscher et al., 1990).

Embodiments of the presently disclosed subject matter provide a method for producing a recombinant polypeptide in which the expression vector comprise one or more elements including, but not limited to, a promoter-enhancer sequence, a selection marker sequence, an origin of replication, an epitope tag-encoding sequence, and an affinity purification tag-encoding sequence. In some embodiments, the nucleic acid construct comprises an epitope tag-encoding sequence and the isolating step employs an antibody specific for the epitope tag. In some embodiments, the nucleic acid construct comprises a polyamino acid-encoding sequence and the isolating step employs a resin comprising a polyamino acid binding substance, in some embodiments where the polyamino acid is polyhistidine and the polyamino acid binding resin is nickel-charged agarose resin. In some embodiments, the nucleic acid construct comprises a polypeptide-encoding sequence and the isolating step employs a resin comprising a polypeptide binding substance. In some embodiments, the polypeptide is a chitin-binding domain and the resin contains chitin-SEPHAROSE™.

The polypeptides of the presently disclosed subject matter can be synthesized using non-cellular synthetic methods known to those in the art. Techniques for solid phase synthesis are disclosed in Barany & Merrifield, 1980; Merrifield et al., 1963; Stewart & Young, 1984.

The presently disclosed subject matter further provides a method for modifying (i.e. increasing or decreasing) the concentration or composition of a polypeptide of the presently disclosed subject matter in a plant or part thereof. Modification can be effected by increasing or decreasing the concentration and/or the composition (i.e. the ration of the polypeptides of the presently disclosed subject matter) in a plant. The method comprises introducing into a plant cell an expression cassette comprising a nucleic acid molecule of the presently disclosed subject matter as disclosed above to obtain a transformed plant cell or tissue, and culturing the transformed plant cell or tissue. The nucleic acid molecule can be under the regulation of a constitutive or inducible promoter. The method can further comprise inducing or repressing expression of a nucleic acid molecule of a sequence in the plant for a time sufficient to modify the concentration and/or composition in the plant or plant part.

A plant or plant part having modified expression of a nucleic acid molecule of the presently disclosed subject matter can be analyzed and selected using methods known to those skilled in the art including, but not limited to, Southern blotting, DNA sequencing, or PCR analysis using primers specific to the nucleic acid molecule and detecting amplicons produced therefrom.

In general, a concentration or composition is increased or decreased by at least in some embodiments 5%, in some embodiments 10%, in some embodiments 20%, in some embodiments 30%, in some embodiments 40%, in some embodiments 50%, in some embodiments 60%, in some embodiments 70%, in some embodiments 80%, and in some embodiments 90% relative to a native control plant, plant part, or cell lacking the expression cassette.

Additionally, in some embodiments the presently disclosed subject matter relates to methods for creating populations of plants comprising at least one allele associated with geminivirus resistance, wherein the allele corresponds to AT1G31540 in *Arabidopsis* accession Pla-1 (including but not limited to an allele comprising, consisting essentially of, or consisting of a nucleic acid sequence as set forth in SEQ ID NO: 1, 3, or 17 and/or that encodes a polypeptide comprising, consisting essentially of, or consisting of an amino acid sequence as set forth in SEQ ID NO: 2, 4, or 18), the method comprising (a) genotyping a first population of plants, said population containing at least one allele associated with geminivirus resistance, wherein the allele corresponds to AT1G31540 in *Arabidopsis* accession Pla-1; (b) selecting from said first population one or more identified plants containing said at least one allele associated with geminivirus resistance, wherein the allele corresponds to AT1G31540 in *Arabidopsis* accession Pla-1; and (c) producing from said selected plants a second population, thereby creating a population of plants comprising at least one allele associated with geminivirus resistance, wherein the allele corresponds to AT1G31540 in *Arabidopsis* accession Pla-1. In some embodiments, the first population of plants genotyped in step (a) is a population generated by a cross. In some embodiments, the cross is effected by mechanical emasculation, chemical sterilization, or genetic sterilization of a pollen acceptor. In some embodiments, the genotyping is effected in step (a) by determining the allelic state of at least one genomic DNA marker of the plant. In some embodiments, the selected plant(s) of step (b) exhibit at least partial resistance to a geminivirus or at least substantial resistance to a geminivirus. In some embodiments, the first population of plants is generated by a cross of at least one geminivirus resistant plant with at least one geminivirus sensitive plant. In some embodiments, the first population of plants is a segregating population. In some embodiments, the cross is a back cross of at least one geminivirus resistant plant with at least one geminivirus sensitive plant to introgress geminivirus resistance into a germplasm. In some embodiments, the first population of plants is a haploid breeding population.

Also provided are methods for introgressing one or more geminivirus resistance QTL alleles into plants. In some embodiments, the methods comprise (a) crossing at least one first plant comprising the geminivirus resistance QTL allele, wherein the allele comprises a geminivirus resistance QTL corresponding to a QTL mapped between 8 Mb and 12.7 Mb on chromosome 1 of the *Arabidopsis* accession Pla-1, with at least one second plant in order to form a segregating population; (b) screening said segregating population with one or more nucleic acid markers to determine if one or more plants from said segregating population contain the geminivirus resistance QTL allele; and (c) selecting from said segregating population one or more plants comprising said allele associated with geminivirus resistance QTL. In some embodiments, at least one of the one or more nucleic acid markers is located within 5 cM of said geminivirus resistance QTL. In some embodiments, at least one of the one or more nucleic acid markers is located within 2 cM of said geminivirus resistance QTL. In some embodiments, at least one of the one or more nucleic acid markers is located within 1 cM of said geminivirus resistance QTL. In some embodiments, at least one of the one or more nucleic acid markers exhibits a LOD score of greater than 4.0 with said geminivirus resistance QTL. In some embodiments, the one or more nucleic acid markers comprise an SNP selected from those set forth in Table 2:

TABLE 2

SNPs Employed for Mapping Potential Resistance Genes

| Base position on Col-0 chr. 1* | Col-0 base | Pla-1 base | Base position on Col-0 chr. 1* | Col-0 base | Pla-1 base |
| --- | --- | --- | --- | --- | --- |
| 8,015,459 | C | T | 10,386,772 | G | T |
| 8,107,764 | G | A | 10,493,691 | C | T |
| 8,216,254 | C | T | 10,584,760 | C | T |
| 8,315,857 | A | T | 10,687,200 | T | C |
| 8,417,092 | G | A | 10,788,196 | G | A |
| 8,518,294 | C | G | 10,878,073 | C | A |
| 8,608,446 | C | T | 10,989,217 | T | C |
| 8,715,081 | A | G | 11,091,262 | G | A |
| 8,842,441 | T | A | 11,191,288 | A | C |
| 8,928,144 | A | G | 11,296,101 | T | C |
| 9,016,786 | G | A | 11,395,449 | G | C |
| 9,118,189 | A | T | 11,479,644 | T | C |
| 9,217,175 | C | T | 11,581,529 | C | T |
| 9,319,882 | A | T | 11,680,908 | T | G |
| 9,410,754 | T | A | 11,787,640 | C | G |
| 9,517,294 | A | G | 11,882,691 | G | T |
| 9,590,721 | G | C | 11,976,831 | A | C |
| 9,680,725 | G | C | 12,075,314 | A | G |
| 9,777,541 | C | T | 12,173,690 | A | C |
| 9,886,904 | T | C | 12,275,289 | A | G |
| 9,980,561 | A | G | 12,369,129 | A | G |
| 10,081,934 | G | C | 12,473,862 | C | T |
| 10,179,649 | A | G | 12,586,484 | C | T |
| 10,281,930 | G | A | 12,700,543 | G | A |

*Nucleotide positions based on Accession No. NC_003070.9 of the GENBANK® biosequence database.

The presently disclosed subject matter also provides in some embodiments methods for creating plants comprising at least one allele associated with geminivirus resistance. In some embodiments, the methods comprising (a) identifying in said plant an allele corresponding to ATIG31540 in *Arabidopsis* accession Pla-1; and (b) modifying in said plant said allele that corresponds to ATIG31540 in *Arabidopsis* accession Pla-1 using a genome editing technique, thereby creating a plant comprising at least one allele associated with geminivirus resistance. In some embodiments, the genome editing employs a biological activity selected from the group consisting of CRISPR/cas9, a meganuclease, and/or a zinc finger.

The presently disclosed subject matter will be further disclosed by reference to the following detailed examples. These examples are provided for purposes of illustration only, and are not intended to be limiting unless otherwise specified.

EXAMPLES

The following Examples have been included to illustrate modes of the presently disclosed subject matter. Certain aspects of the following EXAMPLES are described in terms of techniques and procedures found or contemplated by the present co-inventors to work well in the practice of the presently disclosed subject matter. These EXAMPLES illustrate standard laboratory practices of the co-inventors. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Standard recombinant DNA and molecular cloning techniques used here are well known in the art and are disclosed in Silhavy et al., 1984; Reiter et al., 1992; Schultz et al., 1998; Sambrook & Russell, 2001; Ausubel et al., 2002; and Ausubel et al., 2003.

Example 1

Mapping the Pla-1 Resistance Gene

More than 200 *Arabidopsis thaliana* accessions were screened for geminivirus resistance. Plants of the accession Pla-1 was found to be resistant to CaLCuV and BCTV that belong to the genera begomovirus and curtovirus, respectively. The geminivirus resistance in the Pla-1 genome was mapped using around 440 segregating CaLCuV-infected F2 generation plants from a cross between the resistant Pla-1 and the susceptible Col-0. Allele-specific primers for Pla-1 or Col-0 were generated corresponding to selected SNPs at 2.5 Mb intervals across the *Arabidopsis* genome. Genotyping of each F2 plant at each SNP marker was carried out using the Kompetitive Allele-Specific PCR (KASP) technology and the genotypes were determined according to the fluorescence readout of PCR reactions on the genomic DNA of each F2 plant. Symptom severity of each plant was scored to levels of 1 to 5, where score 1 plants showed no symptom and score 5 plants displayed most severe symptoms. The results are presented in FIG. 1B.

Figure 1B:
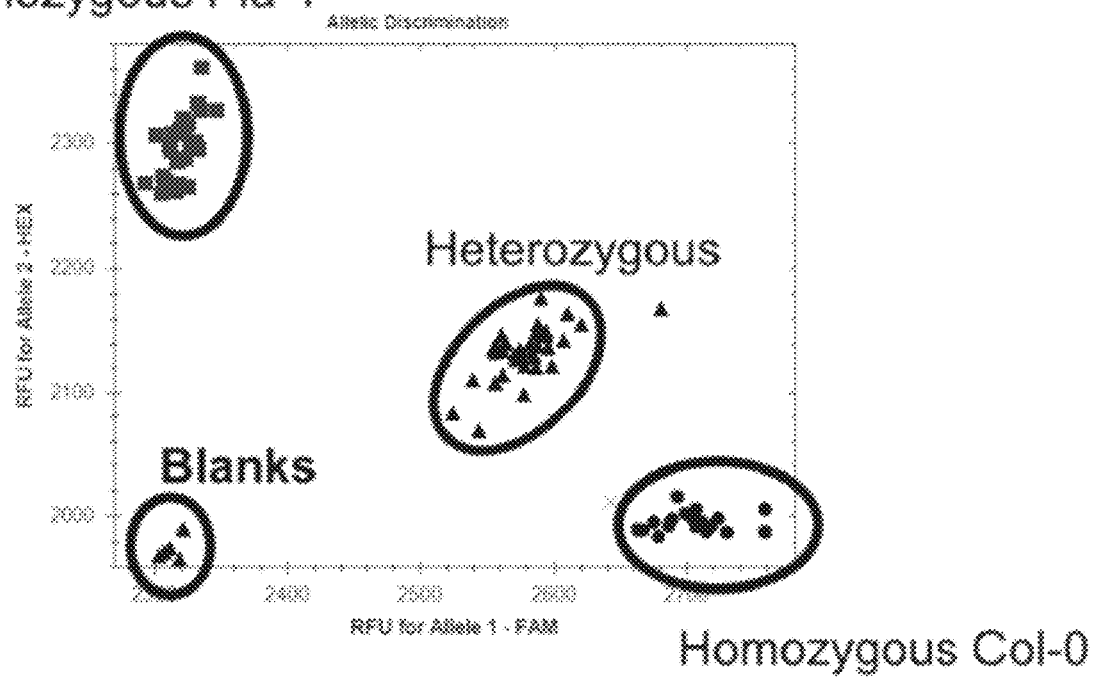
Figure 2:
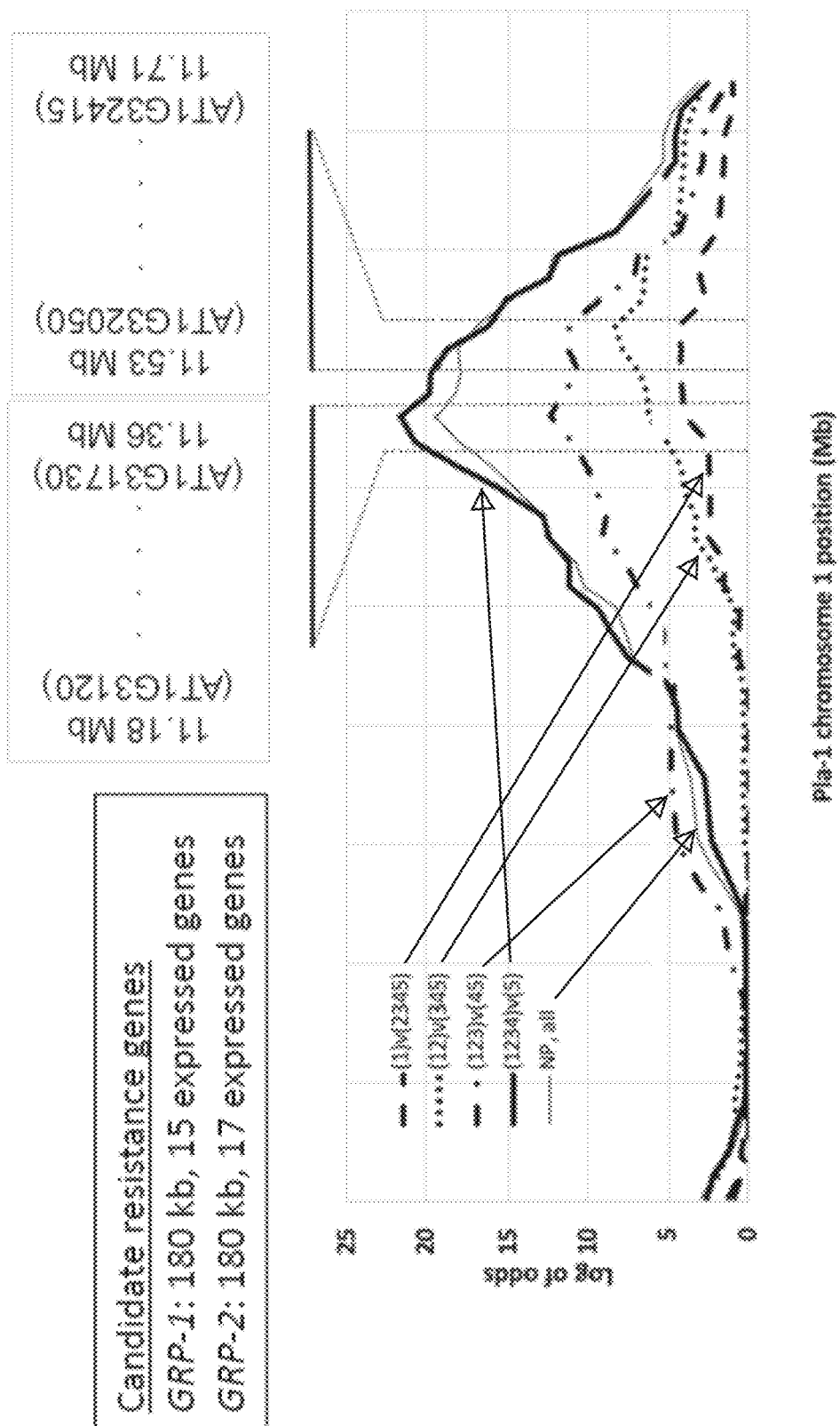
FIG. 2 is a graph showing the results of fine mapping of the resistance locus on Pla-1 chromosome 1.
Figure 3:
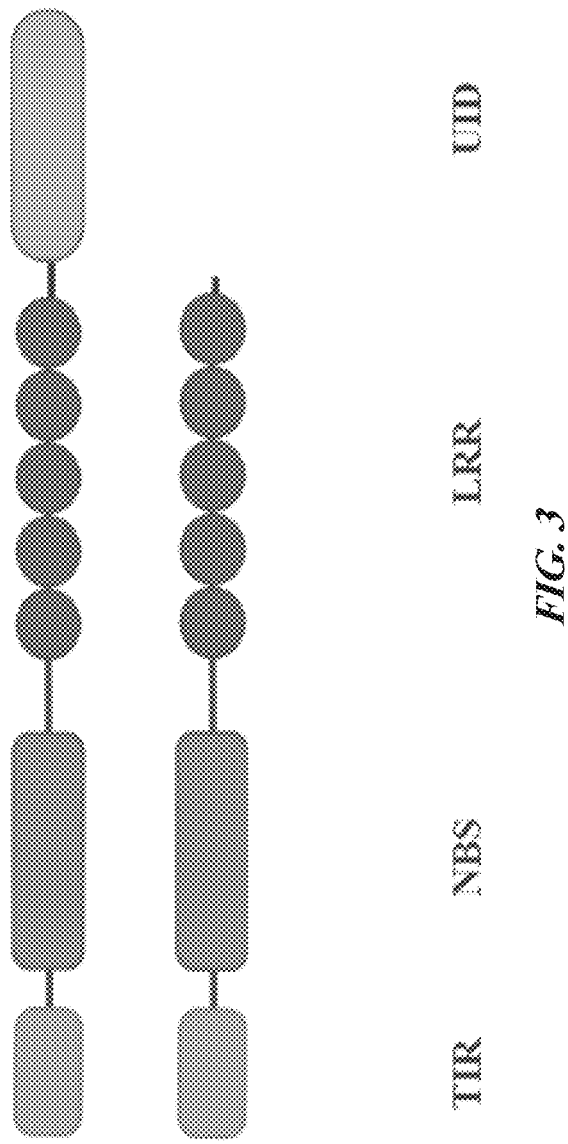
FIG. 3 is a depiction of the various domains of the Pla-1 and Col-0 gene products. The top depiction represents the predominantly expressed longer isoform, which contains an Unusual Integrated Domain (UID). The bottom depiction represents that the shorter isoform, which lacks the UID. The left-most domain (red in a color version of the Figure) corresponds to the Toll-interleukin-1 receptor (TIR) domain, the second to left domain (light blue in a color version of the Figure) corresponds to the nucleotide binding site (NBS) domain, the circles (darker blue in a color version of the Figure) correspond to the leucine-rich repeat (LRR) domain, and the right-most domain in the top and bottom depictions (gold in a color version of the Figure) corresponds to the UID domain. As between the wild type (Col-0) gene product and the resistance (Pla-1) gene product, the TIR domain showed one (1) amino acid difference, the NBS domain showed 0 amino acid differences, the LRR domain showed 18 amino acid differences, and the UID domain showed 11 amino acid differences.
Figure 5:
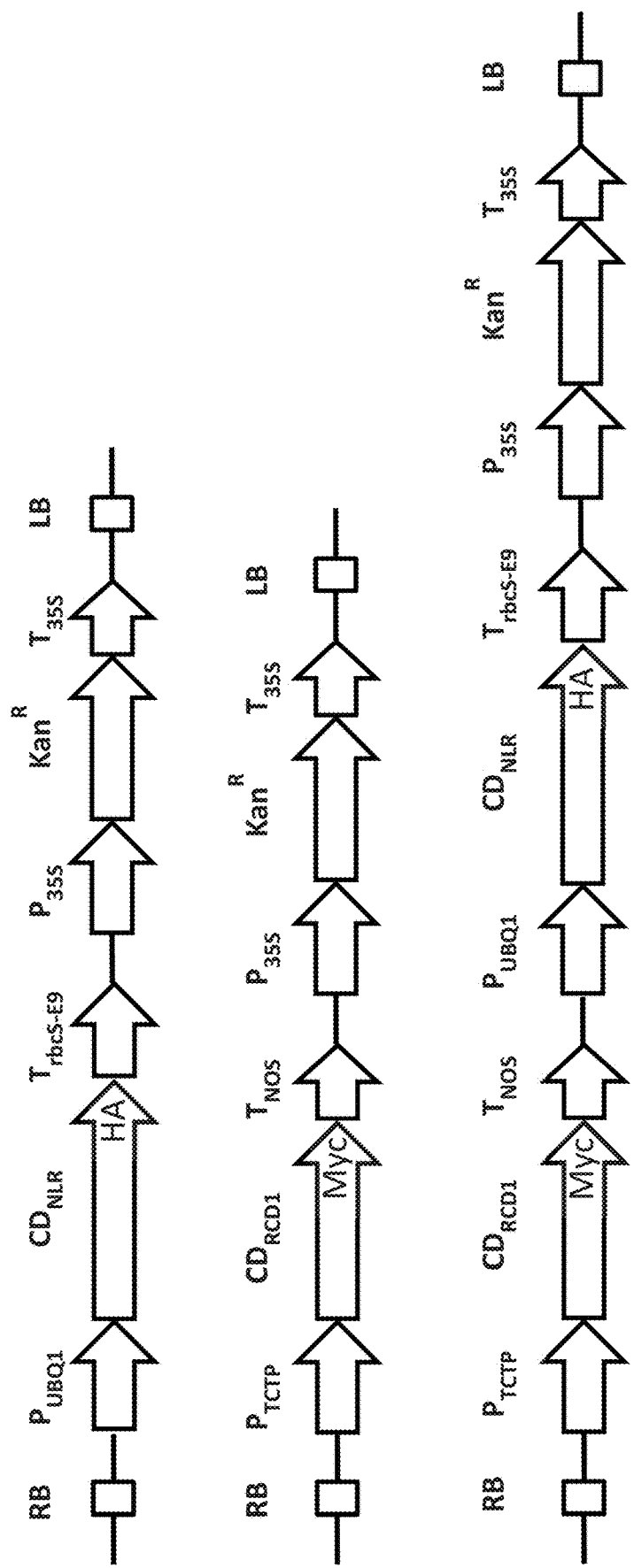
FIG. 5 is a schematic depiction of various constructs employed to overexpress putative resistance cassettes in Col-0 plants. The NLR (Pla-1) and RCD1 (Pla-1) genes were selected to be overexpressed in geminivirus susceptible Col-0 to test for ability to confer virus resistance. The open reading frames (ORFs) of the genes were PCR amplified from cDNAs from Pla-1 leaves with a C-terminal tag sequence for hemagglutinin (HA) and MYC peptide fused at the 3' ends of NLR and RCD1, respectively. The primers employed had the following sequences: Forward primer: 5'-GGTACCCACTAGTCAACAAT GGCTTCTT-CATCTTCTTC-3' (SEQ ID NO: 15) and Reverse primer: 5'-CATGCGTCGACTAAGCGTAATCTGGAACATC-GTATGGGTATATGAAGTGATAT AGCCGCATGCG-3' (SEQ ID NO: 16), resulting in the nucleic acid sequence Pla-1-NLR-HA-NA (SEQ ID NO: 17), which encoded Pla-1-NLR-HA-AA (SEQ ID NO: 18). The protein coding sequences were inserted into UBQ1 promoter-rbcS terminator and TCTP promoter-NOS terminator expression cassettes for NLR-HA and RCD1-MYC, respectively. A plasmid for overexpressing both genes were also made. These plasmids were transferred to a pCAMBIA-based Ti-plasmid vector, which contains a kanamycin-resistance gene (Kan$^R$) for selection in plants within T-DNA borders and introduced into Agrobacterium for transformation of Col-0 plants. Col-0 plants were also transformed with the empty vector to be used as negative control.
Figure 6:
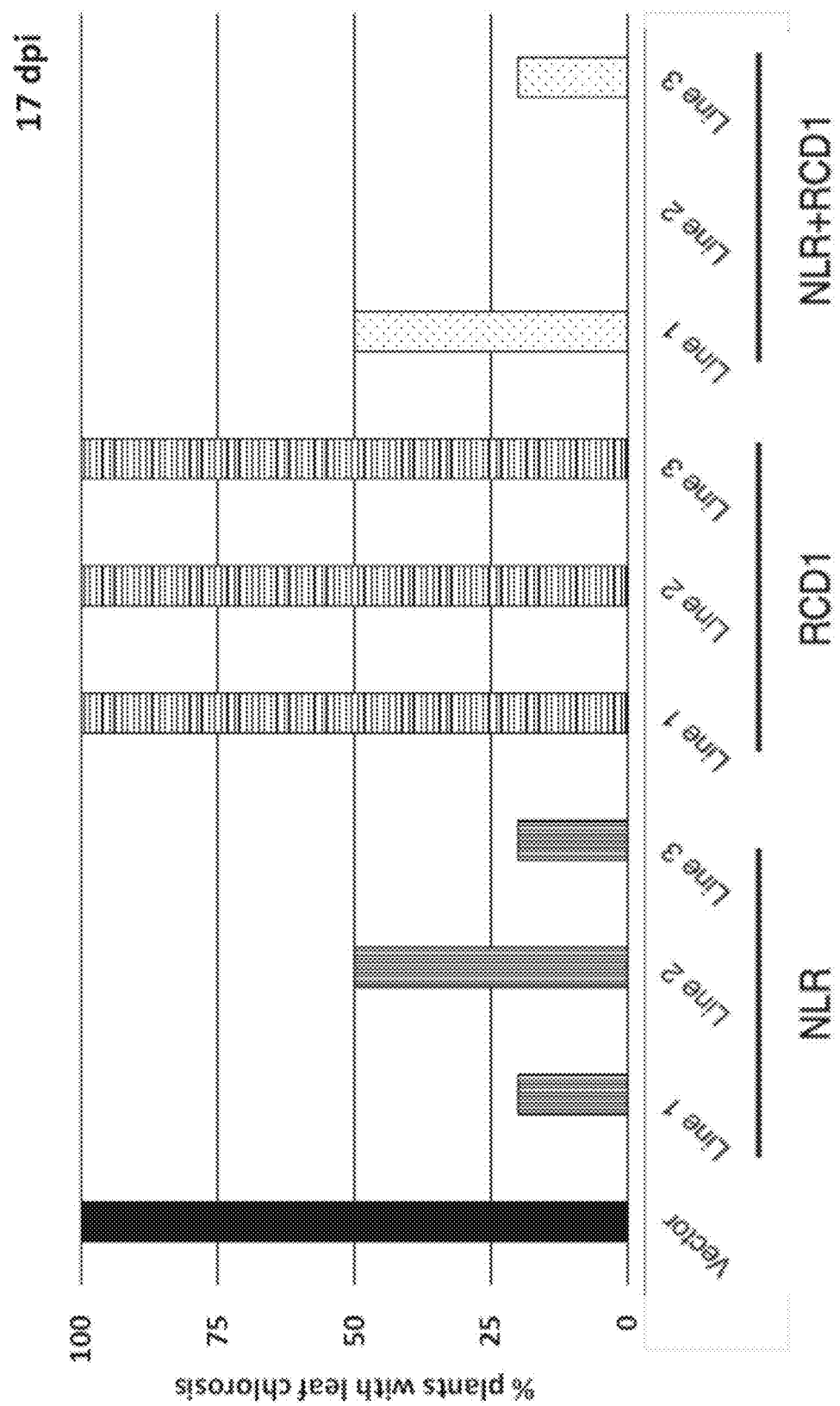
FIG. 6 is a bar graph showing the percentage of transformed T2 plants with symptoms under various conditions. Lines of T2 generation plants with single T-DNA insertions were tested for susceptibility to CaLCuV infection. Six Kan$^R$ plants of each line, which were either homozygous or heterozygous for the transgene, were inoculated with Agrobacterium containing replicons of CaLCuV DNA-A and DNA-B. Viral infection symptoms of leaf curling and chlorosis were recorded. At 2-3 weeks after inoculation, fewer plants from the transgenic lines overexpressing the Pla-1 NLR gene displayed leaf chlorosis than did the control line, which, together with the lines overexpressing the Pla-1 RCD1 gene, all showed leaf chlorosis. Plants transformed with any of the cassettes displayed a similar degree of leaf curling as did the plants transformed with the vector. The results indicated that the Pla-1 NLR cassette was able to prevent or delay leaf chlorosis development during geminivirus infection and was thus likely the gene in the GRP-1 locus that contributed geminivirus resistance to Pla-1. Gene knockdown in Pla-1 plants by tobacco rattle virus (TRV)-mediated virus induced gene silencing (VIGS) can be employed to verify the NLR gene and to screen for the gene possibly responsible for the geminivirus resistance in the GRP-2 locus (17 genes). cDNA fragments of around 500 basepairs (bp) can be inserted into the TRV2 genome in a Ti plasmid vector. Agrobacterium strains containing the knockdown plasmid and a strain containing the TRV1 genome can be mixed to inoculate the rosette center of Pla-1 plants which can be later challenged with CaLCuV infection.
Figure 7:
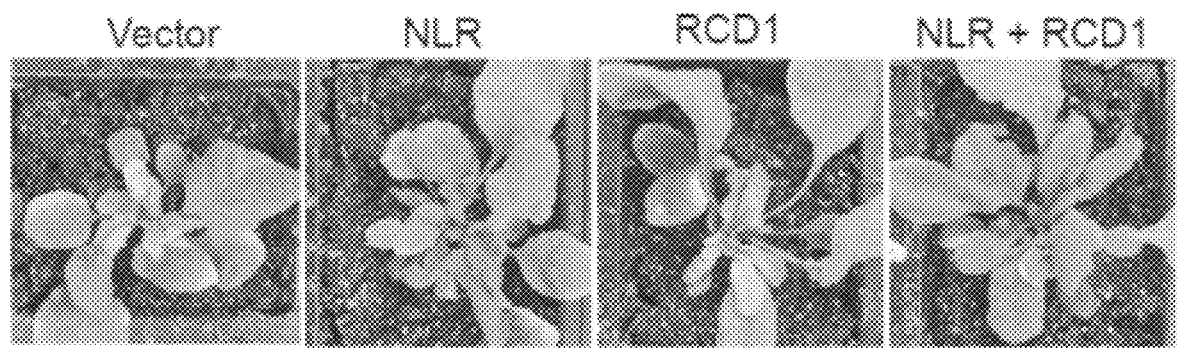
FIG. 7 is a photograph showing the phenotypes of various transgenic plants challenged with CaLCuV infection. Shown are T2 plants segregating Kan$^R$ transgenic lines. Resistance was dose responsive.

This was used as a quantitative trait in determining the virus resistance locus by QTL mapping using the R/qtl software package for R (see FIG. 1A). A strong signal of log of odds from the association of Pla-1 genotype and virus resistance was found at 42.6 cM on Pla-1 chromosome 1 and could span a physical region of 8.0-12.7 Mb. Genotyping at 8.0 or 12.7 Mb, used as proxies for the resistance locus, indicated that the genetic determinant for immunity against CaLCuV infection in Pla-1 is not dominant over nor recessive to Col-0. Further fine-mapping within the 8.0-12.7 Mb region was done with 214 F2 plants containing a partial single copy of Pla-1 sequence starting from 8.0 or 12.7 Mb and with SNP markers at 100 kb intervals. QTL analysis indicated that a 180 kb segment from 11.18 to 11.36 Mb, designated GRP-1, corresponds to the resistance. There is also a weak signal of immunity mapped to a 180 kb region from 11.53 to 11.71 Mb, designated GRP-2, when the data were analyzed in a binary way by combining scores 1 and 2 plant against combined scores 3, 4 and 5 plants.

Figure 8:
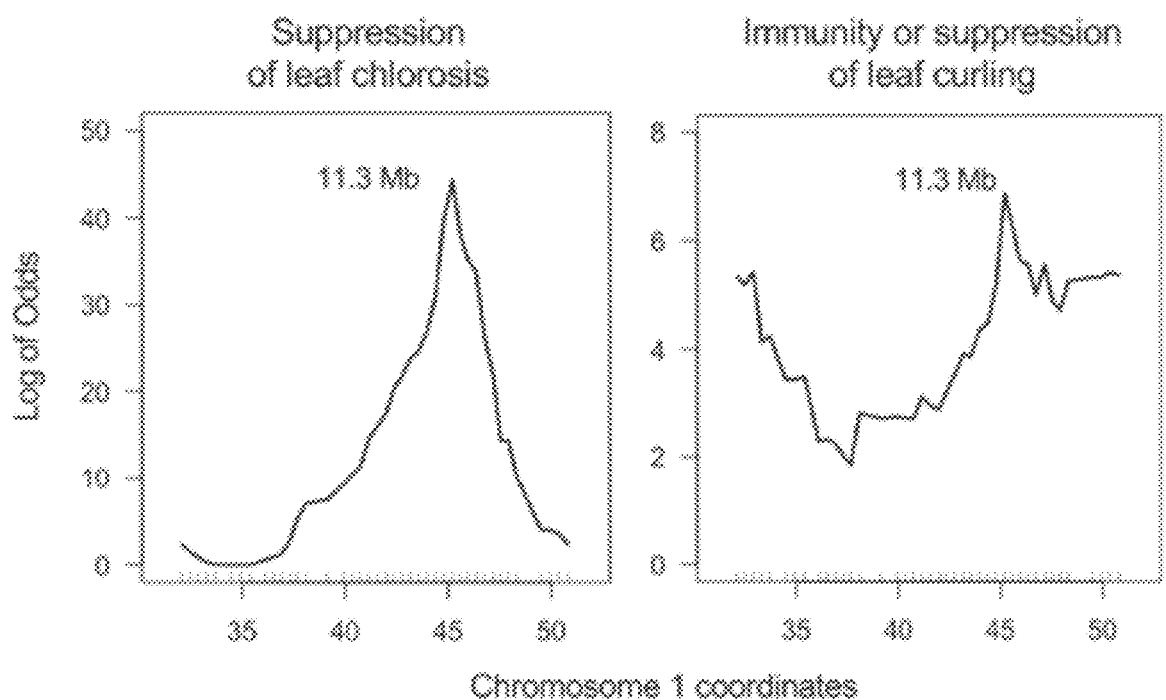
FIG. 8 is a pair of graphs showing the results of genotyping begomovirus resistance between 8.0-12.7 Mb of Pla-1 chromosome 1. Suppression of leaf chlorosis (left panel) was mapped using F2 plants partially homozygous for Col-0. Immunity of suppression of leaf curling (right panel) was using F2 plants partially homozygous for Col-0 or Pla-1. Note the differences in scales of the two y-axis.

The results are presented in FIG. 8. A single copy of GRP-1 was found to be sufficient and necessary for suppressing leaf chlorosis, although full immunity could require homozygosity at GRP-1. It is also important to note that a second, very closely linked gene could be required in combination with GRP-1 for immunity.

Example 2

Identifying the GRP-1 Gene

The dosage-dependent effect of GRP-1 suggested that immunity was related to gene expression levels. RNA-Seq was performed to profile differential expression of the genes in the GRP locus to pinpoint the responsible genes. RNAs were prepared from healthy resistant Pla-1 and susceptible Col-0 leaves and from leaves 4 days after local infection by CaLCuV. Only two genes, AT1G31540 and AT1G32230, showed higher expression levels in healthy Pla-1 vs. healthy Col-0 and in infected Pla-1 vs. infected Col-0 after adjustment using mock infection results. AT1G31540 encodes an NLR while AT1G32230 encodes RCD1. The Pla-1 and Col-0 accessions have amino acid polymorphisms in the two genes.

Example 3

Overexpression of Identified Genes in Col-0

Figure 9A:
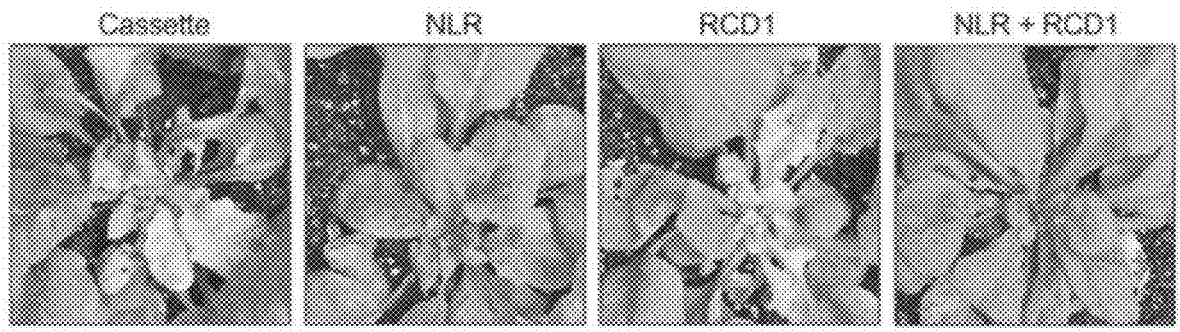
FIGS. 9A-9C summarize the results of experiments showing that the Pla-1 resistance gene is an NLR.
Figure 9B:
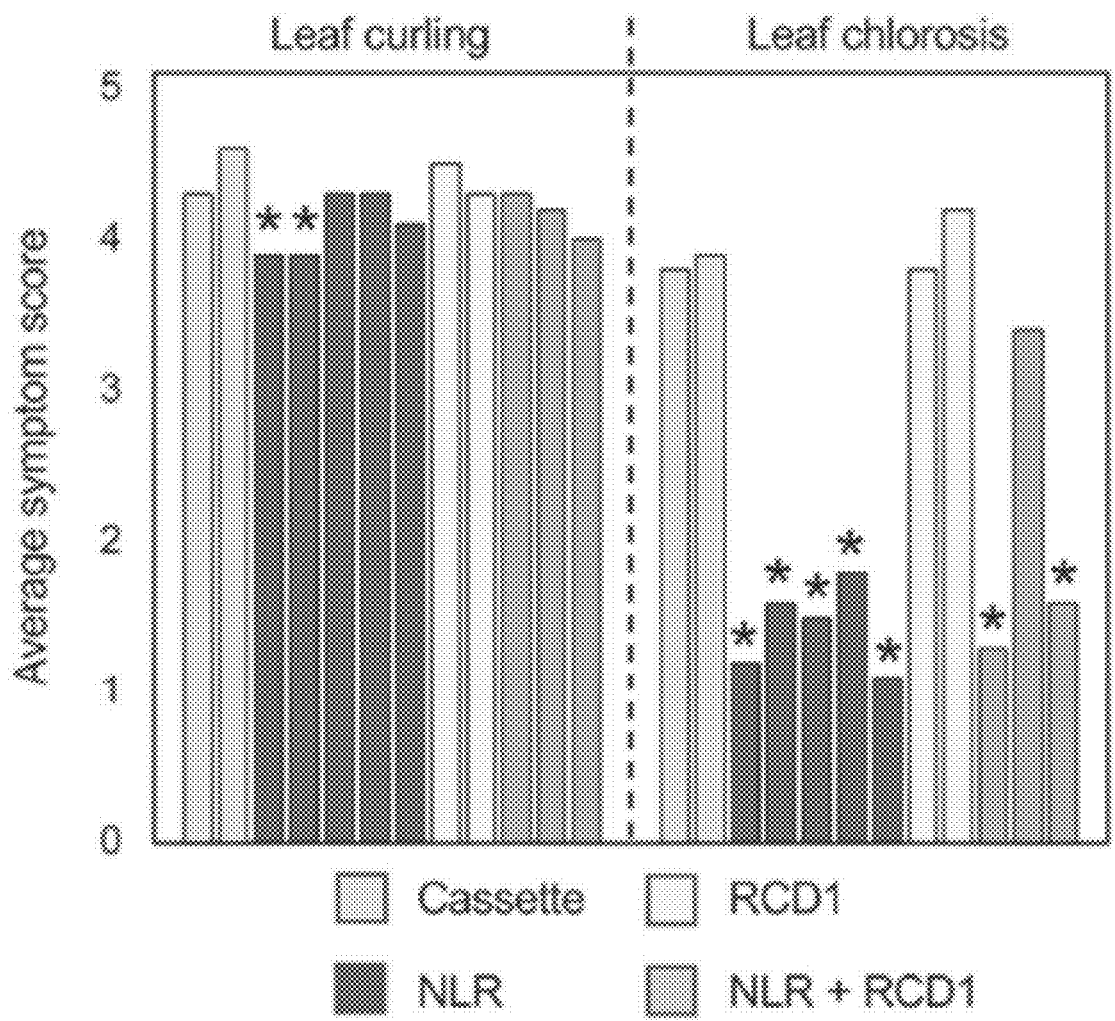
Figure 9C:
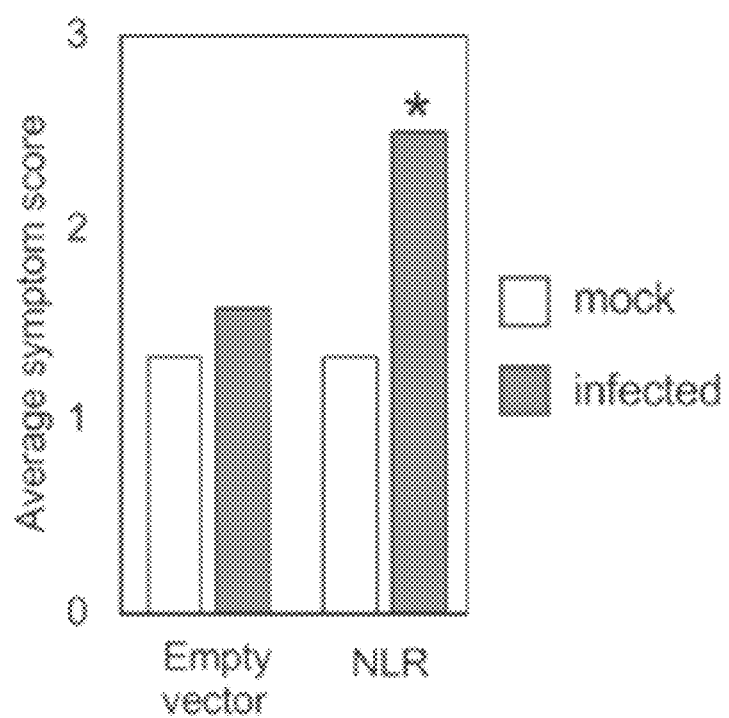

The two Pla-1 genes that were identified were overexpressed in Col-0 using the UBQ1 and TCTP promoters for AT1G31540 and AT1G32230, respectively. CaLCuV-infection of homozygous T3 plants overexpressing Pla-1 AT1G32230 showed severe leaf curling and chlorosis similar to the control plants transformed with the vector plasmid (see FIGS. 9A and 9B). In contrast, multiple T3 lines overexpressing Pla-1 AT1G31540 did not show leaf chlorosis and had a delay in the occurrence and a reduction in leaf curling compared to the control plants in transgenic multiple lines (see FIGS. 9A and 9B). Simultaneous overexpression of AT1G31540 and AT1G32330 did not increase resistance to CaLCuV. TRV-VIGS was also employed to verify the involvement of AT1G31540 in geminivirus resistance. Pla-1 plants silenced for AT1G31540 were infected by CaLCuV and showed symptoms (see FIG. 9C).

These results indicated that AT1G31540 was the sole genetic determinant for suppressing leaf chlorosis in CaLCuV-infected Pla-1 plants and as such, was a likely candidate for suppressing leaf curling and conferring immunity against geminivirus infection. The gene is located on *Arabidopsis* chromosome 1 and is the reverse complement of nucleotides 11,288,378-11,293,799 of Accession No. NC_003070.9 of the GENBANK® biosequence database. The AT1G31540 locus is only 2302 bp from the SNP marker used for mapping (i.e., nucleotide 11,296,101 of Accession No. NC_003070.9 of the GENBANK® biosequence database). AT1G31540 encodes a TIR type nucleotide binding leucine-rich repeat protein (NLR). According to the GENBANK® biosequence database, three transcripts have been identified: Accession No. NM_001123924.2 (encoding Accession No. NP_001117396.1; also referred to as isoform AT1G31540.2), Accession No. NM_001332968.1 (encoding Accession No. NP_001319123.1; also referred to as isoform AT1G31540.1), and Accession No. NM_102893.3 (encoding Accession No. NP_174439.2; also referred to as isoform AT1G31540.3). Accession No. NP_001117396.1 includes the UID, whereas Accession No. NP_001319123.1 and Accession No. NP_174439.2 do not. The difference between Accession No. NM_001332968.1 and Accession No. NM_102893.3 is that nucleotides 1-22 of Accession No. NM_001332968.1 are missing from Accession No. NM_102893.3. This 22 nucleotide sequence is present in the 5' untranslated region (UTR) of Accession No. NM_001332968.1, which is 78 nucleotides in Accession No. NM_001332968.1 and only 56 nucleotides in Accession No. NM_102893.3. Also, Accession Nos. NP_001117396.1, NP_001319123.1, and NP_174439.2 are identical from amino acids 1-762, but thereafter they diverge, with Accession No. NP_001117396.1 including the UID with the sequence as shown and Accession Nos. NP_001319123.1 and NP_174439.2 adding the C-terminal sequence VSSSTLNIISKLFP (SEQ ID NO: 38) after amino acid 762.

REFERENCES

All references cited below or otherwise in the instant disclosure, including but not limited to all patents, patent applications and publications thereof, scientific journal articles, and database entries (e.g., GENBANK® biosequence database entries, including all sequences disclosed therein and all annotations thereof), are incorporated herein by reference in their entireties to the extent that they supplement, explain, provide a background for, or teach methodology, techniques, and/or compositions employed herein.

Altschul et al. (1990) Basic local alignment search tool. J Mol Biol 215: 403-410.

Aragao (1996) Inheritance of foreign genes in transgenic bean (*Phaseolus vulgaris* L.) co-transformed via particle bombardment. Theor Appl Genet 93:142-150.

Aragao et al. (1992) Particle bombardment-mediated transient expression of a Brazil nut methionine-rich albumin in bean (*Phaseolus vulgaris* L.). Plant Mol Biol 20:357-359.

Ausubel et al. (2002) Short Protocols in Molecular Biology, Fifth ed. Wiley, New York, New York, United States of America.

Ausubel et al. (2003) Current Protocols in Molecular Biology, John Wylie & Sons, Inc., New York, New York, United States of America.

Barany & Merrifield (1980) Kinetics and mechanism of the thiolytic removal of the dithiasuccinoyl (Dts) amino protecting group. J Am Chem Soc 102:3084-3095.

Batzer et al. (1991) Enhanced evolutionary PCR using oligonucleotides with inosine at the 3'-terminus. Nuc Acids Res 19:5081.

Beam & Ascencio-Ibanez (2020) Geminivirus Resistance: A Minireview. Front Plant Sci 11:1131.

Christou et al. (1987) Stable transformation of soybean by electroporation and root formation from transformed callus. Proc Natl Acad Sci USA 84:3962-3966.

Clark (ed.) (1997) Plant Molecular Biology: A Laboratory Manual, Chapter 7, Springer-Verlag GmbH & Co. KG, Berlin, Germany.

Creighton (1984) Proteins, WH Freeman & Co., New York, New York, United States of America.

D'Halluin et al. (1992) Transgenic maize plants by tissue electroporation. Plant Cell 4:1495-1505.

Deshayes et al. (1985) Liposome-mediated transformation of tobacco mesophyll protoplasts by an *Escherichia coli* plasmid. EMBO J 4:2731-2737.

Deutscher et al. (eds) (1997) Guide to Protein Purification, Meth Enzymol Volume 182.

Dinant et al. (1997) Coat protein gene-mediated protection in *Lactuca sativa* against lettuce mosaic potyvirus strains. Molecular Breeding, 3:75-86.

Draper et al. (1982) Ti Plasmid Homologous Sequences Present in Tissues from *Agrobacterium* Plasmid-transformed *Petunia* Protoplasts. Plant Cell Physiol 23:451-458.

Goff et al. (2002) A draft sequence of the rice genome (*Oryza sativa* L ssp *japonica*). Science 296:92-100.

Gray et al. (1994) Simplified construction and performance of a device for particle bombardment. Plant Cell Tissue and Organ Culture 37:179-184.

Gruber et al. (1994) Vectors for Plant Transformation. in Methods in Plant Molecular Biology and Biotechnology, Glick & Thompson (eds), CRC Press, Inc., Boca Raton, Florida, United States of America. pages 89-119.

Hain et al. (1985) Uptake, integration, expression and genetic transmission of a selectable chimaeric gene by plant protoplasts. Mol Gen Genet 199:161-168.

Hanley-Bowdoin et al. (1999) Geminiviruses: models for plant DNA replication, transcription, and cell cycle regulation. Cri Rev Plant Sci 18:71-106.

Harlow & Lane (1988) *Antibodies: A Laboratory Manual*, Cold Spring Harbor Laboratory Press, Cold Spring Harbor, New York, United States of America.

Henikoff & Henikoff (1992) Amino Acid Substitution Matrices from Protein Blocks. Proc Natl Acad Sci USA 89:10915-10919.

Hiei et al. (1994) Efficient transformation of rice (*Oryza sativa* L.) mediated by *Agrobacterium* and sequence analysis of the boundaries of the T-DNA. The Plant Journal 6:271-282.

Horsch et al. (1985) A simple and general method for transferring genes into plants. Science 227:1229-1231.

Jefferson et al. (1987) GUS fusions: beta-glucuronidase as a sensitive and versatile gene fusion marker in higher plants. EMBO J 3901-3907.

Kado & Hooykaas (1991) Molecular mechanisms of crown gall tumorigenesis. Crit Rev Plant Sci 10:1-32.

Karlin & Altschul (1993) Applications and statistics for multiple high-scoring segments in molecular sequences. Proc Natl Acad Sci USA 90(12):5873-5877.

Kim & Minamikawa (1996) Transformation and regeneration of French bean plants by the particle bombardment process. Plant Science 117:131-138.

Klein et al. (1988) Factors Influencing Gene Delivery into *Zea Mays* Cells by High-Velocity Microprojectiles. BioTechnology 6:559-563.

Klein et al. (1992) BioTechnology 10:268.

Kuchler (1997) Biochemical Methods in Cell Culture and Virology, Dowden, Hutchinson and Ross, Inc., Stroudsburg, Pennsylvania, United States of America.

Kyte & Doolittle (1982) A Simple Method for Displaying the Hydropathic Character of a Protein. J Mol Biol 157:105-132.

Lazarowitz (1992) Geminiviruses: Genome structure and gene function. Crit Rev Plant Sci 11:327-349.

Merrifield et al. (1963) Solid Phase Peptide Synthesis. I. The Synthesis of a Tetrapeptide J Am Chem Soc 85:2149-54.

Miki et al. (1993) Procedures for Introducing Foreign DNA into Plants. in Methods in Plant Molecular Biology and Biotechnology, Glick & Thompson (eds), CRC Press, Inc., Boca Raton, Florida, United States of America. pages 67-88.

Moloney et al. (1989) High efficiency transformation of Brassica *napus* using Agrobacterium vectors. Plant Cell Reports 8:238-242.

Needleman & Wunsch (1970) A general method applicable to the search for similarities in the amino acid sequence of two proteins. J Mol Biol 48:443-453.

Ohtsuka et al. (1985) An alternative approach to deoxyoligonucleotides as hybridization probes by insertion of deoxyinosine at ambiguous codon positions. J Biol Chem 260:2605-2608.

Paterson (1996) The DNA Revolution, Chapter 2 in Genome Mapping in Plants, Paterson (ed), Academic Press/R.G. Lands Co., Austin, Texas, United States of America.

Pearson & Lipman (1988) Improved tools for biological sequence comparison. Proc Natl Acad Sci USA 85:2444-2448.

Reiter et al. (1992) Genetic Linkage of the *Arabidopsis* Genome: Methods for Mapping with Recombinant Inbreds and Random Amplified Polymorphic DNAs (RAPDs) in *Methods in Arabidopsis Research*, World Scientific Press, River Edge, New Jersey, United States of America.

Reyes et al. (2018) A VIGS screen identifies immunity in the *Arabidopsis* Pla-1 accession to viruses in two different genera of the Geminiviridae. The Plant Journal 92:796-807.

Rossolini et al. (1994) Use of deoxyinosine-containing primers vs degenerate primers for polymerase chain reaction based on ambiguous sequence information. Mol Cell Probes 8:91-98.

Russell et al. (1993) Stable transformation of *Phaseolus vulgaris* via electric-discharge mediated particle acceleration. Plant Cell Rep 12:165-169.

Sambrook & Russell (2001) Molecular Cloning: A Laboratory Manual, 3rd ed. Cold Spring Harbor Laboratory Press, Cold Spring Harbor, New York, United States of America.

Sanford (1988) The biolistic process. Trends Biotech 6:299-302.

Sanford (1990) Biolistic plant transformation. Physiol Plant 79:206-209.

Sanford et al. (1987) Delivery of substances into cells and tissues using a particle bombardment process. Part Sci Technol 5:27-37.

Schultz et al. (1998)-DNA tagging in *Arabidopsis thaliana*: Cloning by gene disruption, in *Plant Molecular Biology Manual*, $2^{nd}$ edition, Gelvin et al. (eds.) Kluwer Academic Publishers, New York, New York, United States of America.

Scopes (1982) *Protein Purification: Principles and Practice*, Springer-Verlag, New York, New York, United States of America.

Sherman et al. (1982) *Methods in Yeast Genetics*, Cold Spring Harbor Laboratory Press, Cold Spring Harbor, New York, United States of America.

Silhavy et al. (1984) *Experiments with Gene Fusions*, Cold Spring Harbor Laboratory, Cold Spring Harbor, New York, United States of America.

Smith & Waterman (1981) Identification of common molecular subsequences. Adv Appl Math 2:482.

Southern et al. (1991) Identification of an epitope on the P and V proteins of simian virus 5 that distinguishes between two isolates with different biological characteristics. J Gen Virol 72:1551-1557.

Spencer et al. (1994) Production of fertile transgenic maize by electroporation of suspension culture cells. Plant Mol Biol 24:51-61.

Stewart & Young (1984) *Solid Phase Peptide Synthesis*, $2^{nd}$ ed., Pierce Chemical Co., Rockford, Illinois, United States of America.

Swarts et al. (2014) DNA-guided DNA interference by a prokaryotic Argonaute. Nature 507(7491): 258-261.

Tijssen (1993) *Laboratory Techniques in Biochemistry and Molecular Biology—Hybridization with Nucleic Acid Probes*. Elsevier, New York, New York, United States of America.

Timmermans et al. (1994) Geminiviruses and Their Uses as Extrachromosomal Replicons. Annu Rev Plant Physiol 45:79-112.

U.S. Patent Application Publication Nos. 2003/0232410, 2005/0026157, 2005/0064474, 2005/0208489, 2006/0063231, 2008/0159996, 2010/0218264, 2011/0265198, 2012/0017290, 2013/0122591, 2013/0137104, 2013/0177960, 2013/0177983, 2015/0056705, 2015/0067922, 2017/0114351, 2017/0166912, 2018/0073035.

U.S. Pat. Nos. 4,554,101; 4,945,050; 5,591,616; 5,932,782; 5.981,184; 6,503,717; 6,534,261; 6,599,692; 6,689,558; 7,067,317; 7,262,054; 7,732,667; 7,888,121; 7,914,796; 7,951,925; 7,972,854; 8,110,379; 8,409,861; 8,586,526; 8,766,035; 8,945,868; 8,956,828; 9,005,973; 9,045,763; 9,745,600; 10,557,146; 10,662,437.

Valles et al. (1984) *Agrobacterium*-mediated transformation of commercial melon (*Cucumis melo* L., cv. Amarillo Oro). Plant Cell Rep 13:145-148.

Womble (2000) GCG: The Wisconsin Package of sequence analysis programs. Methods Mol Biol 132: 3-22.

Zhang et al. (1991) Efficient transformation of tobacco by ultrasonication. BioTechnology 9:996-997.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A heterologous expression cassette comprising a chimeric nucleotide sequence that is derived from at least two different species, the chimeric nucleotide sequence comprising:
   (i) a polynucleotide that encodes a polypeptide that is at least 96% identical to SEQ ID NO: 2;
   (ii) operably linked to a promoter that is functional in plants; and
   (iii) a transcription terminator,
   wherein the promoter, the polynucleotide, and the transcription terminator are not all naturally occurring in a single plant genus, species, accession, or ecotype.

2. The expression cassette of claim 1, wherein the promoter is functional in a plant selected from the group consisting of tomato, cassava, and cotton.

3. The expression cassette of claim 1, wherein the promoter is selected from the group consisting of an Arabidopsis translationally controlled tumor protein (AtTCTP) promoter, an Arabidopsis ubiquitin extension protein 1 (AtUBQ1) promoter, a cauliflower mosaic virus 35S promoter, and a duplicated 35S (2×35S) promoter, optionally wherein the AtTCTP promoter comprises a nucleotide sequence as set forth in SEQ ID NO: 29, the AtUBQ1 promoter comprises a nucleotide sequence as set forth in SEQ ID NO: 30, the cauliflower mosaic virus 35S promoter comprises a nucleotide sequence as set forth in SEQ ID NO: 31, and/or the 2×35S promoter comprises a nucleotide sequence as set forth in SEQ ID NO: 32.

4. The expression cassette of claim 1, wherein the transcription terminator is selected from the group consisting of an Agrobacterium NOS terminator and a pea rbcS (E9) terminator, optionally wherein the Agrobacterium NOS terminator comprises, consists essentially of, or consists of a nucleotide sequence as set forth in SEQ ID NO: 33 and/or the pea rbcS (E9) terminator comprises, consists essentially of, or consists of a nucleotide sequence as set forth in SEQ ID NO: 34.

5. The expression cassette of claim 1, wherein the polynucleotide encodes an amino acid sequence comprising, consisting essentially of, or consisting of SEQ ID NO: 2, operably linked to both the promoter and the transcription terminator.

6. The expression cassette of claim 5, wherein the polynucleotide further comprises a tag sequence in the same reading frame as the polynucleotide, and further wherein the tag sequence is present in the expression cassette (a) between the promoter and the polynucleotide, and/or (b) between the polynucleotide and the terminator.

7. The expression cassette of claim 6, wherein the tag sequence encodes a peptide tag comprising an amino acid sequence selected from the group consisting of SEQ ID NOs: 6, 7, 20, 22, 24, 26, 28, 37, or any combination thereof.

8. The expression cassette of claim 7, wherein the expression cassette comprises a promoter, a polynucleotide, a tag sequence, and a transcription terminator in 5' to 3' orientation selected from the group consisting of:
   (a) SEQ ID NO: 30, SEQ ID NO: 1, SEQ ID NO: 35 or SEQ ID NO: 36, and SEQ ID NO: 34;
   (b) SEQ ID NO: 29, SEQ ID NO: 1, SEQ ID NO: 35 or SEQ ID NO: 36, and SEQ ID NO: 33;
   (c) SEQ ID NO: 32, SEQ ID NO: 1, SEQ ID NO: 35 or SEQ ID NO: 36, and SEQ ID NO: 34; and
   (d) SEQ ID NO: 29, SEQ ID NO: 1, SEQ ID NO: 19, and SEQ ID NO: 33.

9. The expression cassette of claim 8, wherein the expression cassette comprises a first promoter, a first polynucleotide, a first tag sequence, and a first transcription terminator, and a second promoter, a second polynucleotide, a second tag sequence, and a second transcription terminator.

10. The expression cassette of claim 9, wherein the first promoter, first polynucleotide nucleotide sequence, first tag sequence, and first transcription terminator in 5' to 3' orientation are SEQ ID NO: 29, SEQ ID NO: 1, SEQ ID NO: 19, and SEQ ID NO: 33 and the second promoter, second polynucleotide nucleotide sequence, second tag sequence, and second transcription terminator in 5' to 3' orientation are SEQ ID NO: 30, SEQ ID NO: 1, SEQ ID NO: 35 or SEQ ID NO: 36, and SEQ ID NO: 34.

11. A recombinant vector comprising the expression cassette of claim 1.

12. A cell comprising the expression cassette of claim 1.

13. A transgenic plant comprising the expression cassette of claim 1.

14. The transgenic plant of claim 13, wherein the transgenic plant is a dicot.

15. The transgenic plant of claim 14, wherein the transgenic plant is selected from the group consisting of tomato, cassava, and cotton, optionally wherein the promoter is a tomato, a cassava, or a cotton promoter.

16. Progeny and/or seed from the transgenic plant of claim 13, wherein the progeny and/or seed comprises the expression cassette.

17. A method for altering geminivirus resistance of a plant, the method comprising expressing in the plant the expression cassette of claim 1.

18. The method of claim 17, wherein the plant is selected from the group consisting of tomato, cassava, and cotton, optionally wherein the promoter is a tomato, a cassava, or a cotton promoter.

19. A method for suppressing virus-induced leaf chlorosis, leaf curling, or both in a plant, the method comprising expressing in the plant the expression cassette of claim 1.

20. The method of claim 19, wherein the plant is selected from the group consisting of tomato, cassava, and cotton, optionally wherein the promoter is a tomato, a cassava, or a cotton promoter.

* * * * *